United States Patent [19]

Himmelsbach et al.

[11] Patent Number: 5,650,424

[45] Date of Patent: Jul. 22, 1997

[54] CYCLIC UREA DERIVATIVES, PHARMACEUTICAL COMPOSITIONS CONTAINING THESE COMPOUNDS AND PROCESSES FOR PREPARING THEM

[75] Inventors: Frank Himmelsbach, Mittelbiberach; Helmut Pieper; Volkhard Austel, both of Biberach; Guenter Linz, Mittelbiberach; Thomas Mueller, Biberach; Johannes Weisenberger, Biberach; Wolfgang Eisert, Biberach, all of Germany

[73] Assignee: Dr. Karl Thomae GmbH, Biberach an der Riss, Germany

[21] Appl. No.: 521,338

[22] Filed: Aug. 29, 1995

Related U.S. Application Data

[62] Division of Ser. No. 144,909, Oct. 28, 1993, Pat. No. 5,478,942, which is a division of Ser. No. 849,557, Mar. 11, 1992, Pat. No. 5,276,049.

[30] Foreign Application Priority Data

Mar. 12, 1991 [DE] Germany .......................... 41 07 857.8

[51] Int. Cl.⁶ ....................... A61K 31/415; C07D 233/76
[52] U.S. Cl. ......................... 514/391; 514/326; 546/210; 548/317.1; 548/321.1

[58] Field of Search ....................... 514/391, 326; 548/321.1, 317.1; 546/210

[56] References Cited

U.S. PATENT DOCUMENTS 4,055,410  10/1977  Cheng ............................ 71/90

FOREIGN PATENT DOCUMENTS 697572   11/1964  Canada .
2724819  12/1978  Germany .
3604040  2/1986   Germany .

*Primary Examiner*—Jacqueline Haley
*Attorney, Agent, or Firm*—Robert P. Raymond; Wendy E. Rieder; Mary-Ellen M. Devlin

[57] ABSTRACT

The invention relates to cyclic urea derivatives of general formula

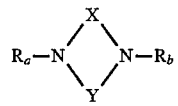

(I)

wherein $R_a$, $R_b$, X and Y are as defined herein, pharmaceutical compositions containing the derivatives and processes for preparing them.

5 Claims, No Drawings

CYCLIC UREA DERIVATIVES, PHARMACEUTICAL COMPOSITIONS CONTAINING THESE COMPOUNDS AND PROCESSES FOR PREPARING THEM

This is a division of application Ser. No. 08/144,909, filed Oct. 28, 1993, U.S. Pat. No. 5,478,942 which is a division of application Ser. No. 07/849,557, filed Mar. 11, 1992 U.S. Pat. No. 5,276,049.

The invention relates to cyclic urea derivatives of general formula

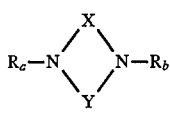 (I)

the tautomers and stereoisomers thereof, including the mixtures and the addition salts thereof, particularly the physiologically acceptable addition salts with inorganic or organic acids or bases which have, inter alia, valuable pharmacological properties, preferably aggregation-inhibiting effects, pharmaceutical compositions which contain these compounds and processes for preparing them.

In general formula I above

X represents a carbimino group optionally substituted at the nitrogen atom by an alkyl, aralkyl, aryl, heteroaryl or cyano group, or a carbonyl, thiocarbonyl, sulphinyl or sulphonyl group, Y represents a straight-chained $C_{2-4}$-alkylene or alkenylene group optionally substituted by $R_c$ or $R_d$ or by $R_c$ and $R_d$, wherein the above-mentioned alkylene or alkenylene groups additionally may be mono- or disubstituted by fluorine, chlorine or bromine atoms or by alkyl, trifluoromethyl, aralkyl, aryl, heteroaryl or alkylcarbonyl groups, whilst the substituents may be identical or different and, in addition, one or two methylene groups may each be replaced by a carbonyl group, or Y represents a 1,2-cycloalkylene group having 4 to 7 carbon atoms optionally substituted by $R_c$ or $R_d$ or by $R_c$ and $R_d$, or Y represents a 1,2-cycloalkenylene group having 4 to 7 carbon atoms or a 1,2-phenylene group in which one or two methine groups may be replaced by a nitrogen atom and which may be substituted in the carbon skeleton by a fluorine, chlorine or bromine atom, by a $C_{1-4}$-alkyl group, by a trifluoromethyl, hydroxy, alkoxy, alkylsulphenyl, alkylsulphinyl, alkylsulphonyl, alkylcarbonyl, arylcarbonyl, alkoxycarbonyl, carboxy, nitro, $(R_1)_2N$—, $(R_1)_2NCO$— or $(R_1)_2NSO_2$— group (wherein the groups $R_1$ may be identical or different and may each represent a hydrogen atom or an alkyl, aralkyl, aryl or heteroaryl group), or by a $R_1NH$ group substituted by an alkylcarbonyl, arylcarbonyl, aralkylcarbonyl, heteroarylcarbonyl, alkylsulphonyl, aralkylsulphonyl or arylsulphonyl group, and wherein, additionally, one or two —CH=CH— groups may each be replaced by a —CO—$NR_1$— group, or Y represents a —CO—NH—, —NH—CO—, —CH=N— or —N=CH— group optionally substituted by $R_c$ or $R_d$, one of the groups $R_a$ to $R_d$ represents a group of formula

A-B-C- wherein

A represents a straight-chained or branched $C_{1-5}$-aminoalkyl group, an amino, amidino or guanidino group, whilst in each of the above-mentioned groups at one of the nitrogen atoms, one or two hydrogen atoms may be replaced by a $C_{1-4}$-alkyl or one hydrogen atom may be replaced by a $C_{2-5}$-alkoxycarbonyl group or by an alkylcarbonyl, arylcarbonyl, aryloxycarbonyl or aralkoxycarbonyl group, or A may represent a cyano group, a cyanoalkyl group having 1 to 4 carbon atoms in the alkyl moiety or, if A is bound to a nitrogen atom of groups B or C which is not part of a lactam group, it may represent a hydrogen atom or an alkyl group, B represents a bond, an alkylene or alkenylene group, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, $(R_1)_2N$—, $(R_1)_2NCO$—, $(R_1)_2NSO_2$— or nitro groups or by $R_1NH$ groups substituted by an alkylcarbonyl, aralkylcarbonyl, arylcarbonyl, heteroarylcarbonyl, alkylsulphonyl, aralkylsulphonyl or arylsulphonyl group, whilst the substituents may be identical or different, a pyridinylene, pyrimidinylene, pyrazinylene, pyridazinylene or triazinylene group, which may be alkyl-substituted in the carbon skeleton, whilst additionally one or two —CH=N— groups may be replaced by a —CO—$NR_1$— group and one of the nitrogen atoms, instead of being bound to the group $R_1$, may also be bound to the group C, provided that the latter is not attached to group B by a heteroatom or a carbonyl group, a cyclopropylene group optionally substituted by an alkyl, aralkyl or aryl group, a $C_{4-5}$-cycloalkylene group optionally substituted by an alkyl, aralkyl or aryl group, wherein a CH moiety may be replaced by a nitrogen atom and additionally a methylene group adjacent to the nitrogen atom may be replaced by a carbonyl group, a $C_{6-7}$-cycloalkylene group optionally substituted by an alkyl, aralkyl or aryl group, wherein one or two CH moieties in the 1,4-position relative to one another may each be replaced by a nitrogen atom, whilst additionally one or two of the methylene groups adjacent to a nitrogen atom may each be replaced by a carbonyl group, a biphenylene group which may be mono- or disubstituted by fluorine, chlorine or bromine atoms or by alkyl, trifluoromethyl, hydroxy, alkoxy, alkylsulphenyl, alkylsulphinyl, alkylsulphonyl, alkylcarbonyl-$NR_1$— or alkylsulphonyl-$NR_1$— groups, whilst the substituents may be identical or different and $R_1$ is as hereinbefore defined, and C represents an alkylene or alkenylene group optionally substituted by a hydroxy, alkoxy or $(R_1)_2N$— group, an alkylenecarbonyl group connected to the group B via the carbonyl group, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, $(R_1)_2N$—, $(R_1)_2NCO$—, $(R_1)_2NSO_2$— or nitro groups or by $R_1NH$— groups substituted by an alkylcarbonyl, aralkylcarbonyl, arylcarbonyl, heteroarylcarbonyl, alkylsulphonyl, aralkylsulphonyl or arylsulphonyl group, whilst the substituents may be identical or different, an indanylene or 1,2,3,4-tetrahydronaphthylene group, wherein in each case the saturated ring is bound to the group A and the aromatic ring is bound to the cyclic urea skeleton, a pyridinylene, pyrimidinylene, pyrazinylene, pyridazinylene or triazinylene group which may be substituted in the carbon skeleton by an alkyl group, whilst additionally one or two —CH=N— groups may each be replaced by a —CO—NR$_1$— group and one of the nitrogen atoms, instead of being bound to the group R$_1$, may also be bound to the group B, provided that the latter is not a bond or does not adjoin the group C with a heteroatom, a C$_{4-5}$-cycloalkylene group optionally substituted by an alkyl, aralkyl or aryl group wherein a CH moiety may be replaced by a nitrogen atom and in addition a methylene group adjacent to the nitrogen atom may be replaced by a carbonyl group, or a C$_{6-7}$-cycloalkylene group optionally substituted by an alkyl, aralkyl or aryl group, wherein one or two CH moieties located in the 1,4-position relative to each other may each be replaced by a nitrogen atom, whilst additionally one or two of the methylene groups adjacent to a nitrogen atom may each be replaced by a carbonyl group, a second of the groups R$_a$ to R$_d$ represents a group of the formula

F-E-D- wherein

D represents a C$_{1-5}$-alkylene group or a C$_{2-5}$-alkenylene group, a phenylene group which may be mono- or disubstituted by fluorine, chlorine or bromine atoms, by C$_{1-4}$-alkyl groups, by trifluoromethyl, hydroxy, alkoxy, alkylsulphenyl, alkylsulphinyl, alkylsulphonyl, carboxyalkoxy, alkoxycarbonylalkoxy, aralkoxycarbonyl-alkoxy, (R$_1$)$_2$N—, (R$_1$)$_2$NCO—, (R$_1$)$_2$NSO$_2$— or nitro groups or by R1NH— groups substituted by an alkylcarbonyl, aralkylcarbonyl, arylcarbonyl, heteroarylcarbonyl, alkylsulphonyl, aralkylsulphonyl or arylsulphonyl group, the substituents being identical or different, a pyridinylene, pyrimidinylene, pyrazinylene, pyridazinylene or triazinylene group which may be alkyl-substituted in the carbon skeleton, whilst additionally one or two —CH=N— groups may each be replaced by a —CO—NR$_1$— group and one of the nitrogen atoms, instead of being bound to the group R$_1$, may also be bound to the group E, provided that the latter is not a bond or is not bound to the group D by means of a heteroatom, a CD$_{4-5}$-cycloalkylene group optionally substituted by an alkyl, aralkyl or aryl group, wherein a CH moiety may be replaced by a nitrogen atom and in addition a methylene group adjacent to the nitrogen atom may be replaced by a carbonyl group, a C$_{6-7}$-cycloalkylene group optionally substituted by an alkyl, aralkyl or aryl group, wherein one or two CH moieties in the 1,4-position relative to each other may each be replaced by a nitrogen atom, whilst additionally one or two of the methylene groups adjacent to the nitrogen atom may each be replaced by a carbonyl group, or a C$_{2-6}$-alkylene group interrupted by the group W, wherein W represents an oxygen or sulphur atom, a sulphinyl, sulphonyl, R$_1$N=, (alkylcarbonyl)N=, (aralkylcarbonyl)N=, (arylcarbonyl)N=, (heteroarylcarbonyl)N=, (alkylsulphonyl)N=, (arylsulphonyl)N=, aminocarbonyl or carbonylamino group, E represents a bond, a C$_{1-5}$-alkylene group or a C$_{2-5}$-alkenylene group, each of which may be substituted by one or two alkyl groups, or by a hydroxy, alkoxy, amino, alkylamino, aralkylamino, dialkylamino, bis(aralkyl)amino, carboxyalkyl, alkoxycarbonylalkyl or aralkoxycarbonylalkyl group, a phenylene group which may be mono- or disubstituted by fluorine, chlorine or bromine atoms, by C$_{1-4}$-alkyl groups, by trifluoromethyl, hydroxy, alkoxy, alkylsulphenyl, alkylsulphinyl, alkylsulphonyl, (R$_1$)$_2$N—, (R$_1$)$_2$NCO—, (R$_1$)$_2$NSO$_2$— or nitro groups or by R$_1$NH— groups substituted by an alkylcarbonyl, aralkylcarbonyl, arylcarbonyl, heteroarylcarbonyl, alkylsulphonyl, aralkylsulphonyl or arylsulphonyl group, the substituents being identical or different, a pyridinylene, pyrimidinylene, pyrazinylene, pyridazinylene or triazinylene group which may be alkyl-substituted in the carbon skeleton, whilst additionally one or two —CH=N— groups may each be replaced by a —CO—NR$_1$— group and one of the nitrogen atoms, instead of being bound to the group R$_1$, may also be bound to the group D, a C$_{4-5}$-cycloalkylene group optionally substituted by an alkyl, aralkyl or aryl group, wherein a CH moiety may be replaced by a nitrogen atom and in addition a methylene group adjacent to the nitrogen atom may be replaced by a carbonyl group, a C$_{6-7}$-cycloalkylene group optionally substituted by an alkyl, aralkyl or aryl group, wherein one or two CH moieties in the 1,4-position relative to each other may each be replaced by a nitrogen atom, whilst additionally one or two of the methylene groups adjacent to a nitrogen atom may each be replaced by a carbonyl group, an alkylenearylene group linked to the group D via the aryl moiety or an alkylene group linked to the group D via the group W, where W is as hereinbefore defined, and F represents a carbonyl group substituted by a hydroxy or C$_{1-6}$-alkoxy group, whilst a C$_{1-3}$-alkoxy group may be substituted in the 1-, 2- or 3-position by an aryl or heteroaryl group or in the 2- or 3-position by a pyrrolidin-2-on-1-yl, morpholino, thiomorpholino or 1-oxido-thiomorpholino group, or F may represent a sulpho, phosphono, O-alkylphosphono or tetrazol-5-yl group, whilst if A represents a cyano group or an amino or aminoalkyl group optionally benzoylated or benzyloxy-carbonylated at the nitrogen atom, the shortest spacing between the nitrogen atom of these groups and group F is at least 10 bonds, the third of the groups R$_a$ to R$_d$ represents a hydrogen atom, an alkyl, perfluoroalkyl, aralkyl, aryl or heteroaryl group or, if the third of the groups R$_a$ to R$_d$ is connected to an unsaturated carbon atom of group Y, it may represent an alkoxy, alkylsulphenyl or (R$_1$)$_2$N— group, and the fourth of the groups R$_a$ to R$_d$ represents a hydrogen atom, an alkyl, aralkyl, aryl or heteroaryl group, or R$_a$ or R$_b$ together with an adjacent group R$_c$ or R$_d$ may also represent a bond, and, unless otherwise specified, the above-mentioned alkyl, alkylene, alkenylene or alkoxy moieties may each contain 1 to 3 carbon atoms, and the term "an aryl group" used above denotes a phenyl group which may be monosubstituted by a trifluoromethyl, carboxy, $(R_1)_2NCO—$, alkoxycarbonyl, alkylcarbonyl, alkylsulphenyl, alkylsulphinyl, alkylsulphonyl, nitro, $(R_1)_2N—$, alkylcarbonyl-$NR_1—$, aralkylcarbonyl-$NR_1—$, arylcarbonyl-$NR_1—$, heteroarylcarbonyl—$NR_1—$, alkylsulphonyl-$NR_1—$, aralkylsulphonyl-$NR_1—$, arylsulphonyl-$NR_1—$ or $(R_1)_2N$-sulphonyl group or may be mono-, di- or trisubstituted by fluorine, chlorine or bromine atoms or by hydroxy, alkoxy or alkyl groups having 1 to 4 carbon atoms, and the term "a heteroaryl group" used above denotes a 5-membered heteroaromatic ring which contains an oxygen, sulphur or nitrogen atom, a nitrogen atom and an oxygen, sulphur or nitrogen atom or two nitrogen atoms and an oxygen, sulphur or nitrogen atom or a 6-membered heteroaromatic ring which contains one, two or three nitrogen atoms and in which, additionally, one or two —CH=N— groups may each be replaced by a —CO—$NR_1$— group, whilst the above-mentioned heteroaromatic rings may additionally be substituted by one or two alkyl groups or by a fluorine, chlorine or bromine atom or by a hydroxy or alkoxy group.

Preferred compounds of general formula I above are those wherein

X represents a carbimino group optionally substituted at the nitrogen atom by an alkyl, aralkyl, aryl, heteroaryl or cyano group, or a carbonyl, thiocarbonyl, sulphinyl or sulphonyl group, Y represents a straight-chained $C_{2-3}$-alkylene or alkenylene group optionally substituted by $R_c$ or $R_d$ or by $R_c$ and $R_d$, which may be mono- or disubstituted by fluorine, chlorine or bromine atoms or by alkyl, trifluoromethyl, aralkyl, aryl, heteroaryl or alkylcarbonyl groups, whilst the substituents may be identical or different and, in addition, one or two methylene groups may each be replaced by a carbonyl group, or Y represents a 1,2-cyclohexylene group optionally substituted by $R_c$ or $R_d$ or by $R_c$ and $R_d$, or Y represents a 1,2-cyclohexenylene group or a 1,2-phenylene group wherein one or two CH groups may each be replaced by a nitrogen atom and which may be substituted in the carbon skeleton by a fluorine, chlorine or bromine atom, by a $C_{1-4}$-alkyl group, by a trifluoromethyl, hydroxy, alkoxy, alkylsulphenyl, alkylsulphinyl, alkylsulphonyl, alkylcarbonyl, arylcarbonyl, alkoxycarbonyl, carboxy, nitro, $(R_1)_2N—$, $(R_1)_2NCO—$ or $(R_1)_2NSO_2—$ group (wherein the groups $R_1$ may be identical or different and may each represent a hydrogen atom, an alkyl, aralkyl, aryl or heteroaryl group), or by a $R_1NH—$ group substituted by an alkylcarbonyl, arylcarbonyl, aralkylcarbonyl, heteroarylcarbonyl, alkylsulphonyl, aralkylsulphonyl or arylsulphonyl group, and wherein, additionally, one or two —CH=CH— groups may each be replaced by a —CO—$NR_1$— group, a —CO—NH—, —NH—CO—, —CH=N— or —N=CH— group optionally substituted by $R_c$ or $R_d$, one of the groups $R_a$ to $R_d$ represents a group of the formula

A-B-C- wherein

A represents a straight-chained or branched $C_{1-5}$-aminoalkyl group, an amino, amidino or guanidino group, whilst in each of the above-mentioned groups, at one of the nitrogen atoms, one or two hydrogen atoms may be replaced by a $C_{1-4}$-alkyl group or a hydrogen atom may be replaced by a $C_{2-5}$-alkoxycarbonyl group, by an alkylcarbonyl, arylcarbonyl, aryloxycarbonyl or aralkoxycarbonyl group, or A represents a cyano group, a cyanoalkyl group having 1 to 4 carbon atoms in the alkyl moiety or, if A is bound to a nitrogen atom of groups B or C which is not part of a lactam group, it may also represent a hydrogen atom or an alkyl group, B represents a bond, an alkylene or alkenylene group, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, $(R_1)_2N—$, $(R_1)_2NCO—$, $(R_1)_2NSO_2—$ or nitro groups or by $R_1NH—$ groups substituted by an alkylcarbonyl, aralkylcarbonyl, arylcarbonyl, heteroarylcarbonyl, alkylsulphonyl, aralkylsulphonyl or arylsulphonyl group, whilst the substituents may be identical or different, a pyridinylene, pyrimidinylene, pyrazinylene or pyridazinylene group which may be substituted in the carbon skeleton by an alkyl group, whilst additionally one or two —CH=N— groups may each be replaced by a —CO—$NR_1$— group and one of the nitrogen atoms, instead of being bound to the group R1, may also be bound to the group C, provided that the latter does not adjoin the group B with a heteroatom or a carbonyl group, a $C_{3-5}$-cycloalkylene group, a cyclohexylene group wherein one or two CH moieties in the 1,4-position relative to each other may be replaced by nitrogen atoms, whilst additionally one or two of the methylene groups adjacent to a nitrogen atom may each be replaced by a carbonyl group, or a biphenylene group and C represents an alkylene or alkenylene group optionally substituted by a hydroxy group, an alkylenecarbonyl group connected to the group B via the carbonyl group, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, $(R_1)_2N—$, $(R_1)_2NCO—$, $(R_1)_2NSO_2—$ or nitro groups or by $R_1NH—$ groups substituted by an alkylcarbonyl, aralkylcarbonyl, arylcarbonyl, heteroarylcarbonyl, alkylsulphonyl, aralkylsulphonyl or arylsulphonyl group, the substituents being identical or different, an indanylene or 1,2,3,4-tetrahydronaphthylene group wherein, in each case, the saturated ring is bound to the group A and the aromatic ring is bound to the cyclic urea skeleton, a pyridinylene, pyrimidinylene, pyrazinylene or pyridazinylene group, each of which may be substituted in the carbon skeleton by an alkyl group, whilst additionally one or two —CH=N— groups may each be replaced by a —CO—$NR_1$— group and one of the nitrogen atoms, instead of being bound to the group $R_1$, may also be bound to the group B, provided that the latter does not represent a bond or is not adjacent to the group C with a heteroatom, a cyclohexylene group wherein one or two CH moieties in the 1,4-position relative to each other may be replacd by nitrogen atoms, whilst additionally one or two of the methylene groups adjacent to a nitrogen atom may each be replaced by a carbonyl group and the nitrogen atoms may not be bound to a nitrogen atom of the cyclic urea, a second of the groups $R_a$ to $R_d$ represents a group of the formula

F-E-D- wherein

D represents a $C_{1-5}$-alkylene group or a $C_{2-5}$-alkenylene group, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, carboxyalkoxy, alkoxycarbonylalkoxy, aralkoxycarbonyl-alkoxy, $(R_1)_2N$—, $(R_1)_2NCO$—, $(R_1)_2NSO_2$— or nitro groups or by $R_1NH$— groups substituted by an alkylcarbonyl, aralkylcarbonyl, arylcarbonyl, heteroarylcarbonyl, alkylsulphonyl, aralkylsulphonyl or arylsulphonyl group, the substituents being identical or different, a pyridinylene, pyrimidinylene, pyrazinylene or pyridazinylene group, each of which may be substituted by an alkyl group in the carbon skeleton, whilst additionally one or two —CH=N— groups may each be replaced by a —CO—NR₁— group and one of the nitrogen atoms instead of being bound to the group $R_1$ may also be bound to the group E, provided that the latter does not represent a bond or is not bound by a heteroatom to the group D, a cyclohexylene group wherein one or two CH moieties in the 1,4-position relative to each other may be replaced by nitrogen atoms, whilst additionally one or two of the methylene groups adjacent to a nitrogen atom may each be replaced by a carbonyl group, or a $C_{3-6}$-alkylene group interrupted by the group W, wherein W represents an oxygen or sulphur atom, a sulphinyl, sulphonyl, $R_1N$=, (alkylcarbonyl)N=, (aralkylcarbonyl)N=, (arylcarbonyl)N=, (heteroarylcarbonyl)N=, (alkylsulphonyl)N= or (arylsulphonyl)N= group and the alkylene group linked to a nitrogen atom of the cyclic urea contains 2 or 3 carbon atoms, E represents a bond, a $C_{1-5}$-alkylene group or a $C_{2-5}$-alkenylene group, each of which may be substituted by one or two alkyl groups, by a hydroxy, alkoxy, amino, alkylamino, aralkylamino, dialkylamino, bis(aralkyl)amino, carboxyalkyl, alkoxycarbonylalkyl or aralkoxycarbonylalkyl group, a phenylene group which may be mono- or disubstituted by fluorine, chlorine or bromine atoms, by $C_{1-4}$-alkyl groups, by trifluoromethyl, hydroxy, alkoxy, alkylsulphenyl, alkylsulphinyl, alkylsulphonyl, $(R_1)_2N$—, $(R_1)_2NCO$—, $(R_1)_2NSO_2$— or nitro groups or by $R_1$—NH— groups substituted by an alkylcarbonyl, aralkylcarbonyl, arylcarbonyl, heteroarylcarbonyl, alkylsulphonyl, aralkylsulphonyl or arylsulphonyl group, whilst the substituents may be identical or different, a pyridinylene, pyrimidinylene, pyrazinylene or pyridazinylene group, each of which may be alkyl-substituted in the carbon skeleton, whilst additionally one or two —CH=N— groups may each be replaced by a —CO—NR₁— group and one of the nitrogen atoms, instead of being bound to the group $R_1$, may also be bound to the group D, a cyclohexylene group wherein one or two CH moieties in the 1,4-position relative to each other may be replaced by nitrogen atoms, whilst additionally one or two of the methylene groups adjacent to a nitrogen atom may each be replaced by a carbonyl group, an alkylenearylene group linked to the group D via the aryl group or an alkylene group linked to the group D via the group W', wherein W' represents an oxygen or sulphur atom, a sulphinyl, sulphonyl, $R_1N$=, (alkycarbonyl)N=, (aralkylcarbonyl)N=, (arylcarbonyl)N=, (heteroarylcarbonyl)N=, (alkylsulphonyl)N=, (arylsulphonyl)N= or aminocarbonyl group wherein the nitrogen atom is bound to the alkylene group, F represents a carbonyl group which is substituted by a hydroxy or $C_{1-6}$-alkoxy group, whilst a $C_{1-3}$-alkoxy group may be substituted in the 1-, 2- or 3-position by an aryl or heteroaryl group or in the 2- or 3-position by a pyrrolidin-2-on-1-yl, morpholino, thiomorpholino or 1-oxido-thiomorpholino group, or F may represent a sulpho, phosphono, O-alkylphosphono or tetrazol-5-yl group, whilst if A represents a cyano group or an amino or aminoalkyl group optionally benzoylated or benzyloxy-carbonylated at the nitrogen atom, the shortest distance between the nitrogen atom of these groups and the group F being at least 10 bonds, the third of the groups $R_a$ to $R_d$ is a hydrogen atom, an alkyl, trifluoromethyl, aralkyl, aryl or heteroaryl group or, if the third of the groups $R_a$ to $R_d$ is bound to an unsaturated carbon atom of group Y, it may represent an alkoxy, alkylsulphenyl or $(R_1)_2N$— group and the fourth of groups $R_a$ to $R_d$ represents a hydrogen atom or an alkyl, aralkyl, aryl or heteroaryl group, particularly those compounds of general formula I wherein X represents a carbimino group optionally substituted at the nitrogen atom by a methyl, phenyl or pyridyl group, or represents a carbonyl, thiocarbonyl or sulphonyl group, Y represents a straight-chained alkylene or alkenylene group, each having 2 or 3 carbon atoms, optionally substituted by $R_c$ or $R_d$ or by $R_c$ and $R_d$, which may be substituted by a chlorine atom, by one or two methyl groups or by a trifluoromethyl, phenyl or acetyl group, whilst additionally a methylene group may be replaced by a carbonyl group, or Y represents a —CO—NH—, —NH—CO—, —CH=N— or —N=CH— group, optionally substituted by $R_c$ or $R_d$, or a 1,2-phenylene or 2,3-pyridinylene group, one of the groups $R_a$ to $R_d$ represents a group of formula

A-B-C- wherein

A represents a straight-chained or branched $C_{1-4}$-aminoalkyl group, an amino, amidino or guanidino group, whilst in each of the above-mentioned groups, at one of the nitrogen atoms, one or two hydrogen atoms may each be replaced by a $C_{1-4}$-alkyl group or a hydrogen atom may be replaced by an alkoxycarbonyl group having a total of 2 to 5 carbon atoms or by a benzyloxycarbonyl group, or, if A is bound to a nitrogen atom of group C which is not part of a lactam group, it may represent a hydrogen atom, B represents a bond, a phenylene group which may be substituted by one or two methyl groups, by a fluorine, chlorine or bromine atom, by a methoxy, methylsulphenyl, methylsulphinyl, methylsulphonyl, nitro, amino, acetylamino, benzoylamino or methanesulphonylamino group, a $C_{3-6}$-cycloalkylene group, a pyridinylene, pyrimidinylene, pyrazinylene, pyridazinylene or biphenylene group, C represents an ethylene group optionally substituted by a hydroxy group, a methylenecarbonyl group linked to the group B via the carbonyl group, a phenylene group which may be substituted by one or two methyl groups, by a fluorine, chlorine or bromine atom, by a methoxy, methylsulphenyl, methylsulphinyl, methylsulphonyl, nitro, amino, acetylamino, benzoylamino or methanesulphonylamino group, an indanylene or 1,2,3,4-tetrahydronaphthylene group wherein the saturated ring is bound to the group A and the aromatic ring is bound to the cyclic urea skeleton, a pyridinylene, pyrimidinylene, pyrazinylene, pyridazinylene, cyclohexylene or piperidinylene group, wherein the nitrogen atom may not be bound to a nitrogen atom of the cyclic urea, a second of groups $R_a$ to $R_d$ represents a group of formula

F-E-D- wherein D represents a $C_{1-4}$-alkylene group, a phenylene group which may be substituted by a fluorine, chlorine or bromine atom, by a methyl, methoxy, methylsulphenyl, methylsulphinyl, methylsulphonyl, carboxymethoxy, methoxycarbonyl-methoxy, nitro, amino, acetylamino, benzoylamino or methanesulphonylamino group, a pyridinylene, cyclohexylene or piperidinylene group, whilst additionally in a pyridinylene group a —CH=N— group may be replaced by a —CO—NH— group, whilst the nitrogen atom, instead of being bound to the hydrogen atom, may also be bound to the group E, provided that the latter is not a bond or is not bound by a heteroatom to group D, or a $C_{3-5}$-alkylene group interrupted by the group W, wherein W represents an oxygen or sulphur atom, a sulphinyl, sulphonyl, imino, methylimino, acetylimino, benzoylimino or methanesulphonylimino group and the alkylene group linked to the cyclic urea contains 2 or 3 carbon atoms, E represents a bond, a $C_{1-3}$-alkylene group optionally substituted by one or two methyl groups or by a hydroxy, methoxy, amino, dimethylamino, dibenzylamino, carboxymethyl or methoxycarbonylmethyl group or a $C_{2-3}$-alkenylene group, a phenylene group or a $C_{1-2}$-alkylene group linked to group D by the group W', wherein W' represents an oxygen or sulphur atom or a sulphinyl, sulphonyl or aminocarbonyl group, the amino group being bound to the alkylene group, and F represents a carbonyl group which is substituted by a hydroxy group, by a $C_{1-4}$-alkoxy group or by a phenylalkoxy group having 1 or 2 carbon atoms in the alkoxy moiety, or F represents a phosphono, O-methylphosphono or tetrazol-5-yl group, whilst if A represents an amino or aminoalkyl group optionally benzyloxycarbonylated at the nitrogen atom, the shortest distance between the nitrogen atom of this group and group F is at least 10 bonds, the third of the groups $R_a$ to $R_d$ represents a hydrogen atom, a methyl, ethyl, trifluoromethyl or phenyl group and the fourth of groups $R_a$ to $R_d$ represents a hydrogen atom or a methyl group, the tautomers, the stereoisomers, including the mixtures thereof, and the addition salts thereof.

Particularly preferred compounds of general formula I are those wherein

X represents a carbonyl or sulphonyl group,

Y represents a straight-chained alkylene or alkenylene group each having 2 or 3 carbon atoms, optionally substituted by $R_c$ or $R_d$ or by $R_c$ and $R_d$, which may be substituted by one or two methyl groups or by a trifluoromethyl or phenyl group, whilst additionally a methylene group may be replaced by a carbonyl group, or Y represents an —N=CH— or —CH=N— group optionally substituted by $R_c$ or $R_d$, one of the groups $R_a$ to $R_d$ represents a group of the formula

A-B-C- wherein

A represents a straight-chained or branched $C_{1-4}$-aminoalkyl group, an amino or amidino group, whilst in each of the above-mentioned groups, at one of the nitrogen atoms, a hydrogen atom may be replaced by an alkoxycarbonyl group having a total of 2 to 5 carbon atoms or by a benzyloxycarbonyl group, B represents a bond, a phenylene group which may be substituted by a fluorine or chlorine atom, a cyclopropylene, pyridinylene, pyrimidinylene, pyrazinylene or pyridazinylene group, C represents a phenylene group which may be substituted by one or two methyl groups, by a fluorine, chlorine or bromine atom, by a methoxy, methylsulphenyl, methylsulphinyl, methylsulphonyl, amino, acetylamino, benzoylamino or methanesulphonylamino group, or, if A represents an amino group and B represents a bond, an indanylene or 1,2,3,4-tetrahydronaphthylene group, wherein the saturated ring is bound to the group A and the aromatic ring is bound to the cyclic urea skeleton, a pyridinylene, pyrimidinylene, pyrazinylene, pyridazinylene, cyclohexylene or piperidinylene group, whilst the nitrogen atom may not be bound to a nitrogen atom of the cyclic urea, a second of the groups $R_a$ to $R_d$ represents a group of formula

F-E-D- wherein D represents a $C_{1-4}$-alkylene group, a phenylene group which may be substituted by a fluorine, chlorine or bromine atom or by a methyl, methoxy, methylsulphenyl, methylsulphinyl or methylsulphonyl group, a pyridinylene, cyclohexylene or piperidinylene group, whilst additionally in a pyridinylene group the —CH=N— group may be replaced by a —CO—NH— group and the nitrogen atom, instead of being bound to the hydrogen atom, may also be bound to the group E, provided that the latter is not a bond or is not bound to the group D by a heteroatom, or a —CH$_2$CH$_2$—N(COCH$_3$)—CH$_2$— group wherein the ethylene moiety is bound to the cyclic urea, E represents a bond, an ethylene group optionally substituted by one or two methyl groups or by an amino or dibenzylamino group, an ethenylene or phenylene group or a methylene group linked to group D by the group W', wherein W' represents an oxygen or sulphur atom or a sulphinyl or sulphonyl group, and F represents a carbonyl group which is substituted by a hydroxy group or by a $C_{1-4}$-alkoxy group, or F may represent a phosphono, O-methylphosphono or tetrazol-5-yl group, whilst if A represents an amino or aminoalkyl group optionally benzyloxycarbonylated at the nitrogen atom, the shortest distance between the nitrogen atom of this group and the group F is at least 10 bonds, the third of the groups $R_a$ to $R_d$ represents a hydrogen atom or a methyl, ethyl or phenyl group and the fourth of the groups $R_a$ to $R_d$ represents a hydrogen atom or a methyl group, the tautomers, the stereoisomers including the mixtures thereof and the addition salts thereof.

Most particularly preferred compounds of general formula I above are those wherein X represents a carbonyl or sulphonyl group, Y represents an ethylene or ethenylene group optionally substituted by $R_c$ or $R_d$ and optionally substituted by a methyl or phenyl group, or Y represents a carbonylmethylene or methylenecarbonyl group optionally substituted by a methyl group, or Y represents a —CH=N— or —N=CH— group optionally substituted by $R_c$ or $R_d$, one of the groups $R_a$ to $R_d$ represents a group of formula

A-B-C- wherein

A represents an aminomethyl or amidino group optionally substituted by an alkoxycarbonyl group with a total of 2 to 5 carbon atoms, B represents a bond or a 1,4-phenylene group and C represents a 1,4-phenylene group optionally substituted by a methyl group, 3,6-pyridazinylene or 1,4-piperidinylene group, whilst the nitrogen atom may not be bound to a nitrogen atom of the cyclic urea, or, if A represents an amino and B represents a bond, an indanylene group, wherein the saturated ring is attached to A and the aromatic ring to the cyclic urea ring, a second of the groups $R_a$ to $R_d$ represents a group of the formula

F-E-D- wherein D represents a $C_{1-4}$-alkylene group, a 1,4-phenylene or 1,4-cyclohexylene group, E represents a bond, an ethylene group optionally substituted by an amino or dibenzylamino group, an ethenylene group, a 1,4-phenylene group or a methylene group linked by the group W' to the group D, wherein W' represents an oxygen or sulphur atom or a sulphinyl or sulphonyl group, F represents a carbonyl group which is substituted by a hydroxy group or by a $C_{1-4}$-alkoxy group, whilst if A represents an aminomethyl group, the shortest distance between the nitrogen atom of this group and the group F is at least 10 bonds, the third of the groups $R_a$ to $R_d$ represents a hydrogen atom or a methyl, ethyl or phenyl group and the fourth of the groups $R_a$ to $R_d$ represents a hydrogen atom or a methyl group, particularly those compounds of general formula I wherein there is a further ring member between the linking points of those of groups $R_a$ to $R_d$ which represent the A-B-C- and F-E-D- groups, on the cyclic urea, the tautomers, the stereoisomers including mixtures thereof and the addition salts thereof.

The new compounds may, for example, be prepared by the following processes:

a) In order to prepare compounds of general formula I wherein F represents a carboxy group:

Converting a compound of general formula

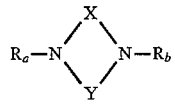

(II)

wherein $R_a$, $R_b$, X and Y are defined as hereinbefore with the proviso that one of the groups $R_a$ to $R_d$ must represent a group of formula

F-E-D- wherein E and D are as hereinbefore defined and F' represents a group which may be converted into a carboxyl group by hydrolysis, treatment with acids, thermolysis or hydrogenolysis, into a compound of general formula I wherein F represents a carboxyl group.

For example: functional derivatives of the carboxyl group such as the unsubstituted or substituted amides, esters, thioesters, trimethylsilylesters, orthoesters, iminoesters, amidines or anhydrides, or the nitrile group may be converted by hydrolysis into a carboxyl group; esters with tertiary alcohols, e.g. the tert.-butylester, may be converted by treatment with an acid or thermolysis into a carboxyl group; and esters with aralkanols, e.g. the benzylester, may be converted by hydrogenolysis into a carboxyl group.

The hydrolysis is expediently carried out either in the presence of an acid such as hydrochloric, sulphuric, phosphoric, trichloroacetic or trifluoroacetic acid, in the presence of a base such as lithium hydroxide, sodium hydroxide or potassium hydroxide in a suitable solvent such as water, water/methanol, water/ethanol, water/isopropanol, methanol, ethanol or water/dioxane at temperatures between −10° C. and 120° C., e.g. at temperatures between ambient temperature and the boiling temperature of the reaction mixture. In the case of treatment with an organic acid such as trichloroacetic or trifluoroacetic acid, any alcoholic hydroxy groups present may simultaneously be converted into a corresponding acyloxy group such as the trifluoroacetoxy group.

If F' in a compound of formula II represents a cyano or aminocarbonyl group, these groups may also be converted into the carboxyl group with a nitrite, e.g. sodium nitrite, in the presence of an acid such as sulphuric acid, which may expediently be used as solvent at the same time, at temperatures between 0° and 50° C.

If F' in a compound of formula II represents, for example, the tert.-butyloxycarbonyl group, the tert.-butyl group may also be cleaved by treatment with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between −10° and 120° C., e.g. at temperatures between 0° and 60° C., or thermally, optionally in an inert solvent such as methylene chloride, chloroform, benzene, toluene, tetrahydrofuran or dioxane and preferably in the presence of a catalytic quantity of an acid such as p-toluenesulphonic acid, sulphuric acid, phosphoric acid or polyphosphoric acid, preferably at the boiling temperature of the solvent used, e.g. at temperatures between 40° C. and 100° C.

If F' in a compound of formula II represents, for example, the benzyloxycarbonyl group, the benzyl group may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of from 1 to 5 bar. During hydrogenolysis, other groups may be reduced at the same time, e.g. a nitro group to the amino group or a benzyloxy group to the hydroxy group.

b) In order to prepare compounds of general formula I wherein A represents an H$_2$N—C(=NH)— group optionally substituted by an alkyl group:

Reaction of a compound of general formula

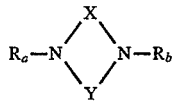

(III)

optionally formed in the reaction mixture,
wherein
R$_a$, R$_b$, X and Y are as hereinbefore defined, with the proviso that one of the groups R$_a$ to R$_d$ represents a group of the formula

Z$_1$-C(=NH)-B- wherein B and C are as hereinbefore defined and Z$_1$ represents an alkoxy or aralkoxy group such as a methoxy, ethoxy, n-propoxy, isopropoxy or benzyloxy group or an alkylthio or aralkylthio group such as a methylthio, ethylthio, n-propylthio or benzylthio group or an amino group, with an amine of general formula

R$_4$-NH$_2$ (IV)

wherein
R$_4$ represents a hydrogen atom or a C$_{1-4}$-alkyl group, or with the acid addition salts thereof.

The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as the corresponding ammonium carbonates, acetates or chlorides.

A compound of general formula III is obtained for example by reacting a corresponding nitrile with a corresponding alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0° and 50° C., but preferably at 20° C., or a corresponding nitrile with hydrogen sulphide, appropriately in a solvent such as pyridine or dimethylformamide and in the presence of a base such as triethylamine and subsequent alkylation of the thioamide formed with a corresponding alkyl or aralkyl halide, or by reacting a corresponding nitrile with an alkoxide such as sodium methoxide in a solvent such as dioxane or tetrahydrofuran, but preferably in the alcohol in question.

c) In order to prepare compounds of general formula I wherein at least one of groups B, C, D or E contains a sulphinyl or sulphonyl group:

Oxidation of a compound of general formula

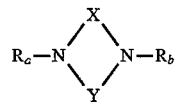

(V)

wherein
R$_a$, R$_b$, X and Y are as hereinbefore defined, with the proviso that at least one of the groups Y, B, C, D or E contains a sulphenyl or sulphinyl group.

The oxidation is preferably carried out in a solvent or mixture of solvents, e.g. in water, water/pyridine, acetone, methylene chloride, glacial acetic acid, glacial acetic acid/ acetic hydride, dilute sulphuric acid or trifluoroacetic acid, and depending on the oxidising agent used at temperatures between −80° and 100° C.

In order to prepare a corresponding S-oxide compound of general formula I the oxidation is conveniently carried out with one equivalent of the oxidizing agent used, eg. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid optionally in the presence of a weak base such as sodium acetate, with N-bromosuccinimide in ethanol, with tert.butyl hypochlorite in methanol at −80° to −30° C., with iodobenzodichloride in aqueous pyridine at 0° to 50° C., with nitric acid in glacial acetic acid at 0 to 20° C., with chromic acid in glacial acetic acid or in acetone at 0° to 20° C. and with sulphuryl chloride in methylene chloride at −70° C., with the thioether-chlorine complex so obtained conveniently being hydrolysed with aqueous ethanol.

In order to prepare an S,S-dioxide compound of general formula I the oxidation is conveniently carried out, starting from a corresponding alkylsulphinyl compound, with one or more equivalents of the oxidising agent used, or starting from a corresponding alkylsulphenyl compound with two or more equivalents of the oxidising agent used, e.g. with hydrogen peroxide in glacial acetic acid/acetic anhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures between 0° and 60° C., with nitric acid in glacial acetic acid at 0° to 20° C., with chromic acid or potassium permanganate in glacial acetic acid, water/sulphuric acid or in acetone at 0° to 20° C.

d) In order to prepare compounds of general formula I wherein Y represents a straight-chained $C_{2-4}$-alkylene group, optionally substituted by $R_c$ or $R_d$ or by $R_c$ and $R_d$, which may be mono- or disubstituted by alkyl, trifluoromethyl, aralkyl, aryl or heteroaryl groups:

Hydrogenation of a compound of general formula

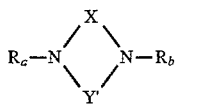

(VI)

wherein $R_a$, $R_b$ and X are as hereinbefore defined and Y' represents a straight-chained $C_{2-4}$-alkenylene group, optionally substituted by $R_c$ or $R_d$ or by $R_c$ and $R_d$, which may be mono- or disubstituted by alkyl, trifluoromethyl, aralkyl, aryl or heteroaryl groups.

The hydrogenation is carried out in a solvent such as methanol, ethanol, ethyl acetate or glacial acetic acid, optionally with the addition of an acid such as hydrochloric acid, with hydrogen in the presence of a catalyst such as palladium/charcoal or platinum, at temperatures between 0° and 100° C., but preferably between 20° and 50° C., and under a hydrogen pressure of 1 to 7 bar, but preferably from 3 to 5 bar.

e) In order to prepare compounds of general formula I wherein A represents an aminoalkyl, amidino or guanidino group substituted by an alkoxycarbonyl group having a total of 2 to 5 carbon atoms or by an aralkoxycarbonyl, aryloxycarbonyl, alkylcarbonyl or arylcarbonyl group:

Reaction of a compound of general formula

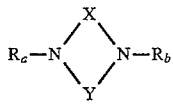

(VII)

wherein $R_a$, $R_b$, X and Y are as hereinbefore defined with the proviso that one of the groups $R_a$ to $R_d$ represents a group of formula

A'-B-C- wherein

B and C are as hereinbefore defined and A' represents an $H_2N$—$C_{1-5}$alkyl—, $H_2N$—C(=NH)— or $H_2N$—C(=NH)—NH— group, with a compound of general formula $Z_2$-$R_5$ (VIII)

wherein $R_5$ represents an alkoxycarbonyl group having a total of 2 to 5 carbon atoms, an aralkoxycarbonyl, aryloxycarbonyl, alkylcarbonyl or arylcarbonyl group and $Z_2$ represents a nucleophilic leaving group such as a halogen atom, e.g. a chlorine or bromine atom, or an aryloxy, arylthio, alkoxycarbonyloxy, aralkoxycarbonyloxy or imidazolyl group.

The acylation is conveniently carried out in a solvent such as tetrahydrofuran, methylene chloride, chloroform, dimethylformamide, water or mixtures of these solvents, optionally in the presence of a base such as sodium carbonate, potassium carbonate or sodium hydroxide solution or in the presence of a tertiary organic base such as triethylamine, N-ethyl-diisopropylamine, N-methylmorpholine or pyridine, which may simultaneously serve as solvents, at temperatures between −30° and 100° C., but preferably at temperatures between −10° and 80° C.

f) In order to prepare compounds of general formula I wherein F represents a carbonyl group substituted by a $C_{1-6}$-alkoxy group, wherein an alkoxy group with 1 to 3 carbon atoms may be substituted in the 1-, 2- or 3-position by an aryl or heteroaryl group or in the 2- or 3-position by a pyrrolidin-2-on-1-yl, morpholino, thiomorpholino or 1-oxido-thiomorpholino group:

Reacting a compound of general formula

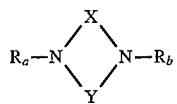

(IX)

wherein $R_a$, $R_b$, X and Y are as hereinbefore defined, with the proviso that one of the groups $R_a$ to $R_d$ represents a group of formula

F"-E-D- wherein

E and D are as hereinbefore defined and F" represents a carboxy or alkoxycarbonyl group, with an alcohol of general formula

HO-$R_6$ (X)

wherein $R_6$ represents a $C_{1-6}$-alkyl group which may be substituted in the 1-, 2- or 3-position by an aryl or heteroaryl group or in the 2- or 3-position by a pyrrolidin-2-on-1-yl, morpholino, thiomorpholino or 1-oxido-thiomorpholino group.

The reaction is expediently carried out in a solvent or mixture of solvents such as methylene chloride, dimethylformamide, dimethylsulphoxide, benzene, toluene, chlorobenzene, tetrahydrofuran, benzene/tetrahydrofuran or dioxane, optionally in the presence of an acid such as hydrochloric acid or in the presence of a dehydrating agent, e.g. in the presence of isobutylchloroformate, thionylchloride, trimethylchloro-silane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/ N-hydroxysuccinimide or 1-hydroxy-benzotriazole and optionally also in the presence of 4-dimethylamino-pyridine, N,N'-carbonyldiimidazole or N,N'-thionyl-diimidazole or triphenylphosphine/carbon tetrachloride, conveniently at temperatures between 0° and 150° C., preferably at temperatures between 0° and 50° C.

The reaction of a corresponding alkoxy compound with an alcohol of general formula X is preferably carried out in a corresponding alcohol as solvent, optionally in the presence of an additional solvent such as methylene chloride or ether, preferably in the presence of an acid such as hydrochloric acid at temperatures between 0° and 100° C., preferably at temperatures between 20 and 80° C.

g) In order to prepare compounds of general formula I wherein A represents an $NH_2$—C(=NH)— group and B or, if B represents a bond, C represents a $C_{4-5}$-cycloalkylene group, optionally substituted by an alkyl, aralkyl or aryl group, wherein a CH moiety is replaced by a nitrogen atom, or a $C_{6-7}$-cycloalkylene group, optionally substituted by an alkyl, aralkyl or aryl group, wherein one or two CH moieties in the 1,4-position relative to each other are each replaced by a nitrogen atom, whilst B or, if B is a bond, C is linked to the group A via one of the above-mentioned nitrogen atoms:

Reacting a compound of general formula

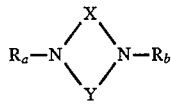
(XI)

wherein $R_a$, $R_b$, X and Y are as hereinbefore defined, with the proviso that one of the groups $R_a$ to $R_d$ represents a group of formula H-B'-C- or H-C'- wherein

C is as hereinbefore defined and B' or C' represents a $C_{4-5}$-cycloalkylene group, optionally substituted by an alkyl, aralkyl or aryl group, wherein a CH moiety is replaced by a nitrogen atom, or a $C_{6-7}$-cycloalkylene group, optionally substituted by an alkyl, aralkyl or aryl group, wherein one or two CH moieties in the 1,4-position relative to each other are each replaced by a nitrogen atom, the hydrogen atom being linked to a nitrogen atom of the group B' or C', with a compound of general formula $Z_3$—C(=NH)—$NH_2$   (XII)

wherein $Z_3$ represents a nucleophilic leaving group such as an alkoxy or alkylthio group, e.g. a methylthio or ethylthio group.

The reaction is conveniently carried out in a solvent or mixture of solvents such as dimethylformamide, dimethylsulphoxide, benzene, toluene, chlorobenzene, tetrahydrofuran, benzene/tetrahydrofuran or dioxane, preferably in the presence of an acid-binding agent, e.g. an alkoxide such as potassium tert.-butoxide, an alkali metal hydroxide such as sodium or potassium hydroxide, an alkali metal carbonate such as sodium carbonate or potassium carbonate or an alkali metal hydride such as sodium hydride, conveniently at temperatures between 50° and 150° C., preferably at temperatures between 75° and 125° C.

h) In order to prepare compounds of general formula I, wherein A represents an $H_2N$—$CH_2$—V— group, wherein V represents a bond or a straight-chained or branched $C_{1-4}$-alkylene group:

Reduction of a compound of general formula

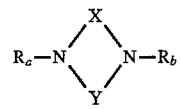
(XIII)

wherein $R_a$, $R_b$, X and Y are as hereinbefore defined with the proviso that one of the groups $R_a$ to $R_d$ represents a group of the formula

NC-V-B-C- wherein

B and C are as hereinbefore defined and V represents a bond or a straight-chained or branched $C_{1-4}$-alkylene group.

The reduction is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid, in the presence of catalytically activated hydrogen, e.g. hydrogen in the presence of Rney nickel, platinum or palladium/charcoal, or in the presence of a metal hydride such as sodium borohydride, lithium borohydride or lithium aluminium hydride, at temperatures between 0° and 100° C., preferably at temperatures between 20° and 80° C.

i) In order to prepare compounds of general formula I wherein C represents an alkylene group substituted by a hydroxy group:

Reduction of a compound of general formula

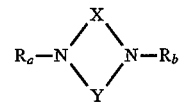
(XIV)

wherein $R_a$, $R_b$, X and Y are as hereinbefore defined, with the proviso that one of the groups $R_a$ to $R_d$ represents a group of the formula

A-B-C"- wherein

A and B are as hereinbefore defined and C" represents an alkylene group wherein a methylene group is replaced by a carbonyl group.

The reduction is preferably carried out in a suitable solvent such as methanol, methanol/water, ethanol, ether, tetrahydrofuran, dioxane or glacial acetic acid, in the presence of catalytically activated hydrogen, e.g. hydrogen in the presence of platinum or palladium/charcoal, or in the presence of a metal hydride such as sodium borohydride, lithium borohydride or lithium aluminium hydride, at temperatures between −5° and 20° C., preferably at temperatures between 0° and 10° C.

j) In order to prepare compounds of general formula I wherein A represents an $H_2N$—C(=NH)—NH— group:

Reacting a compound of general formula

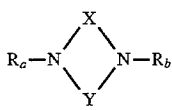 (XV)

wherein $R_a$, $R_b$, X and Y are as hereinbefore defined with the proviso that one of the group $R_a$ to $R_d$ represents a group of the formula

wherein

B and C are as hereinbefore defined, with cyanamide or an acid addition salt thereof or with an S-alkyl-isothiourea, O-methylisothiourea or 1-amidino-3,5-dimethylpyrazole.

The reaction is conveniently carried out in a solvent such as dioxane, dioxane/water or tetrahydrofuran, preferably at temperatures between 60° and 120° C., e.g. at the boiling temperature of the reaction mixture.

k) Cyclising a compound of general formula

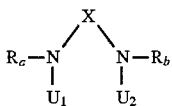 (XVI)

wherein $R_a$, $R_b$ and X are as hereinbefore defined, one of the groups $U_1$ or $U_2$ represents a hydrogen atom and the other group $U_1$ or $U_2$ represents a group of the formula

wherein

Y" represents a straight-chained alkylene or alkenylene group each having 2 to 4 carbon atoms, optionally substituted by $R_c$ or $R_d$ or by $R_c$ and $R_d$, wherein each carbon atom may be mono- or disubstituted by an alkyl, trifluoromethyl, aralkyl, aryl, heteroaryl or alkylcarbonyl group, whilst the substituents may be identical or different, or Y" represents a 1,2-cycloalkylene group having 4 to 7 carbon atoms optionally substituted by $R_c$ or $R_d$ or by $R_c$ and $R_d$, or Y" represents a 1,2-cycloalkenylene group having 4 to 7 carbon atoms, a —CH=N— group optionally substituted by the groups $R_c$ or $R_d$, wherein the nitrogen atom is linked to one of the nitrogen atoms in formula XVI, or a —CH$_2$—NH— group optionally substituted by $R_c$ or $R_d$ and $Z_4$ represents a nucleophilic leaving group such as a halogen atom, a hydroxy, alkoxy or sulphonic acid ester group, e.g. a chlorine, bromine or iodine atom, a methoxy, ethoxy, isopropyloxy, methanesulphonyloxy or p-toluenesulphonyloxy group, or, together with an adjacent methylene group of the group Y", $Z_4$ represents a carbonyl, carboxy, alkoxycarbonyl, aralkoxycarbonyl, aryloxycarbonyl or dialkoxymethyl group.

The reaction is preferably carried out in a solvent such as ethanol, isopropanol, methylene chloride, dioxane, toluene, dimethylformamide or dimethyl-sulphoxide, optionally in the presence of a base such as pyridine, an acid such as hydrochloric, sulphuric, polyphosphoric or trifluoroacetic acid, and a dehydrating agent such as N,N'-dicyclohexylcarbodiimide, at temperatures between 20° and 200° C. However, the reaction may also be carried out without a solvent.

If $Z_4$ represents a nucleophilic leaving group such as a halogen atom or a sulphonic ester group, the reaction is preferably carried out in the presence of a base such as potassium carbonate, sodium hydride or potassium tert.butoxide, at temperatures between 20° and 60° C., if the group $Z_4$ represents a hydroxy or alkoxy group or together with an adjacent methylene group of the group Y" represents a carbonyl, carboxy, alkoxycarbonyl, aralkoxycarbonyl, aryloxycarbonyl or dialkoxymethyl group, the reaction is preferably carried out in the presence of an acid such as hydrochloric or trifluoroacetic acid, which may simultaneously serve as solvent, at temperatures between 20° and 80° C., or in the melt at temperatures between 50° and 250° C., preferably at temperatures between 100° and 200° C.

l) In order to prepare compounds of general formula I wherein $R_a$ or $R_c$ represents an E-F-D- group:

Cyclising a compound of general formula

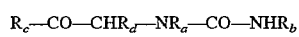 (XVII)

optionally formed in the reaction mixture, wherein $R_a$ to $R_d$ are as hereinbefore defined, optionally with subsequent hydrogenation.

The cyclisation is preferably carried out in a solvent such as water, ethanol/water, ethanol, benzene, toluene or dioxane and conveniently in the presence of a base such as pyridine, which may also serve as solvent, at elevated temperatures, e.g. at the boiling temperature of the solvent used.

The optional subsequent hydrogenation is preferably carried out using hydrogen in the presence of a catalyst such as palladium/charcoal or platinum, in a solvent such as methanol, ethanol, ethyl acetate or glacial acetic acid, optionally with the addition of an acid such as hydrochloric acid, at temperatures between 0° and 50° C., but preferably at ambient temperature, and under a hydrogen pressure of 1 to 7 bar, preferably 3 to 5 bar.

m) In order to prepare compounds of general formula I wherein X represents a carbonyl group:

Reacting a compound of general formula

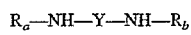 (XVIII)

wherein $R_a$, $R_b$ and Y are as hereinbefore defined, with a compound of general formula

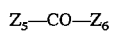 (XIX)

wherein $Z_5$ and $Z_6$, which may be identical or different, represent nucleophilic leaving groups such as halogen atoms, alkoxy or aryloxy groups, e.g. they each represent a chlorine atom or a methoxy, ethoxy or phenyloxy group.

The reaction is preferably carried out in a solvent such as methylene chloride, chloroform, toluene or dioxane, optionally in the presence of a base such as triethylamine or pyridine at temperatures between 0° and 50° C., preferably at ambient temperature.

n) In order to prepare compounds of general formula I wherein $R_a$ to $R_d$ are defined as hereinbefore, with the proviso that at least one of the groups $R_a$ and $R_b$ does not represent a hydrogen atom:

Reacting a compound of general formula

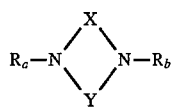 (XX)

wherein

X and Y are as hereinbefore defined, one of the groups $R_a$ or $R_b$ represents a hydrogen atom and the other group $R_a$ or $R_b$ is as hereinbefore defined, with a compound of general formula $$Z_7\text{—R'} \quad (XXI)$$

wherein

R' has the meanings given hereinbefore for $R_a$ or $R_b$, with the exception of a hydrogen atom, and $Z_7$ represents a nucleophilic leaving group such as a halogen atom or a sulphonic acid ester group, e.g. a chlorine, bromine or iodine atom or a methane-sulphonyloxy or p-toluenesulphonyloxy group or, if $R_a$ or $R_b$ represents a —D—COO-alkyl group, with the proviso that there are two carbon atoms between the nitrogen atom of the cyclic urea and the alkoxycarbonyl group, reacting with a compound of general formula $$\text{-D'-COO-alkyl} \quad (XXII)$$

wherein

D' has the meanings given for D hereinbefore, with the proviso that the alkoxycarbonyl group immediately precedes a carbon-carbon double or triple bond.

The alkylation is expediently carried out in a solvent or mixture of solvents such as methylene chloride, dimethylformamide, dimethylsulphoxide, benzene, toluene, chlorobenzene, tetrahydrofuran, benzene/tetrahydrofuran or dioxane, preferably in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride or a tertiary organic base such as ethyl-diisopropylamine, conveniently at temperatures between 0° and 150° C., preferably at temperatures between 0° and 50° C.

The arylation is expediently carried out with an aryl compound of general formula XXI wherein $Z_7$ represents an iodine atom, preferably in a solvent such as toluene or xylene, and preferably in the presence of one or more reaction accelerators such as tris-[2-(2-methoxy-ethoxy) ethyl]amine, copper(I)chloride or copper(II)chloride, at elevated temperatures, e.g. at temperatures between 100° and 200° C., but preferably at the boiling temperature of the reaction mixture. However, the reaction may also be carried out without a solvent.

The addition of an alkenyl compound of general formula XXII is preferably carried out in a solvent such as dimethylformamide and in the presence of a base such as sodium hydride, at temperatures between 0° and 50° C., preferably at ambient temperature.

o) In order to prepare compounds of general formula I wherein F represents a carboxy, alkoxycarbonyl, aralkoxycarbonyl or aryloxycarbonyl group:

Oxidation of a compound of general formula

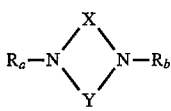 (XXIII)

wherein $R_a$, $R_b$, X and Y are as hereinbefore defined, with the proviso that one of the groups $R_a$ to $R_d$ represents a group of the formula $$CH_2\text{=CH-E-D-}$$

where E and D are as hereinbefore defined, with optional subsequent esterification.

The oxidation is carried out in a solvent such as methylene chloride, acetonitrile, acetonitrile/water, methylene chloride/acetonitrile/water or carbon tetrachloride/acetonitrile/water, in the presence of an oxidising agent such as potassium permanganate or ruthenium tetroxide, the ruthenium tetroxide preferably being formed in the reaction mixture by reacting a ruthenium salt such as ruthenium trichloride with an oxidising agent such as sodium periodate, at temperatures between –10° and 50° C., preferably at temperatures between 15° and 30° C.

The optional subsequent esterification is expediently carried out in a suitable solvent, e.g. in a corresponding alcohol, pyridine, toluene, methylene chloride, tetrahydrofuran or dioxane, in the presence of an acid activating and/or dehydrating agent such as hydrogen chloride, concentrated sulphuric acid, thionyl chloride, ethylchloroformate, carbonyldiimidazole or N,N'-dicyclohexylcarbodiimide or the isourea esters thereof, optionally in the presence of a reaction accelerator such as copper chloride, or by transesterification, e.g. with a corresponding carbonic acid diester, at temperatures between 0° and 100° C., but preferably at temperatures between 20° C. and the boiling temperature of the solvent in question.

p) In order to prepare compounds of general formula I wherein F represents an O-alkyl-phosphono group:
Reacting a compound of general formula

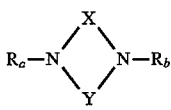 (XXIV)

wherein $R_a$, $R_b$, X and Y are as hereinbefore defined, with the proviso that F represents a dialkoxyphosphoryl group, with an alkali metal iodide.

The reaction is preferably carried out in a solvent such methylethylketone, in the presence of an alkali metal iodide such as sodium iodide, at temperatures between 25° and 100° C., preferably at the boiling temperature of the reaction mixture.

q) In order to prepare compounds of general formula I wherein F represents a phosphono group:
Reacting a compound of general formula

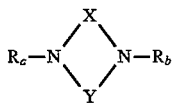 (XXV)

wherein $R_a$, $R_b$, X and Y are as hereinbefore defined, with the proviso that F represents an O-alkylphosphono- or dialkoxyphosphoryl group, with an alkali metal iodide in the presence of a trialkylhalosilane.

The reaction is preferably carried out in a solvent such as acetonitrile, in the presence of an alkali metal iodide such as sodium iodide, and a trialkylhalosilane such as trimethylchlorosilane, at temperatures between 25° and 80° C., but preferably at temperatures between 30° and 50° C.

r) In order to prepare compounds of general formula I wherein W represents an $R_1N$— group:
Reacting a compound of general formula

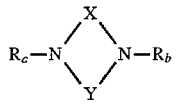
(XXVI)

wherein $R_a$, $R_b$, X and Y are as hereinbefore defined, with the proviso that one of the groups $R_a$ to $R_d$ represents a $Z_8$—D"— group, wherein D" represents a $C_{1-3}$-alkylene group and $Z_8$ represents a nucleophilic leaving group such as a halogen atom or a sulphonic acid ester group, e.g. a chlorine, bromine or iodine atom or a methane-sulphonyloxy or p-toluenesulphonyloxy group, with a compound of general formula $R_1NH-E'-F$   (XXVII)

wherein

F and $R_1$ are as hereinbefore defined and E' represents a $C_{1-3}$-alkylene group.

The reaction is expediently carried out in a solvent or mixture of solvents such as methylene chloride, dimethylformamide, dimethylsulphoxide, benzene, toluene, chlorobenzene, tetrahydrofuran, benzene/tetrahydrofuran or dioxane, preferably in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride or a tertiary organic base such as ethyl diisopropylamine, conveniently at temperatures between 0° and 150° C., preferably at temperatures between 0° and 50° C.

s) In order to prepare compounds of general formula I wherein A represents an amino or aminoalkyl group:
Reacting a compound of general formula

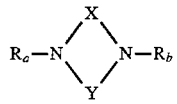
(XXVIII)

wherein $R_a$, $R_b$, X and Y are as hereinbefore defined, with the proviso that one of the groups $R_a$ to $R_d$ represents an $H_2N$—CO—T—B—C— group, where B and C are as hereinbefore defined and T represents a bond or a $C_{1-5}$-alkylene group, with a phenyl iodine(III) compound of general formula

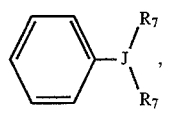
(XXIX)

wherein $R_7$ represents an acyl group or an organic carboxylic acid such as the acetoxy or trifluoroacetoxy group.

The-reaction is preferably carried out in an aqueous solvent such as water or water/acetonitrile, at temperatures between 0° and 50° C., but preferably at ambient temperature.

t) In order to prepare compounds of general formula I wherein A represents an amino or aminoalkyl group substituted by one or two alkyl groups at the nitrogen atom:
Reacting a compound of general formula

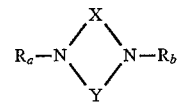
(XXX)

wherein $R_a$, $R_b$, X and Y are as hereinbefore defined, with the proviso that one of the groups $R_a$ to $R_d$ represents a group of the formula

A"-B-C- wherein

B and C are as hereinbefore defined and A" represents an amino, alkylamino, aminoalkyl or alkylaminoalkyl group, with a compound of general formula $Z_9$—($R_8$—C—$R_9$)—$Z_{10}$   (XXXI)

wherein $R_8$ and $R_9$, which may be identical or different, represent hydrogen atoms or alkyl groups, one of the groups $Z_9$ or $Z_{10}$ represents a nucleophilic leaving group such as a halogen atom, e.g. a chlorine, bromine or iodine atom, or a sulphonic acid ester group, e.g. a methanesulphonyloxy or p-toluenesulphonyloxy group, and the other group $Z_9$ or $Z_{10}$ represents a hydrogen atom or analkyl group or $Z_9$ and $Z_{10}$ together represent an oxygen atom.

The alkylation with a compound of formula XXXI wherein $Z_9$ or $Z_{10}$ represents a nucleophilic leaving group is conveniently carried out in a solvent such as tetrahydrofuran, dioxane, dimethylsulphoxide or dimethylformamide, optionally in the presence of a base such as sodium carbonate, potassium carbonate or sodium hydroxide solution or in the presence of a tertiary organic base such as N-ethyl-diisopropylamine or N-methylmorpholine, which may be simultaneously serve as solvent, at temperatures between –30° and 100° C., but preferably at temperatures between –10° and 80° C.

The alkylation with a carbonyl compound of general formula XXXI is preferably carried out in the presence of a complex metal hydride such as sodium borohydride, lithium borohydride or sodium cyanoborohydride, conveniently at a pH of 6 to 7 and at ambient temperature or in the presence of a hydrogenation catalyst, e.g. with hydrogen in the presence of palladium/charcoal, at a hydrogen pressure of 5 bar.

u) In order to prepare compounds of general formula I wherein A represents a cyano group:
Reacting a compound of general formula

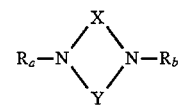
(XXXII)

wherein $R_a$, $R_b$, X and Y are defined as hereinbefore, with the proviso that one of the groups $R_a$ to $R_d$ represents a group of the formula

A'''-B-C- wherein

B and C are as hereinbefore defined and A''' represents a halogen atom, e.g. a bromine or iodine atom, with copper(I)cyanide.

The reaction is preferably carried out in a solvent such as dimethylformamide, dimethylacetamide or N-methylpyrrolidone, at temperatures between 100° and 250° C., preferably between 150° C. and the boiling temperature of the reaction mixture.

v) In order to prepare compounds of general formula I wherein A represents an aminoalkyl group where the amino group is not bound to a quaternary carbon atom, or an amino group which is bound to a CH— or CH$_2$ group of group B or C:

Reduction of a compound of general formula

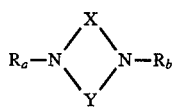 (XXXIII)

wherein

R$_a$, R$_b$, X and Y are as hereinbefore defined, with the proviso that one of the groups R$_a$ to R$_d$ represents a group of the formula

A''''-B-C- wherein

B and C are as hereinbefore defined and A'''' contains an N-hydroxy-imino group.

The reduction is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid, in the presence of catalytically activated hydrogen, e.g. hydrogen in the presence of Rney nickel, platinum or palladium/charcoal, at temperatures between 0° and 100° C., preferably at temperatures between 20° and 80° C.

If according to the invention a compound of general formula I is obtained, this may be converted by bromination into a corresponding bromine compound of general formula I or if a compound of general formula I is obtained, this may be converted by nitrogenation into a corresponding nitro compound of general formula I or if a compound of general formula I is obtained which contains a nitro group, this may be converted by reduction into a corresponding amino compound or if a compound of general formula I is obtained which contains an R$_1$NH— group or wherein W represents an imino group, this may be converted by acylation or sulphonation into a corresponding compound of general formula I which contains an R$_1$NH— group substituted by an alkylcarbonyl, aralkylcarbonyl, arylcarbonyl, heteroarylcarbonyl, alkylsulphonyl, aralkylsulphonyl or arylsulphonyl group, or if a compound of general formula I is obtained wherein X represents a carbonyl group, this may be converted by means of a sulphurising agent into a corresponding thiocarbonyl compound.

The subsequent bromination is preferably carried out in a solvent such as glacial acetic acid, with a brominating agent such as bromine, at temperatures between 0° and 40° C., preferably at ambient temperature.

The subsequently nitrogenation is carried out with a nitrogenating agent such as concentrated sulphuric acid/nitric acid or fuming nitric acid, which may conveniently serve as solvents, optionally in a solvent such as nitrobenzene, at temperatures between 0° and 50° C., preferably at ambient temperature.

The subsequent reduction of the nitro group is preferably carried out in a solvent such as water, water/ethanol, methanol, glacial acetic acid, ethyl acetate or dimethylformamide, expediently with hydrogen in the presence of a hydrogenation catalyst such as Rney nickel, platinum or palladium/charcoal, with metals such as iron, tin or zinc in the presence of an acid such as zinc/acetic acid or zinc/calcium chloride, with salts such as iron(II)sulphate, tin(II)chloride, sodium sulphide, sodium hydrogen sulphite or sodium dithionite, or with hydrazine in the presence of Rney nickel, at temperatures between 0° and 100° C., but preferably at temperatures between 20° and 80° C.

The subsequent acylation or sulphonylation of an R$_1$—NH— group is expediently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, optionally in the presence of an inorganic base such as sodium carbonate or a tertiary organic base such as triethylamine, pyridine or 4-dimethylaminopyridine, which may simultaneously be used as solvent, at temperatures between −25° and 150° C., but preferably at temperatures between −10° C. and the boiling temperature of the solvent used. However, the subsequent acylation or sulphonylation is preferably carried out with a corresponding acid halide or acid anhydride, as described hereinbefore, and this may also be carried out without a solvent.

The reaction is carried out with a sulphurising agent such as phosphorus pentasulphide or 2,4-bis-(4-methoxyphenyl)-1,3-di-thia-2,4-diphosphetan-2,4-disulphide, expediently in a solvent such as pyridine, toluene or xylene, at temperatures between 50° and 150° C., e.g. at the boiling temperature of the reaction mixture.

In reactions a) to v) described above and in the subsequent reactions, any reactive groups present such as hydroxy, carboxy, amino, alkylamino or imino groups, may optionally be protected during the reaction by means of conventional protecting groups which are cleaved again after the reaction.

For example, a suitable protective group for a hydroxy group might be a trimethylsilyl, acetyl, benzoyl, tert.-butyl, trityl, benzyl or tetrahydropyranyl group, whilst protective groups for a carboxyl group might be the trimethylsilyl, methyl, ethyl, tert.-butyl, benzyl or tetrahydropyranyl group, and protecting groups for an amino, alkylamino or imino group might be the acetyl, benzoyl, ethoxycarbonyl, tert.-butoxycarbonyl, benzyloxycarbonyl, benzyl, methoxybenzyl or 2,4-dimethoxybenzyl group and an additional protecting group for the amino group might be the phthalyl group.

The optional subsequent cleaving of a protecting group is carried out, for example, hydrolytically in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide, or by ether cleavage, e.g. in the presence of iodotrimethylsilane, at temperatures between 0° and 100° C., preferably at temperatures between 10° and 50° C.

However, a benzyl, methoxybenzyl or benzyloxycarbonyl group is cleaved, for example, by hydrogenelysis, e.g. with hydrogen in the presence of a catalyst such as palladium/charcoal, in a solvent such as methanol, ethanol, ethyl acetate or glacial acetic acid, optionally with the addition of an acid such as hydrochloric acid, at temperatures between 0° and 50° C., but preferably at ambient temperature, under a hydrogen pressure of from 1 to 7 bar, but preferably from 3 to 5 bar.

The cleaving of a methoxybenzyl group may also be carried out in the presence of an oxidising agent such as Ce(IV)ammonium nitrate, in a solvent such as methylene chloride, acetonitrile or acetonitrile/water, at temperatures between 0° and 50° C., but preferably at ambient temperature.

However, a 2,4-dimethoxybenzyl group is preferably cleaved in trifluoroacetic acid in the presence of anisole.

A tert.-butyl or tert.-butyloxycarbonyl group is preferably cleaved by treatment with an acid such as trifluoroacetic or hydrochloric acid, optionally using a solvent such as methylene chloride, dioxane or ether.

The cleaving of a phthalyl group is preferably carried out in the presence of hydrazine or a primary amine such as methylamine, ethylamine or n-butylamine in a solvent such as methanol, ethanol, isopropanol, toluene/water or dioxane, at temperatures between 20° and 50° C.

Moreover, the compounds of general formula I obtained may, as already mentioned hereinbefore, be resolved into the enantiomers and/or diastereomers thereof. Thus, for example, cis/trans mixtures may be resolved into their cis and trans isomers and compounds having at least one optically active carbon atom may be resolved into their enantiomers.

Thus, for example, the cis/trans mixtures obtained may be separated by chromatography into their cis and trans isomers, the compounds of general formula I obtained in the form of racemates may be separated by known methods (see Allinger N. L. and Eliel E. L. in "Topics in Stereochemistry", Vol. 6, Wiley Interscience, 1971) into their optical antipodes and compounds of general formula I having at least 2 asymmetric carbon atoms can be separated on the basis of their physical-chemical differences into their diastereomers by methods known per se, e.g. by chromatography and/or fractional crystallisation, and if these diastereomers are obtained in racemic form they may subsequently be separated into the enantiomers as mentioned above.

Enantiomer separation is preferably achieved by column separation on chiral phases or by recrystallisation from an optically active solvent or by reacting with an optically active substance which forms salts or derivatives such as esters or amides with the racemic compound, more particularly acids and their activated derivatives or alcohols, and separating the diastereomeric salt mixture obtained in this way, e.g. on the basis of different solubilities, whilst the free antipodes may be liberated from the pure diastereomeric salts by the action of suitable agents. Particularly common optically active acids are, for example, the D and L forms of tartaric or dibenzoyltartaric acid, di-o-tolyl-tartaric acid, malic, mandelic and camphorsulphonic acid, glutamic acid, aspartic acid or quinic acid. An optically active alcohol might be, for example, (+)- or (−)-menthol and an optically active acyl group in amides might be (+) or (−)-menthyloxycarbonyl.

Moreover, the compounds of formula I obtained may be converted into the acid addition salts thereof, more particularly for pharmaceutical use the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid and maleic acid.

In addition, the new compounds of formula I thus obtained, should they contain a carboxyl group, may if desired subsequently be converted into the addition salts thereof with inorganic or organic bases, more particularly for pharmaceutical use into the physiologically acceptable addition salts thereof. Examples of suitable bases include sodium hydroxide, potassium hydroxide, cyclohexylamine, ethanolamine, diethanolamine and triethanolamine.

The compounds used as starting materials are known from the literature in some cases or may be obtained by methods known from the literature (see the Examples), e.g. by the methods described in published German patent applications DE-A-4035961 and DE-A-4102024.

For example, the cyclic urea derivatives are obtained by cyclising a correspondingly substituted urea which in turn is obtained by known methods, or by reacting a correspondingly substituted diamine with phosgene and optionally subsequently introducing sulphur and oxidising the resulting thio compound.

As already mentioned hereinbefore, the new cyclic urea derivatives of general formula I and the addition salts thereof, particularly the physiologically acceptable addition salts thereof with inorganic or organic acids or bases, have valuable properties. Thus, the compounds of general formula I wherein A contains an optionally substituted amino, amidino or guanidino group or a group which can optionally be converted in vivo into an optionally substituted amino, amidino or guanidino group, e.g. an amino, amidino or guanidino group substituted by an alkoxycarbonyl group, and -D-E-F contains carboxyl, sulpho, phosphono, O-alkyl-phosphono or 5-tetrazolyl groups or groups which can be converted in vivo into a carboxyl, sulpho, phosphono, O-alkyl-phosphono or tetrazolyl group, e.g. alkoxy-substituted carbonyl groups, have valuable pharmacological properties, not only an antiinflammatory effect which inhibits the breakdown of bone but in particular antithrombotic and antiaggregatory effects and inhibitory effects on tumours or metastases.

The compounds of general formula I wherein A represents a cyano or cyanoalkyl group are valuable intermediate products for preparing the corresponding aminomethyl and amidino compounds of general formula I.

By way of example, the compounds of general formula I were tested for their biological effects in the following way:

1. Fibrinogen binding to human thrombocytes

Blood obtained by puncture of an antecubital vein was anticoagulated with trisodium citrate (final concentration: 13 mM) and centrifuged for 10 minutes at 170 *g. The supernatant platelet-rich plasma was placed on a Sepharose 2B column (Pharmacia) and eluted with a solution of 90 mM common salt, 14 mM trisodium citrate, 5 mM glucose and 50 mM tris(hydroxymethyl)aminomethane, adjusted to pH 7.4. The gel-filtered platelets (GFP) appearing in front of the plasma proteins were used for the binding tests.

50 µl of a 60 mM calcium chloride solution, 50 µl of a 0.6 mM adenosine diphosphate solution, 100 µl of substance solution or solvent and 50 µl of fibrinogen solution (containing 3 µg I125-fibrinogen) were added to 750 µl of GFP and incubated for 20 minutes at ambient temperature. The non-specific binding was measured in the presence of 3 mg/ml of cold fibrinogen.

900 µl of the incubate were carefully pipetted onto 250 µl of silicon oil (AP 38: AR 20, 1:2 v/v, Wacker Chemie) in Eppendorf vessels and centrifuged for 2 minutes at 10,000 *g. The aqueous supernatant and some of the oil were removed, the tip of the vessel with the platelet pellet was cut off and the quantity of bound fibrinogen was measured in a gamma-counter. The concentration of substance which inhibited fibrinogen binding by 50% was calculated from a series of concentrations and given as the $IC_{50}$.

2. Antithrombotic effect

Method: The thrombocyte aggregation was measured in platelet-rich plasma from healthy test subjects using the Born and Cross method (J. Physiol. 170: 397 (1964)). In order to inhibit coaggulation the blood was mixed with 3.14% sodium citrate in a ratio by volume of 1:10.

Collagen-induced aggregation: The decrease in the optical density of the platelet suspension was measured photometrically and recorded after the addition of the aggregation-initiating substance. The speed of aggregation was concluded from the angle of inclination of the density curve. The point on the curve at which there was maximum transmittance was used to calculate the optical density.

The quantity of collagen used was as little as possible but sufficient to give an irreversible reaction curve. Standard commercial collagen produced by Hormonchemie of Munich was used. Before the addition of collagen the plasma was incubated with the substance for 10 minutes at 37° C.

From the measurements obtained, an $EC_{50}$ was determined graphically, relating to a 50% change in the optical density in terms of inhibiting aggregation.

The Table which follows contains the findings:

| Substance (Example No.) | Fibrinogen Binding test $IC_{50}$[nM] | Inhibition of platelet aggregation $EC_{50}$[nM] |
| --- | --- | --- |
| 1 | 1 800 | 9900 |
| 1(1) | 45 | 1500 |
| 1(2) | 96 | 320 |
| 1(3) | 190 | 1700 |
| 1(4) | 3 900 | >100000 |
| 1(5) | 6 100 | 32000 |
| 1(6) | 17 | 70 |
| 1(7) | 2 400 | 10000 |
| 1(21) | 31 | 620 |
| 1(24) | 470 | 1100 |
| 1(28) | 52 | 390 |
| 1(36) | 37 | 100 |
| 1(46) | 11 | 40 |
| 1(48) | 210 | 1100 |
| 1(49) | 26 | 140 |
| 1(50) | 45 | 290 |
| 1(51) | 3 600 | 13000 |
| 1(55) | 860 | 60000 |
| 1(59) | 150 | 350 |
| 1(62) | 13 | 40 |
| 1(66) | 9.1 | 50 |
| 1(67) | 30 | 60 |
| 1(77) | 4 900 | 8000 |
| 1(82) | 17 000 | 29000 |
| 1(94) | 310 | 400 |
| 1(117) | 230 | 5400 |
| 1(118) | 170 | 460 |
| 1(119) | 210 | 730 |
| 1(137) | | 280 |
| 1(138) | 21 | 40 |
| 1(139) | 6.8 | 30 |
| 1(140) | 21 | 30 |
| 1(141) | 310 | 630 |
| 1(143) | >10 000 | 22000 |
| 1(144) | | 600 |
| 1(145) | 7.7 | 50 |
| 1(146) | 6.5 | 50 |
| 1(147) | 27 | 160 |
| 1(148) | 25 | 110 |
| 1(149) | 470 | 1300 |
| 1(150) | 370 | 9900 |
| 1(153) | 150 | 380 |
| 1(154) | 28 | 310 |
| 1(156) | 3 600 | 4100 |
| 2 | 6 000 | 12000 |
| 2(2) | 25 000 | 630 |
| 2(3) | 18 000 | 3100 |
| 2(4) | 15 000 | 42000 |
| 2(5) | 5 600 | 25000 |
| 2(6) | 240 | 160 |
| 2(20) | 5 700 | 690 |
| 2(27) | 2 500 | 490 |
| 2(34) | 7 400 | 350 |
| 2(43) | 420 | 100 |
| 2(45) | 370 | 280 |
| 2(47) | 32 000 | >100000 |
| 2(48) | 22 000 | >100000 |
| 2(53) | 4 500 | 200 |
| 2(57) | 640 | 320 |
| 2(58) | 4 700 | 140 |
| 2(71) | 13 000 | 14000 |
| 2(75) | 8 000 | 27000 |
| 2(81) | 19 000 | 1500 |
| 2(104) | 7 100 | 2100 |
| 2(105) | 28 000 | 1100 |
| 2(106) | 2 700 | 6600 |
| 2(115) | 530 | 80 |
| 2(116) | 59 000 | 49000 |
| 2(117) | | 630 |
| 2(118) | 2 000 | 70 |
| 2(119) | 280 | 40 |
| 2(122) | | 1200 |
| 2(123) | 3 100 | 70 |
| 2(124) | 1 200 | 130 |
| 2(127) | 5 600 | 18000 |
| 4(9) | 2 600 | 9500 |
| 4(11) | 45 000 | 2300 |
| 4(13) | 32 | 310 |
| 4(14) | 41 | 200 |
| 4(15) | 42 | 300 |
| 4(16) | 1 500 | 1900 |
| 4(18) | 48 | 210 |
| 5 | 9 300 | 32000 |
| 5(1) | >100 000 | 20000 |
| 5(8) | 8 000 | 31000 |
| 5(11) | 5 700 | |
| 5(12) | 3 700 | |
| 5(13) | >10 000 | 24000 |
| 5(18) | >10 000 | 8060 |
| 8 | 750 | 600 |
| 8(1) | 68 000 | 21000 |
| 8(2) | 450 | 370 |
| 8(3) | 29 000 | 6200 |
| 8(5) | 3 000 | 5900 |
| 11(11) | | 210 |
| 11(12) | 43 | 30 |
| 18 | 1 900 | 240 |
| 18(5) | 420 | 120 |
| 30 | 4 400 | 8300 |
| 31 | 250 | 500 |
| 31(1) | 170 | 370 |

Moreover, the compound of Example 5(18) for example inhibited the collagen-induced thrombocyte aggregation ex vivo in Rhesus monkeys after oral administration of 1 mg/kg for up to 8 hours.

The new compounds were well tolerated since the intravenous administration of 30 mg/kg of the compound of Example 1(138) in mice did not lead to the death of any of the three animals tested. Similar results were obtained with the compounds of Examples 1(66) and 1(139) at a dose of 30 mg/kg, although in both cases one animal was sedated.

In view of their inhibitory effect on cell-cell and cell-matrix interactions, the new cyclic urea derivatives of general formula I and the physiologically acceptable addition salts thereof are suitable for combating or preventing diseases in which smaller or larger clumps of cells are produced or cell-matrix interactions are involved, e.g. in combating or preventing venous and arterial thrombosis, cerebro-vascular diseases, pulmonary embolisms, cardiac infarct, arteriosclerosis, osteoporosis and tumour metastasis. They are also suitable as an accompanying therapy in thrombolysis with fibrinolytics or vascular interventions such as transluminal angioplasty or in the treatment of shock, diabetes and inflammation.

For combating or preventing the above-mentioned diseases, the dose is between 0.1 μg and 20 mg/kg of body weight, preferably 1 μg to 10 mg/kg of body weight, in up to 4 doses per day. For this purpose, the compounds of formula I prepared according to the invention may be formulated, optionally in conjunction with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof, to produce conventional galenic preparations such as plain or coated tablets, capsules, powders, suspensions, solutions, sprays or suppositories.

The Examples which follow are intended to illustrate the invention:

Example I 1-(3-Buten-1-yl)-3-(4'-cyano-4-biphenylyl)-imidazolin-2-one 9 g of 1-(4'-cyano-4-biphenylyl)-imidazolidin-2-one were dissolved at 50° C. in 300 ml of dimethylformamide and 1.6 g of a 55% suspension of sodium hydride in oil were added in batches thereto. The mixture was stirred for a further 45 minutes, allowed to cool to ambient temperature and, within 10 minutes, a solution of 4.16 ml of 1-bromo-3-butene in 15 ml of dimethyl-formamide was added dropwise to the resulting suspension and stirred for 3 days at ambient temperature. The reaction mixture was poured onto 400 ml of water and the precipitate obtained was purified, after washing with water, by column chromatography on silica gel (eluant: methylene chloride/ethyl acetate=9:1).
Yield: 3.6 g (33% of theory),
Melting point: 171°–175° C.
$R_f$ value: 0.54 (silica gel; cyclohexane/ethyl acetate=1:1)
The following compounds were obtained analogously:
(1) N-[4-(2-methoxycarbonyl-ethyl)-phenyl]-N-[2-(2,3,5,6-tetrahydro-2-pyranyloxy)-ethyl]-trifluoroacetamide
Heating for 20 hours to 70°–80° C.
$R_f$ value: 0.47 (silica gel; diisopropylether)
(2) N-[4-(2-methoxycarbonyl-ethyl)-phenyl]-N-[3-(2,3,5,6-tetrahydro-2-pyranyloxy)-propyl]-trifluoroacetamide
Heating for 40 hours to 60° C.
$R_f$ value: 0.49 (silica gel; diisopropylether)
(3) 1-methoxycarbonylmethyl-3H-benzimidazol-2-one The base used was potassium tert.-butoxide and the solvent was methanol
$R_f$ value: 0.89 (silica gel; methylene chloride/methanol= 85:15)
(4) 1-(3-buten-1-yl)-3-(4'-cyano-3'-fluoro-4-biphenylyl)-imidazolidin-2-one
(5) 1-(3-buten-1-yl)-3-(3'-chloro-4,-cyano-4-biphenylyl)-imidazolidin- 2-one
(6) 1-(3-buten-1-yl)-3-(4'-cyano-3-methoxy-4-biphenylyl)-imidazolidin-2-one
(7) 1-(3-buten-1-yl)-3-(4'-cyano-3-methylthio-4-biphenylyl)-imidazolidin-2-one
(8) 1-(3-buten-1-yl)-3-(4'-cyano-2,3-dimethyl-4-biphenylyl)-imidazolidin-2-one
(9) 1-(3-buten-1-yl)-3-[4-(5-cyano-2-pyridyl)-phenyl]-imidazolidin-2-one
(10) 1-(3-buten-1-yl)-3-[4-(5-cyano-2-pyrazinyl)-phenyl]-imidazolidin-2-one
(11) 1-(3-buten-1-yl)-3-[4-(5-cyano-2-pyrimidinyl)-phenyl]-imidazolidin-2-one
(12) 1-(3-buten-1-yl)-3-[6-(4-cyano-phenyl)-3-pyridazinyl]-imidazolidin-2-one
(13) 1-(3-buten-1-yl)-3-[2-(4-cyano-phenyl)-5-pyrimidinyl]-imidazolidin-2-one
(14) N-[2-fluoro-4-(2-methoxycarbonyl-ethyl)-phenyl]-N-[2-(2,3,5,6-tetrahydro-2-pyranyloxy)-ethyl]-trifluoroacetamide
(15) N-[2-chloro-4-(2-methoxycarbonyl-ethyl)-phenyl]-N-[2-(2,3,5,6-tetrahydro-2-pyranyloxy)-ethyl]-trifluoroacetamide
(16) N-[2-methoxy-4-(2-methoxycarbonyl-ethyl)-phenyl]-N-[2-(2,3,5,6-tetrahydro-2-pyranyloxy)-ethyl]-trifluoroacetamide The methyl 3-(4-amino-3-methoxy-phenyl)-propionate required for the trifluoroacetylation with trifluoroacetic anhydride was obtained from 3-(3-methoxy-phenyl)-propionic acid by nitrogenation, esterification and reduction with palladium/charcoal in methanol.
(17) N-[4-(2-methoxycarbonyl-ethyl)-2-methyl-phenyl]-N-[2-(2,3,5,6-tetrahydro-2-pyranyloxy)-ethyl]-trifluoro-acetamide The 3-(4-amino-3-methyl-phenyl)-propionic acid was obtained from 3-(3-methyl-phenyl)-propionic acid analogously to Example I (16).
(18) N-[4-(2-methoxycarbonyl-ethyl)-2-methylthio-phenyl]-N-[2-(2,3,5,6-tetrahydro-2-pyranyloxy)-ethyl]-trifluoroacetamide The 3-(4-amino-3-methylthio-phenyl)-propionic acid was obtained from 3-(4-amino-phenyl)-propionic acid analogously to Example III (10).
(19) 1-[6-(4-cyano-phenyl)-3-pyridazinyl]-imidazolidin-2-one
Prepared from imidazolidin-2-one and 3-chloro-6-(4-cyanophenyl)-pyridazine in dimethylsulphoxide
$R_f$ value: 0.30 (silica gel; methylene chloride/methanol= 19:1)
(20) 1-(4-cyano-phenyl)-3-(ethoxycarbonylmethyl)-imidazolidin-2-one
Melting point: 112°–115° C.

Example II 1-(4'-Cyano-4-biphenylyl)-imidazolidin-2-one

A solution of 5.7 g of potassium tert.-butoxide in 15 ml of dimethylformamide was added dropwise at ambient temperature within 10 minutes to a solution of N-(2-chloroethyl)-N'-(4'-cyano-4-biphenylyl)-urea in 100 ml of dimethylformamide. The mixture was stirred for one hour at ambient temperature, poured onto 300 ml of water and the product precipitated was filtered off.
Yield: 13 g (98% of theory),
Melting point: above 200° C.
$R_f$ value: 0.12 (silica gel; cyclohexane/ethyl acetate=1:1)
The following compounds were obtained analogously:
  (1) 1-(4'-cyano-4-biphenylyl)-3,4,5,6-tetrahydro-1H-pyrimidin-2-one
Melting point: above 200° C.
$R_f$ value: 0.44 (silica gel; methylene chloride/methanol=9:1)
  (2) 1-(4'-cyano-3'-fluoro-4-biphenylyl)-imidazolidin-2-one
  (3) 1-(3'-chloro-4'-cyano-4-biphenylyl)-imidazolidin-2-one
  (4) 1-(4'-cyano-3-methoxy-4-biphenylyl)-imidazolidin-2-one
  (5) 1-(4'-cyano-3-methylthio-4-biphenylyl)-imidazolidin-2-one
  (6) 1-(4'-cyano-2,3-dimethyl-4-biphenylyl)-imidazolidin-2-one
  (7) 1-[4-(5-cyano-2-pyridyl)-phenyl]-imidazolidin-2-one
  (8) 1-[4-(5-cyano-2-pyrazinyl)-phenyl]-imidazolidin-2-one
  (9) 1-[4-(5-cyano-2-pyrimidinyl)-phenyl]-imidazolidin-2-one
  (10) 1-[2-(4-cyano-phenyl)-5-pyrimidinyl]-imidazolidin-2-one
  (11) 1-[2-(4'-cyano-4-biphenylyl)-ethyl]-imidazolidin-2-one
  (12) 1-(1-benzyl-4-piperidinyl)-3-[4-(2-methoxycarbonyl-ethyl)-phenyl]-imidazolidin-2-one
  (13) 1-(4-cyano-phenyl)-imidazolidin-2-one
Potassium carbonate was used as base, heating to 60° C. for 6 hours.
Melting point: 172°–175° C.
$R_f$ value: 0.23 (silica gel; cyclohexane/ethyl acetate=1:3)
  (14) 1-(4-cyano-phenyl)-3-[4-[2-(dimethoxy-phosphoryl)-ethyl]-phenyl]-imidazolidin-2-one
Prepared analogously to Example 14.
  (15) 1-[4-(2-methoxycarbonyl-ethyl)-phenyl]-imidazolidin-2-one
Melting point: 171°–172° C.
  (16) 2-[4-(2-methoxycarbonyl-ethyl)-phenyl]-3,4-dihydro-2H,5H-thiadiazol-1,1-dioxide
Melting point: 110°–112° C.
  (17) 1-(4-bromo-2-methyl-phenyl)-3-[4-(2-methoxycarbonyl-ethyl)-phenyl]-imidazolidin-2-one
Prepared from N-(4-bromo-2-methyl-phenyl)-N'-(2-hydroxy-ethyl)-N'-[4-(2-methoxycarbonyl-ethyl)-phenyl]-urea via the mesylate and iodide without purification of these products.
Melting point: 164°–166° C.

Example III

N-(2-Chloroethyl)-N'-(4'-cyano-4-biphenylyl)-urea 1.1 ml of 2-chloroethyl-isocyanate was added to a solution of 4-amino-4'-cyano-biphenyl in 15 ml of dimethylformamide and the mixture was stirred for 3 hours at ambient temperature. The reaction mixture was poured onto 50 ml of water, stirred for 3 hours and the product precipitated was filtered off.
Yield: 1.4 g (91% of theory),
$R_f$ value: 0.40 (silica gel; cyclohexane/ethyl acetate=1:1)
The following compounds were obtained analogously:
  (1) N-(4'-cyano-4-biphenylyl)-N-(2,2-diethoxy-ethyl)-N'-(2-ethoxycarbonyl-ethyl)-urea
The work was done in dioxane as solvent in the presence of ethyl-diisopropylamine at 50° C. Purification was carried out by chromatography on silica gel (eluant: cyclohexane/ethyl acetate=1:1).
The ethyl 3-isocyanato-propionate used was obtained from β-alanine-ethylester-hydrochloride and phosgene in toluene as the solvent.
Melting point: 85°–88° C.
$R_f$ value: 0.28 (silica gel; cyclohexane/ethyl acetate=1:1)
  (2) N-(tert.butyloxycarbonylmethyl)-N-(4'-cyano-4-biphenylyl)-N'-(2-ethoxycarbonyl-ethyl)-urea
Prepared analogously to Example III (1).
Melting point: 118°–120° C. (from tert.butyl-methylether)
$R_f$ value: 0.46 (silica gel; cyclohexane/ethyl acetate=1:1)
  (3) N-(4'-cyano-4-biphenyl)-N-[3-(2,3,5,6-tetrahydro-2-pyranyloxy)-propyl]-N'-(2-ethoxycarbonyl-ethyl)-urea
Prepared analogously to Example III (1).
$R_f$ value: 0.49 (silica gel; cyclohexane/ethyl acetate=1:3)
  (4) N-(3-chloropropyl)-N'-(4'-cyano-4-biphenylyl)-urea
$R_f$ value: 0.39 (silica gel; cyclohexane/ethyl acetate=1:1)
  (5) N-(4-cyano-phenyl)-N'-(2-hydroxy-ethyl)-N'-[4-(2-methoxycarbonyl-ethyl)-phenyl]-urea
Solvent: dioxane
$R_f$ value: 0.32 (silica gel; cyclohexane/ethyl acetate=3:7)
  (6) N-(4-cyano-phenyl)-N'-(3-hydroxy-propyl)-N'-[4-(2-methoxycarbonyl-ethyl)-phenyl]-urea
Solvent: dioxane
Melting point: 86°–89° C.
$R_f$ value: 0.27 (silica gel; cyclohexane/ethyl acetate=3:7)
  (7) N-(2-chloroethyl)-N'-(4'-cyano-3'-fluoro-4-biphenylyl)-urea
The 4-amino-4'-cyano-3'-fluoro-biphenyl used as starting material was obtained from 4-bromo-2-fluoro-benzonitrile by reacting with phenyl boronic acid in the presence of palladium(II)acetate and tris-o-tolyl-phosphine with subsequent nitrogenation and reduction of the nitro group with 5% palladium charcoal in ethyl acetate.
  (8) N-(3'-chloro-4'-cyano-4-biphenylyl)-N'-(2-chloroethyl)-urea
The 4-amino-3'-chloro-4'-cyano-biphenyl used as starting material was obtained analogously to Example III (7).
  (9) N-(2-chloroethyl)-N'-(4'-cyano-3-methoxy-4-biphenylyl)-urea
The 4-amino-4'-cyano-3-methoxy-biphenyl used as starting material was obtained analogously to Example III (7).
  (10) N-(2-chloroethyl)-N'-(4'-cyano-3-methylthio-4-biphenylyl)-urea
The starting material 4-amino-4'-cyano-3-methylthio-biphenyl was obtained from 4'-amino-4-biphenyl-carboxylic acid by reacting with ammonium rhodanide and bromine in acetic acid, saponifying the resulting 2-amino-benzothiazole derivative with dilute potassium hydroxide solution, methylating the mercapto group, protecting the amino group by means of the phthalyl derivative, converting the carboxyl group into a cyano group (via the acid chloride and the acid amide with subsequent dehydration with phosphorusoxychloride/pyridine) and cleaving the phthalyl group with aqueous methylamine solution.
  (11) N-(2-chloroethyl)-N'-(4'-cyano-2,3-dimethyl-4-biphenylyl)-urea The starting material 4-amino-4'-cyano-2,3-dimethyl-biphenyl was obtained analogously to Example III (7).

(12) N-(2-chloroethyl)-N'-[4-(5-cyano-2-pyridyl)-phenyl]-urea

The starting material 2-(4-amino-phenyl)-5-cyano-pyridine was obtained analogously to Example III (7), using 4-(2,2,5,5-tetramethyl-1-aza-2,5-disila-1-cyclopentanyl)-phenyl boronic acid (prepared from 4-(2,2,5,5-tetramethyl-1-aza-2,5-disila-1-cyclopentanyl)-phenyl-lithium and trimethoxyborane) and hydrolytically removing the silyl protecting group.

(13) N-(2-chloroethyl)-N'-[4-(5-cyano-2-pyrazinyl)-urea

The starting material 2-(4-amino-phenyl)-5-cyano-pyrazine was obtained from 4-nitro-phenylglyoxal by condensation with glycinamide, treating the product with phosphorusoxytribromide, bromine exchange with copper (I)cyanide and subsequent reduction of the nitro group analogously to Example III (7).

(14) N-(2-chloroethyl)-N'-[4-(5-cyano-2-pyrimidinyl)-phenyl]-urea

The starting material 2-(4-amino-phenyl)-5-cyano-pyrimidine was obtained from 4-nitro-benzamidine and 3-dimethylamino-2-formyl-acrylonitrile with subsequent reduction of the nitro group analogously to Example III (7).

(15) N-(2-chloroethyl)-N'-[2-(4-cyano-phenyl)-5-pyrimidinyl]-urea

The starting material 5-amino-2-(4-cyano-phenyl)-pyrimidine was obtained by first condensing ethyl 4-amidino-benzoate with diethylmalonate in the presence of sodium methoxide, nitrogenating the resulting pyrimidinedione and chlorinating with phosphorus oxychloride/phosphorus pentachloride and catalytically hydrogenating the product. The resulting 5-amino-2-(4-ethoxycarbonyl-phenyl)-pyrimidine was converted into the aminocarbonyl compound and dehydrated with phosphorus oxychloride/pyridine to obtain the nitrile.

(16) N-[4-(4-cyano-phenyl)-cyclohexyl]-N-(2,2-diethoxyethyl)-N'-(2-ethoxycarbonyl-ethyl)-urea The starting material N-[4-(4-cyano-phenyl)-cyclohexyl]-N-(2,2-diethoxy-ethyl)-amine was obtained by reductive amination of 4-(4-cyano-phenyl)-cyclohexanone with 2,2-diethoxyethylamine in the presence of sodium cyanoborohydride.

(17) N-(2-chloroethyl)-N'-[2-(4'-cyano-4-biphenylyl)-ethyl]-urea

The starting material 2-(4'-cyano-4-biphenylyl)-ethylamine was obtained from 2-(4'-cyano-4-biphenylyl)-ethylbromide and potassium phthalimide and subsequently reacted with aqueous methylamine solution.

(18) N-(4-cyano-3-fluoro-phenyl)-N'-(2-hydroxy-ethyl)-N,-[4-(2-methoxycarbonyl-ethyl)-phenyl]-urea The 4-amino-2-fluoro-benzonitrile from which the isocyanate was obtained analogously to Example III (1) was obtained from 2-fluoro-4-nitro-benzoic acid by conversion into the acid amide, cleaving the water by heating with phosphorus oxychloride/pyridine and reduction with hydrogen in the presence of 5% palladium/charcoal in ethyl acetate.

(19) N-(3-chloro-4-cyano-phenyl)-N'-(2-hydroxy-ethyl)-N'-[4-(2-methoxycarbonyl-ethyl)-phenyl]-urea (The isocyanate was prepared analogously to Example III (1))

(20) N-(4-cyano-2-methylthio-phenyl)-N'-(2-hydroxy-ethyl)-N'-[4-(2-methoxycarbonyl-ethyl)-phenyl]-urea The 4-amino-3-methylthio-benzonitrile which was converted into the isocyanate analogously to Example III (1) was obtained from 4-amino-3-methylthio-benzoic acid analogously to Example III (10).

(21) N-(4-cyano-2-methyl-phenyl)-N'-(2-hydroxy-ethyl)-N'-[4-(2-methoxycarbonyl-ethyl)-phenyl]-urea (The isocyanate was prepared analogously to Example III (1))

(22) N-(4-cyano-2-methoxy-phenyl)-N'-(2-hydroxy-ethyl)-N'-[4-(2-methoxycarbonyl-ethyl)-phenyl]-urea The starting material 4-amino-3-methoxy-benzonitrile, whichwasconverted into the isocyanate analogously to Example III (1),wasobtained from 3-methoxy-4-nitro-benzoic acid analogously to Example III (18)

(23) N-(4-cyano-phenyl)-N'-[2-fluoro-4-(2-methoxycarbonyl-ethyl)-phenyl]-N'-(2-hydroxy-ethyl)-urea

(24) N-[2-chloro-4-(2-methoxycarbonyl-ethyl)-phenyl]-N-(2-hydroxy-ethyl)-N'-(4-cyano-phenyl)-urea

(25) N-(4-cyano-phenyl)-N'-(2-hydroxy-ethyl)-N'-[2-methoxy-4-(2-methoxycarbonyl-ethyl)-phenyl]-urea

(26) N-(4-cyano-phenyl)-N'-(2-hydroxy-ethyl)-N'-[4-(2-methoxycarbonyl-ethyl)-2-methyl-phenyl]-urea

(27) N-(4-cyano-phenyl)-N'-(2-hydroxy-ethyl)-N'-[4-(2-methoxycarbonyl-ethyl)-2-methylthio-phenyl]-urea

(28) N-(4-cyano-phenyl)-N-(2-hydroxy-ethyl)-N'-[5-(2-methoxycarbonyl-ethyl)-2-pyridyl]-urea

(29) N-(4-cyano-phenyl)-N-(2-hydroxy-ethyl)-N'-[4-(2-methoxycarbonyl-ethyl)-cyclohexyl]-urea

(30) N-(4-cyano-phenyl)-N'-(2-hydroxy-ethyl)-N'-(4-methoxycarbonylmethyloxy-phenyl)-urea

(31) N-(4-tert.butyloxy-carbonylmethylthio-phenyl)-N-(2-hydroxy-ethyl)-N'-(4-cyano-phenyl)-urea Melting point: 111°–114° C.

(32) N-(4-cyano-phenyl)-N'-(2-hydroxy-ethyl)-N'-[4-(3-methoxycarbonyl-2-methyl-2-propyl)-phenyl]-urea Melting point: 113°–116° C.

(33) N-(4-cyano-phenyl)-N'-[4-[2-(dimethoxyphosphoryl)-ethyl]-phenyl]-N'-(2-hydroxy-ethyl)-urea

(34) N-(4-cyano-phenyl)-N'-(2-hydroxy-ethyl)-N'-[2-(4-ethoxycarbony 1-phenyl)-ethyl]-urea

(35) N-(4-cyano-phenyl)-N'-(2-hydroxy-ethyl)-N'-[4-(2-methoxycarbonyl-ethenyl)-phenyl]-urea

(36) N-(5-cyano-2-pyridyl)-N'-(2-hydroxy-ethyl)-N'-[4-(2-methoxycarbonyl-ethyl)-phenyl]-urea

(37) N-(1-benzyl-4-piperidinyl)-N'-(2-hydroxy-ethyl)-N'-[4-(2-methoxycarbonyl-ethyl)-phenyl]-urea

(38) N-(4-cyano-phenyl)-N'-(2-hydroxy-ethyl)-N'-[4-(3-methoxycarbonyl-propyl)-phenyl]-urea

(39) N-(4-cyano-phenyl)-N'-(2,2-diethoxy-ethyl)-N'-[4-(2-methoxycarbonyl-ethyl)-phenyl]-urea $R_f$ value: 0.60 (silica gel; cyclohexane, ethyl acetate=1:1)

(40) N-(2-chloroethyl)-N'-(4-cyano-phenyl)-urea $R_f$ value: 0.29 (silica gel; methylene chloride, methanol= 40:1, developed three times)

(41) N-(4-cyano-phenyl)-N'-(2,2-dimethoxy-ethyl)-N'-[2-(4-methoxycarbonyl-phenyl)-ethyl]-urea Melting point: 109°–110° C.

(42) N-(4-cyano-phenyl)-N'-(2-hydroxy-propyl)-N'-[4-(2-methoxycarbonyl-ethyl)-phenyl]-urea The work was done in dioxane without an auxiliary base.

$R_f$ value: 0.40 (silica gel; ethyl acetate/cyclohexane=2:1)

(43) N-acetylamino-N-[4-(2-ethoxycarbonyl-ethyl)-phenyl]-N'-(4-cyano-phenyl)-urea The work was done in dioxane without an auxiliary base.

Melting point: 126°–128° C.

(44) N-(4-cyano-phenyl)-N'-(2-hydroxy-propyl)-N'-[4-(2-methoxycarbonyl-ethyl)-phenyl]-urea The work was done in dioxane without an auxiliary base.
$R_f$ value: 0.25 (silica gel; cyclohexane/ethyl acetate=1:1)

(45) N-(4-cyano-phenyl)-N'-formylamino-N'-[4-(2-methoxycarbonyl-ethyl)-phenyl]-urea The work was done in dioxane without an auxiliary base.
Melting point: 166°–168° C.

(46) N-(4-cyano-phenyl)-N-formylamino-N'-[4-(2-methoxycarbonyl-ethyl)-phenyl]-urea Melting point: 180°–183° C.

(47) N-acetylamino-N-(4-cyano-phenyl)-N'-[4-(2-methoxycarbonyl-ethyl)-phenyl]-urea Melting point: 153°–155° C.

(48) N-(2-chloro-ethyl)-N'-[4-(2-methoxycarbonyl-ethyl)-phenyl]-urea

Melting point: 124°–125° C.

(49) N-[1-(4-cyano-phenyl)-4-piperidinyl]-N-(2,2-dimethoxyethyl)-N'-(2-ethoxycarbonyl-ethyl)-urea Melting point: 90°–92° C.

(50) N-(4-cyano-phenyl)-N-(propionylamino)-N'-[4-(2-ethoxycarbonyl-ethyl)-phenyl]-urea Melting point: 149°–153° C.

(51) N-(4-cyano-phenyl)-N'-(2,2-diethoxy-ethyl)-N'-[4-(2-methoxycarbonyl-ethenyl)-phenyl]-urea $R_f$ value: 0.68 (silica gel; cyclohexane/ethyl acetate=1:1)

(52) N-(4-cyano-phenyl)-N'-[4-(2-dibenzylamino-2-methoxycarbonyl-ethyl)-phenyl]-N'-(2,2-diethoxy-ethyl)-urea $R_f$ value: 0.52 (silica gel; cyclohexane/ethyl acetate=2:1)

(53) N-[4-(2-tert.butyloxycarbonylamino-2-methoxycarbonyl-ethyl)-phenyl]-N'-(4-cyano-phenyl)-N'-(2,2-diethoxy-ethyl)-urea $R_f$ value: 0.15 (silica gel; cyclohexane/ethyl acetate=2:1)

(54) N-(4-bromo-2-methyl-phenyl)-N'-(2-hydroxy-ethyl)-N'-[4-(2-methoxycarbonyl-ethyl)-phenyl]-urea The work was done in dioxane without an auxiliary base.
Melting point: 101°–104° C.

Example IV

N-(4'-Cyano-4-biphenylyl)-N-(2,2-diethoxy-ethyl)-amine

A mixture of 10 g of 4-amino-4'-cyano-biphenyl, 8.3 ml of bromoacetaldehyde-diethylacetal, 13.9 ml of ethyl-diisopropylamine and 20 ml of dimethylformamide was stirred for 16 hours at a bath temperature of 160° C. It was evaporated to dryness and the residue was purified by column chromatography over silica gel (eluant: cyclohexane/ethyl acetate=2:1).
Yield: 3 g (19% of theory).
Melting point: 88°–90° C.
$R_f$ value: 0.54 (silica gel; cyclohexane/ethyl acetate=2:1)

The following compounds were obtained analogously:

(1) N-(tert.butyloxycarbonyl-methyl)-N-(4'-cyano-4-biphenylyl)-amine

The work was done at ambient temperature, recrystallising from cyclohexane/ethyl acetate=20:2
Melting point: 151°–153° C.
$R_f$ value: 0.76 (silica gel; cyclohexane/ethyl acetate=1:1)

(2) N-(4'-cyano-4-biphenylyl)-N-[3-(2,3,5,6-tetrahydro-2-pyranyl)-propyl]-amine

The work was done at 110° C.
Melting point: 111°–113° C.
$R_f$ value: 0.65 (silica gel; cyclohexane/ethyl acetate=1:1)

(3) N-(2,2-diethoxy-ethyl)-N-[4-(2-methoxycarbonyl-ethyl)-phenyl]-amine $R_f$ value: 0.35 (silica gel; cyclohexane/ethyl acetate=8:2)

(4) N-(2,2-diethoxy-ethyl)-N-[2-(4-methoxycarbonyl-phenyl)-ethyl]-amine

The starting materials used were 2,2-dimethoxy-ethylamine and methyl 4-(2-chloro-ethyl)-benzoate.
Heating was carried out for 72 hours to 50° C.
$R_f$ value: 0.46 (silica gel; ethyl acetate/methanol=4:1)

(5) N-(4-cyano-phenyl)-glycine-tert.-butylester
Melting point: 110°–112° C.

(6) methyl 4-[(2,2-diethoxy-ethyl)-amino]-cinnamate
$R_f$ value: 0.79 (silica gel; cyclohexane/ethyl acetate=1:1)

(7) methyl 2-dibenzylamino-3-[4-[(2,2-diethoxy-ethyl)-amino]-phenyl]-propionate
$R_f$ value: 0.59 (silica gel; cyclohexane/ethyl acetate=2:1)

(8) methyl 2-dibenzylamino-3-(4-nitro-phenyl)-propionate

The work was done in methanol.
$R_f$ value: 0.65 (silica gel; cyclohexane/ethyl acetate=2:1)

(9) methyl 2-tert.butyloxycarbonylamino-3-[4-(2,2-diethoxy-ethylamino)-phenyl]-propionate
$R_f$ value: 0.45 (silica gel; cyclohexane/ethyl acetate=2:1)

Example V

N-(4'-Cyano-4-biphenylyl)-N-(3-methanesulphonyloxy-propyl)-N'-(2-ethoxycarbonyl-ethyl)-urea A mixture of 2 g of N-(4'-cyano-4-biphenylyl)-N-(3-hydroxypropyl)-N'-(2-ethoxycarbonyl-ethyl)-urea, 0.45 ml of methanesulphonyl chloride and 15 ml of methylene chloride was cooled to 0° C. and within 15 minutes mixed with 0.8 ml of triethylamine. The mixture was stirred for one hour at 0° C. and a further hour at ambient temperature, 25 ml of methylene chloride were added and the mixture was extracted with water. It was evaporated down and the residue was crystallised by triturating with tert.-butylmethylether.
Yield: 1.9 g (79% of theory).
$R_f$ value: 0.47 (silica gel; ethyl acetate)

The following compounds were obtained analogously:

(1) N-(4-cyano-phenyl)-N'-(2-methanesulphonyloxy-ethyl)-N'-[4-(2-methoxycarbonyl-ethyl)-phenyl]-urea
$R_f$ value: 0.39 (silica gel; cyclohexane/ethyl acetate=3:7)

(2) N-(4-cyano-phenyl)-N'-(3-methanesulphonyloxy-propyl)-N'-[4-(2-methoxycarbonyl-ethyl)-phenyl]-urea
$R_f$ value: 0.43 (silica gel; cyclohexane/ethyl acetate=3:7)

(3) N-(4-cyano-3-fluoro-phenyl)-N'-(2-methanesulphonyloxy-ethyl)-N'-[4-(2-methoxycarbonyl-ethyl)-phenyl]-urea (4) N-(3-chloro-4-cyano-phenyl)-N'-(2-methanesulphonyloxy-ethyl)-N'-[4-(2-methoxycarbonyl-ethyl)-phenyl]-urea (5) N-(3-cyano-2-methylthio-phenyl)-N'-(2-methanesulphonyloxy-ethyl)-N'-[4-(2-methoxycarbonyl-ethyl)-phenyl]-urea (6) N-(4-cyano-2-methyl-phenyl)-N'-(2-methanesulphonyloxy-ethyl)-N'-[4-(2-methoxycarbonyl-ethyl)-phenyl]-urea (7) N-(4-cyano-2-methoxy-phenyl)-N'-(2-methanesulphonyloxy-ethyl)-N'-[4-(2-methoxycarbonyl-ethyl)-phenyl]-urea (8) N-(4-cyano-phenyl)-N'-[2-fluoro-4-(2-methoxycarbonyl-ethyl)-phenyl]-N'-(2-methanesulphonyloxy-ethyl)-urea (9) N-[2-chloro-4-(2-methoxycarbonyl-ethyl)-phenyl]-N-(2-methanesulphonyloxy-ethyl)-N'-(4-cyano-phenyl)-urea

39

(10) N-(4-cyano-phenyl)-N'-(2-methanesulphonyloxy-ethyl)-N'-[2-methoxy-4-(2-methoxycarbonyl-ethyl)-phenyl]-urea

(11) N-(4-cyano-phenyl)-N'-(2-methanesulphonyloxy-ethyl)-N'-[4-(2-methoxycarbonyl-ethyl)-2-methyl-phenyl]-urea

(12) N-(4-cyano-phenyl)-N'-(2-methanesulphonyloxy-ethyl)-N'-[4-(2-methoxycarbonyl-ethyl)-2-methylthio-phenyl]-urea

(13) N-(4-cyano-phenyl)-N-(2-methanesulphonyloxy-ethyl)-N'-[5-(2-methoxycarbonyl-ethyl)-2-pyridyl]-urea

(14) N-(4-cyano-phenyl)-N-(2-methanesulphonyloxy-ethyl)-N'-[4-(2-methoxycarbonyl-ethyl)-cyclohexyl]-urea

(15) N-(4-cyano-phenyl)-N'-(2-methanesulphonyloxy-ethyl)-N'-(4-methoxycarbonylmethyloxy-phenyl)-urea

(16) N-(4-tert.butyloxycarbonylmethylthio-phenyl)-N-(2-methanesulphonyloxy-ethyl)-N'-(4-cyano-phenyl)-urea $R_f$ value: 0.35 (silica gel; methylene chloride/ethyl acetate=95:5)

(17) N-(4-cyano-phenyl)-N'-(2-methanesulphonyloxy-ethyl)-N'-[4-(3-methoxycarbonyl-2-methyl-2-propyl)-phenyl]-urea $R_f$ value: 0.57 (silica gel; cyclohexane/ethyl acetate

(18) N-(4-cyano-phenyl)-N'-[4-[2-(dimethoxy-phosphoryl)-ethyl]-phenyl]-N'-(2-methanesulphonyloxy-ethyl)-urea

(19) N-(4-cyano-phenyl)-N'-[2-(4-ethoxycarbonyl-phenyl)-ethyl]-N'-(2-methanesulphonyloxy-ethyl)-urea

(20) N-(4-cyano-phenyl)-N'-(2-methanesulphonyloxy-ethyl)-N'-[4-(2-methoxycarbonyl-ethenyl)-phenyl]-urea

(21) N-(5-cyano-2-pyridyl)-N'-(2-methanesulphonyloxy-ethyl)-N'-[4-(2-methoxycarbonyl-ethyl)-phenyl]-urea

(22) N-(1-benzyl-4-piperidinyl)-N'-(2-methane-sulphonyloxy-ethyl)-N'-[4-(2-methoxycarbonyl-ethyl)-phenyl]-urea

(23) N-(4-cyano-phenyl)-N'-(2-methanesulphonyloxy-ethyl)-N'-[4-(3-methoxycarbonyl-propyl)-phenyl]-urea

(24) 1-(4-cyano-phenyl)-3-(2-methanesulphonyloxy-ethyl)-imidazolidin-2-one

Melting point: 98°–100° C.

(25) N'-(4-cyanomethyl-phenyl)-N'-(2-methane-sulphonyloxy-ethyl)-N'-(4-methoxycarbonylmethyl-phenyl)-urea $R_f$ value: 0.19 (silica gel; cyclohexane/ethyl acetate=6:4)

Example VI

N-(4'-Cyano-4-biphenylyl)-N-(3-hydroxy-propyl)-N'-(2-ethoxycarbonyl-ethyl)-urea 4.1 g of N-(4'-cyano-4-biphenylyl)-N-[3-(2,3,5,6-tetrahydro-2-pyranyloxy)-propyl]-N'-(2-ethoxycarbonyl-ethyl)-urea were dissolved in 15 ml of ethanol, 0.2 ml of ethereal hydrochloric acid were added and the mixture was stirred for 2 hours at ambient temperature. It was evaporated to dryness, taken up in 200 ml of methylene chloride, extracted with 10% sodium bicarbonate solution and the organic phase was evaporated to dryness. The residue was purified by column chromatography on silica gel (eluant: ethyl acetate).

Yield: 2.1 g (64% of theory).

40

Melting point: 120°–122° C.

$R_f$ value: 0.36 (silica gel; ethyl acetate)

The following compound was obtained analogously:

(1) 1-(4-cyano-phenyl)-piperidin-4-one

Prepared from the corresponding ethylene ketal with pyridinium toluenesulphonate in acetone/water at 100° C.

Melting point: 102°–104° C.

Example VII

N-(2-Hydroxy-ethyl)-N-[4-(2-methoxycarbonyl-ethyl)-phenyl]-amine 1.5 g of N-[4-(2-methoxycarbonyl-ethyl)-phenyl]-N-[2-(2,3,5,6-tetrahydro-2-pyranyloxy)-ethyl]-trifluoro-acetamide were stirred for 2 hours in a mixture of 20 ml of methanol and 2.5 ml of 4N sodium hydroxide solution at ambient temperature. Then the mixture was neutralised with glacial acetic acid, evaporated down and all the water was eliminated by boiling with toluene using a water separator. The residue was concentrated by evaporation, taken up in 20 ml of methanol, 2 ml of methanolic hydrochloric acid were added and the resulting mixture was left to stand for 16 hours at ambient temperature. The precipitate was filtered off, the filtrate was evaporated down and stirred with 10 ml of methylene chloride and 5 ml of 0.1N sodium hydroxide solution. The organic phase was evaporated down and the remaining oil was used directly for further processing.

Yield: 0.65 g (78% of theory).

$R_f$ value: 0.43 (silica gel; cyclohexane/ethyl acetate=3:7)

The following compounds were obtained analogously:

(1) N-(3-hydroxy-propyl)-N-[4-(2-methoxycarbonyl-ethyl)-phenyl]-amine $R_f$ value: 0.44 (silica gel; cyclohexane/ethyl acetate=3:7)

(2) N-[2-fluoro-4-(2-methoxycarbonyl-ethyl)-phenyl]-N-(2-hydroxy-ethyl)-amine (3) N-[2-chloro-4-(2-methoxycarbonyl-ethyl)-phenyl]-N-(2-hydroxy-ethyl)-amine (4) N-(2-hydroxy-ethyl)-N-[2-methoxy-4-(2-methoxycarbonyl-ethyl)-phenyl]-amine (5) N-(2-hydroxy-ethyl)-N-[4-(2-methoxycarbonyl-ethyl)-2-methyl-phenyl]-amine (6) N-(2-hydroxy-ethyl)-N-[4-(2-methoxycarbonyl-ethyl)-2-methylthio-phenyl]-amine Example VIII 3-(4-Cyano-phenyl)-3H-imidazo[4,5-b]pyridin-2-one 0.21 g of 3-amino-2-[(4-cyano-phenyl)-amino]-pyridine and 0.26 g of N-ethyl-diisopropylamine were dissolved in 4.5 ml of methylene chloride and, whilst cooling with ice, 0.5 ml of a 20% solution of phosgene in toluene was added in batches and resulting mixture was stirred for 1.5 hours at ambient temperature. A further 0.3 ml of the phosgene solution was added and stirring was continued for 20 minutes. The precipitate obtained was filtered off and washed with methylene chloride.

Yield: 0.17 g (72% of theory).

$R_f$ value: 0.47 (silica gel; methylene chloride/methanol=19:1)

The following compound was obtained analogously:

(1) 3-(4'-cyano-4-biphenylyl)-3H-imidazo[4,5-b]pyridin-2-one $R_f$ value: 0.44 (silica gel; methylene chloride/methanol=9:1)

Example IX

1-[4-(2-Methoxycarbonyl-ethyl)-phenyl]-3-(4-piperidinyl)-imidazolidin-2-one

Prepared by treating 1-(1-benzyloxycarbonyl-4-piperidinyl)-3-[4-(2-methoxycarbonyl-ethyl)-phenyl]-imidazolidin-2-one with hydrogen at 3 bars in the presence of 5% palladium/charcoal in methanol.

Example X

2-[(2-Ethoxycarbonyl-ethyl)-aminosulphonyloxy]-phenol 1.54 g of .-alanine ethylester-hydrochloride and 1.9 g of 1,2-sulphonyldioxybenzene were dissolved in 10 ml of dimethylformamide, 1.55 g of ethyl-diisopropylamine were added and the mixture was stirred for two hours at ambient temperature. The solvent was distilled off in vacuo and the residue was purified by column chromatography (silica gel; eluant: cyclohexane/ethyl acetate=8:2)
Yield: 1.4 g (48% of theory)
$R_f$ value: 0.31 (silica gel; cyclohexane/ethyl acetate=7:3)

The following compound was obtained analogously:

(1) 4-cyano-4'-[(2-ethoxycarbonyl-ethyl)-aminosulphonylamino]-biphenyl

The work was done without an auxiliary base and by heating for 15 hours to 80° C.
Melting point: 103°–105° C.
$R_f$ value: 0.21 (silica gel; cyclohexane/ethyl acetate=7:3)

Example XI

Methyl 3-[4-[(2-hydroxy-propyl)-amino]-phenyl]-propionate 6 g of methyl 3-(4-amino-phenyl)-propionate hydrochloride were suspended in methylene chloride and 27.9 ml of 1N sodium hydroxide solution were added. The organic phase was separated off, the mixture was extracted twice more with methylene chloride and the combined organic phases were evaporated down. The residue was taken up in 50 ml of methanol and 1.9 ml of propylene oxide and 2 ml of water were added. It was stirred for 48 hours at ambient temperature, evaporated down and purified over silica gel (eluant: cyclohexane/ethyl acetate=1:1).
Yield: 3.5 g (54% of theory),
$R_f$ value: 0.40 (silica gel; cyclohexane/ethyl acetate=1:1)

Example XII

4-[(2-Hydroxy-propyl)-amino]-benzonitrile 12.1 g of 4-fluoro-benzonitrile, 7.5 g of 2-hydroxy-propylamine and 17.4 ml of N-ethyl-diisopropylamine were heated together to 100° C. for 2.5 hours. The mixture was poured onto 250 ml of water, extracted five times with 50 ml of ethyl acetate and the combined organic phases were evaporated down. The product remaining was purified by column chromatography (silica gel; eluant: ethyl acetate) and crystallised by triturating with a 1:1-mixture of tert.butyl-methylether and petroleum ether.
Yield: 2.2 g (13% of theory),
Melting point: 70°–73° C.

The following compound was obtained analogously:

(1) 1-(4-cyano-phenyl)-4,4-ethylenedioxy-piperidine
Melting point: 136°–138° C.

Example XIII

1-[4-(2-Methoxycarbonyl-ethyl)-cyclohexyl]-imidazolidin-2-one 2 g of 1-[4-(2-methoxycarbonyl-ethyl)-phenyl]-imidazolidin-2-one were hydrogenated in a mixture of 20 ml of methanol and 30 ml of glacial acetic acid in the presence of a platinum/rhodium catalyst with hydrogen at 5 bars at 50° C. for 50 minutes. The catalyst was filtered off, the filtrate was evaporated down and the remaining product was used without further purification.
Yield: 2.03 g (100% of theory),
$R_f$ value: 0.29 (silica gel; ethyl acetate/cyclohexane=9:1)

Example XIV

Methyl 3-[4-[(2-chloro-ethyl)-aminosulphonylamino]-phenyl]-propionate

At −30° C., 6.7. g of N-(2-chloroethyl)-N-chlorosulphonyl-amine, dissolved in 10 ml of methylene chloride, were added dropwise to a solution of 8.6 g of methyl 3-(4-amino-phenyl)-propionate hydrochloride and 12.9 g of N-ethyl-diisopropylamine in 40 ml of methylene chloride. The mixture was stirred for a further 2 hours, whilst coming up to ambient temperature. The reaction mixture was washed with water, evaporated down and purified by column chromatography (silica gel; cyclohexane/ethyl acetate=7:3).
Yield: 8.3 g (65% of theory),
Melting point: 97°–99° C.

The following compound was obtained analogously:

(1) Tert.butylester of N-(4-cyano-phenyl)-N-methoxycarbonyl-glycine Potassium carbonate and 4-dimethylamino-pyridine in chloroform were used.
$R_f$ value: 0.42 (silica gel; cyclohexane/ethyl acetate=7:3)

Example XV 1-(4-Cyano-phenyl)-4-[(2,2-dimethoxy-ethyl)-amino]-piperidine 11 g of 1-(4-cyano-phenyl)-piperidin-4-one were dissolved in 90 ml of acetonitrile, then mixed with 10 ml of water and 6.9 g of aminoacetaldehyde-dimethylacetal. 18.3 ml of 3N hydrochloric acid were added dropwise and 4.5 g of sodium cyanoborohydride were added. After 20 minutes' stirring at ambient temperature the acetonitrile was evaporated off in vacuo and the residue was extracted with ethyl acetate. The residue remaining after evaporation of the ethyl acetate phases was purified by chromatography on silica gel (eluant: methylene chloride/methanol=100:3).
Yield: 10.8 g (74% of theory),
$R_f$ value: 0.34 (silica gel; methylene chloride/methanol/concentrated ammonia=95:5:0.1)

The following compounds were obtained analogously:

(1) Methyl 3-[4-[(2-hydroxy-ethyl)-amino]-phenyl]-3-methyl-butyrate
$R_f$ value: 0.35 (silica gel; cyclohexane/ethyl acetate=1:1)

(2) Methyl 4-[(2-hydroxy-ethyl)-amino]-phenylacetate
$R_f$ value: 0.25 (silica gel; cyclohexane/ethyl acetate=1:1)

Example XVI

N-(4-Cyano-phenyl)-N-methoxycarbonyl-glycine-[4-(2-methoxycarbonyl-ethyl)-anilide]

A mixture of 3.7 g of N-(4-cyano-phenyl)-N-methoxycarbonyl-glycine, 2.4 g of i-hydroxy-benzotriazole, 150 ml of tetrahydrofuran, 2.81 g of methyl 3-(4-amino-phenyl)-propionate, 4.2 g of N,N'-dicyclohexylcarbodiimide and 1.62 g of triethylamine was stirred for 64 hours at ambient temperature. The precipitate formed was filtered off, the filtrate was evaporated down and the residue was purified by column chromatography over silica gel (eluant: cyclo-hexane/ethyl acetate=1:1 to 2:3).

Yield: 5.5 g (88% of theory).
Melting point: 100°–110° C.

The following compound was obtained analogously:

(1) N-(4-cyano-phenyl)-N'-propionyl-hydrazine

Carbonyldiimidazole in tetrahydrofuran was used.
Melting point: 143°–145° C.

Example XVII

N-(4-Cyano-phenyl)-N-methoxycarbonyl-glycine 7 g of the tert.butylester of N-(4-cyano-phenyl)-N-methoxycarbonyl-glycine were dissolved in 70 ml of methylene chloride and a solution of 18 ml of trifluoroacetic acid in 18 ml of methylene chloride was added dropwise thereto. The mixture was left to stand for 16 hours at ambient temperature, evaporated down, the residue was taken up in tert.butylmethylether, washed with water and the organic phase was evaporated down. The residue was briefly boiled with 50 ml of diethylether and, after cooling in the ice bath, filtered off. Another fraction can be obtained from the mother liquors.

Yield: 3.85 g (68% of theory).
Melting point: 134°–137° C.

Example XVIII

Methyl 3-(4-amino-phenyl)-2-dibenzylamino-propionate 5.35 g of methyl 2-dibenzylamino-3-(4-nitro-phenyl)-propionate, dissolved in 100 ml of methanol, were treated with hydrogen under a pressure of 5 bars in the presence of 1 g of Raney nickel at ambient temperature for 8 hours. The catalyst was filtered off, the filtrate was evaporated down and the crude product remaining was used without purification.

Yield: 4.9 g (92% of theory).

$R_f$ value: 0.45 (silica gel; cyclohexane/ethyl acetate=2:1)

The following compounds were obtained analogously:

(1) 3-amino-2-[(4-cyano-phenyl)-amino]-pyridine

The work was done in a 3:1 mixture of ethyl acetate and methanol with 10% palladium/charcoal $R_f$ value: 0.62 (silica gel; methylene chloride/methanol=9:1)

(2) 3-amino-2-[(4'-cyano-4-biphenylyl)-amino]-pyridine

The work was done in a 3:1 mixture of ethyl acetate and methanol with 10% palladium/charcoal $R_f$ value: 0.66 (silica gel; methylene chloride/methanol= 19:1)

Example XIX 1-(4-Cyano-phenyl)-3-(2-hydroxy-ethyl)-imidazolidin-2-one 0.71 g of lithium borohydride were added in batches to a solution of 8.8 g of 1-(4-cyano-phenyl)-3-(ethoxycarbonylmethyl)-imidazolidin-2-one in 500 ml of tetrahydrofuran with stirring at ambient temperature. The mixture was stirred for 1 hour at ambient temperature and for 2 hours at 60° C., then after cooling in an ice bath 16.5 ml of 2N hydrochloric acid were added and the resulting mixture was evaporated down in vacuo. The residue was digested with 50 ml of methanol, the methanol phase was evaporated down and the residue was purified over silica gel (eluant: ethyl acetate/methanol=9:1)

Yield: 5.0 g (67% of theory).
Melting point: 112°–114° C.

Example XX

N-(4-Cyanomethyl-phenyl)-N'-(2-hydroxy-ethyl)-N'-(4-methoxycarbonylmethyl-phenyl)-urea 1.46 g of carbonyldiimidazole and 1.04 g of imidazole were dissolved in 20 ml of tetrahydrofuran. The mixture was cooled to 0° C. and 1.18 g of 4-amino-benzylcyanide were added. After about 3 minutes a solution of methyl 4-[(2-hydroxy-ethyl)-amino]-phenylacetate in 7 ml of tetrahydrofuran was rapidly added dropwise, the ice cooling was taken away and the mixture was stirred for 16 hours at ambient temperature (a precipitate formed initially was filtered off). The mixture was concentrated down, the residue was taken up in ethyl acetate, washed with 1N hydrochloric acid and water and the organic phase was evaporated down. The residue was purified by chromatography on silica gel (eluant: ethyl acetate/methylene chloride=1:1).

Yield: 1.4 g (42% of theory).
Melting point: 140°–142° C.

Example XXI

1-[4-(1-Hydroxyimino-ethyl)-phenyl]-3-[4-(2-methoxycarbonylethyl)-phenyl]-imidazolidin-2-one 1.1 g of 1-(4-acetyl-phenyl)-3-[4-(2-methoxycarbonyl-ethyl)-phenyl]-imidazolidin-2-one were suspended in a mixture of 10 ml of dioxane and 10 ml of methanol, mixed with a solution of 0.25 g of hydroxylamine-hydrochloride in 4 ml of water and refluxed for 2.5 hours. Then the mixture was evaporated down in vacuo and the residue was triturated with water, whereupon it crystallises.

Yield: 1.1 g (92% of theory).
Melting point: 241°–243° C. (sinters from 235° C.)

The following compound was obtained analogously:

(1) 1-(1-hydroxyimino-5-indanyl)-3-[4-(2-methoxycarbonylethyl)-phenyl]-imidazolidin-2-one $R_f$ value: 0.13 (silica gel; methylene chloride/ethyl acetate= 9:1)

Example XXII 1-(4-Acetyl-phenyl)-3-[4-(2-methoxycarbonyl-ethyl)-phenyl]-imidazolidin-2-one Prepared analogously to Example 25 from 1-[4-(2-methoxycarbonylethyl)-phenyl]-imidazolidin-2-one and 4-bromo-acetophenone.

Melting point: 198°–200° C.

$R_f$ value: 0.33 (silica gel; methylene chloride/ethyl acetate= 25:1)

The following compound was obtained analogously:

(1) 1-[4-(2-methoxycarbonyl-ethyl)-phenyl]-3-(1-oxo-5-indanyl)-imidazolidin-2-one Melting point: 204°–206° C.

$R_f$ value: 0.39 (silica gel; methylene chloride/ethyl acetate= 9:1)

Example 1

1-(4'-Amidino-4-biphenylyl)-3-carboxymethyl-imidazolidin-2-one 0.35 g of 1-(4'-amidino-4-biphenylyl)-3-methoxycarbonylmethyl-imidazolin-2-one hydrochloride were suspended in 9 ml of methanol. 2.7 ml of 1N sodium hydroxide solution were added and the mixture was stirred for 16hours at ambient temperature. The solvent was distilled off in vacuo and the residue was mixed with 10 ml of water. Ammonium chloride was added as a buffer. The product precipitated was filtered off.

Yield: 0.19 g (62% of theory).
Melting point: above 200° C.
$R_f$ value: 0.61 (Reversed Phase Plate RP8; 10% sodium chloride solution/methanol=4:6)
Calc.×H$_2$O: C 60.65 H 5.67 N 15.72
Found: 61.20 5.57 15.98

The following compounds were obtained analogously:

(1) 1-(4'-amidino-4-biphenylyl)-3-(2-carboxy-ethyl)-imidazolidin-2-one

Melting point: above 200° C.
$R_f$ value: 0.58 (Reversed Phase Plate RP8; 10% sodium chloride solution/methanol=4:6)
Calc.×0.5 H$_2$O: C 63.14 H 5.87 N 15.51
Found: 63.37 5.80 15.13

(2) 1-(4'-amidino-4-biphenylyl)-3-(2-carboxy-ethyl)-imidazolidin-2,4-dione

The starting material used was 1-(4'-amidino-4-biphenylyl)-3-(2-ethoxycarbonyl-ethyl)-imidazolidin-2,4-dione hydrochloride Melting point: above 200° C.
$R_f$ value: 0.66 (Reversed Phase Plate RP8; 10% sodium chloride solution/methanol=4:6)
Calc.×0.25 H2O: C 61.52 H 5.01 N 15.11
Found: 61.89 4.97 14.97

(3) 1-(4'-amidino-4-biphenylyl)-3-(2-carboxy-ethyl)-3H-imidazol-2-one

The starting material used was 1-(4'-amidino-4-biphenylyl)-3-(2-ethoxycarbonyl-ethyl)-3H-imidazol-2-one hydrochloride Melting point: above 200° C
$R_f$ value: 0.68 (Reversed Phase Plate RP8; 5% sodium chloride solution/methanol=4:6)
Calc.×0.25 H$_2$O: C 64.30 H 5.24 N 15.79
Found: 64.61 5.34 15.45

(4) 1-(4'-amidino-4-biphenylyl)-3-(2-carboxy-ethyl)-3,4,5,6-tetrahydro-1H-pyrimidin-2-one The starting material used was 1-(4'-amidino-4-biphenylyl)-3-(2-ethoxycarbonyl-ethyl)-3,4,5,6-tetrahydro-1H-pyrimidin-2-one and the work was done in ethanol as solvent Melting point: above 200° C.
$R_f$ value: 0.54 (Reversed Phase Plate RP8; 10% sodium chloride solution/methanol=4:6)
Calc.×0.25 H2O: C 64.76 H 6.12 N 15.11
Found: 64.62 6.13 14.82

(5) 1-(4'-amidino-4-biphenylyl)-3-carboxymethyl-3,4,5,6-tetrahydro-1H-pyrimidin-2-one Melting point: above 200° C.
$R_f$ value: 0.63 (Reversed Phase Plate RP8; 10% sodium chloride solution/methanol=4:6)
Calc.×0.75 H2O: C 62.37 H 5.92 N 15.31
Found: 62.39 5.94 15.55

(6) 1-(4-amidino-phenyl)-3-[4-(2-carboxy-ethyl)-phenyl]-imidazolidin-2-one

Lithium hydroxide was used and the solvent was a 5:4 mixture of tetrahydrofuran and water.
Melting point: above 270° C.
$R_f$ value: 0.68 (Reversed Phase Plate RP8; 10% sodium chloride solution/methanol=4:6)

(7) 1-(4-amidino-phenyl)-3-[4-(2-carboxy-ethyl)-phenyl]-3,4,5,6-tetrahydro-1H-pyrimidin-2-one Lithium hydroxide was used and, as the solvent, a 5:4 mixture of tetrahydrofuran and water was used.
Melting point: above 270° C.
$R_f$ value: 0.60 (Reversed Phase Plate RP8; 10% sodium chloride solution/methanol=4:6)

(8) 1-[2-(4'-amidino-4-biphenylyl)-ethyl]-3-carboxymethyl-3H-benzimidazol-2-one $R_f$ value: 0.55 (silica gel; methylene chloride, methanol=6:4)

(9) 1-(4'-amidino-3'-fluoro-4-biphenylyl)-3-(2-carboxy-ethyl)-imidazolidin-2-one

(10) 1-(4'-amidino-3'-chloro-4-biphenylyl)-3-(2-carboxy-ethyl)-imidazolidin-2-one

(11) 1-(4'-amidino-3-methoxy-4-biphenylyl)-3-(2-carboxy-ethyl)-imidazolidin-2-one

(12) 1-(4'-amidino-3-bromo-4-biphenylyl)-3-(2-carboxy-ethyl)-imidazolidin- 2-one

(13) 1-(4'-amidino-3-methylthio-4-biphenylyl)-3-(2-carboxy-ethyl)-imidazolidin-2-one

(14) 1-(4'-amidino-3-methylsulphonyl-4-biphenylyl)-3-(2-carboxy-ethyl)-imidazolidin-2-one

(15) 1-(4'-amidino-3-methylsulphinyl-4-biphenylyl)-3-(2-carboxy-ethyl)-imidazolidin-2-one

(16) 1-(4'-amidino-2,3-dimethyl-4-biphenylyl)-3-(2-carboxy-ethyl)-imidazolidin-2-one

(17) 1-(4'-amidino-3-nitro-4-biphenylyl)-3-(2-carboxy-ethyl)-imidazolidin-2-one

(18) 1-(4'-amidino-3-amino-4-biphenylyl)-3-(2-carboxy-ethyl)-imidazolidin-2-one

(19) 1-(3-acetamino-4'-amidino-4-biphenylyl)-3-(2-carboxy-ethyl)-imidazolidin-2-one

(20) 1-(4'-amidino-3-benzoylamino-4-biphenylyl)-3-(2-carboxy-ethyl)-imidazolidin-2-one

(21) 2-(4'-amidino-4-biphenylyl)-5-(2-carboxy-ethyl)-3,4-dihydro-2H,5H-1,2,5-thiadiazol-1,1-dioxide Melting point: above 260° C.
$R_f$ value: 0.63 (Reversed Phase Plate RP8; methanol/10% sodium chloride solution=6:4)
Calc.: C 55.66 H 5.19 N 14.42 S 8.25
Found: 54.42 5.32 14.56 8.26

(22) 1-[4-(4-amidino-phenyl)-cyclohexyl]-3-(2-carboxy-ethyl)-3H-imidazol-2-one

(23) 1-[4-(4-amidino-phenyl)-cyclohexyl]-3-(2-carboxy-ethyl)-imidazolidin-2-one

(24) 1-[1-(4-amidino-phenyl)-4-piperidinyl]-3-(2-carboxy-ethyl)-imidazolidin-2-one Melting point: above 275° C.
$R_f$ value: 0.66 (Reversed Phase Plate RP8; methanol/10% sodium chloride solution=6:4)
Calc.×0.5 H$_2$O: C 58.68 H 7.11 N 19.01
Found: 58.16 7.22 18.76

(25) 1-[4-(5-amidino-2-pyridyl)-phenyl]-3-(2-carboxy-ethyl)-imidazolidin-2-one

(26) 1-[4-(5-amidino-2-pyrazinyl)-phenyl]-3-(2-carboxy-ethyl)-imidazolidin-2-one

(27) 1-[4-(5-amidino-2-pyrimidinyl)-phenyl]-2-(2-carboxy-ethyl)-imidazolidin-2-one

(28) 1-[6-(4-amidino-phenyl)-3-pyridazinyl]-3-(2-carboxy-ethyl)-imidazolidin-2-one Melting point: from 300° C. (decomp.)
$R_f$ value: 0.47 (silica gel; butanol/glacial acetic acid/water=4:1:1)

(29) 1-[2-(4-amidino-phenyl)-5-pyrimidinyl]-3-(2-carboxy-ethyl)-imidazolidin-2-one

(30) 1-[2-(4'-amidino-4-biphenyl)-ethyl]-3-carboxymethyl-imidazolidin-2-one

(31) 1-(4-amidino-3-fluoro-phenyl)-3-[4-(2-carboxy-ethyl)-phenyl]-imidazolidin-2-one

(32) 1-(4-amidino-3-chloro-phenyl)-3-[4-(2-carboxy-ethyl)-phenyl]-imidazolidin-2-one

(33) 1-(4-amidino-2-methylthio-phenyl)-3-[4-(2-carboxy-ethyl)-phenyl]-imidazolidin-2-one
(34) 1-(4-amidino-2-methylsulphinyl-phenyl)-3-[4-(2-carboxy-ethyl)-phenyl]-imidazolidin-2-one
(35) 1-(4-amidino-2-methylsulphonyl-phenyl)-3-[4-(2-carboxy-ethyl)-phenyl]-imidazolidin-2-one
(36) 1-(4-amidino-2-methyl-phenyl)-3-[4-(2-carboxy-ethyl)-phenyl]-imidazolidin-2-one Melting point: above 270° C.
$R_f$ value: 0.56 (Reversed Phase Plate RP8; methanol/5% sodium chloride solution=6:4)
Calc.: C 65.56 H 6.05 N 15.29
Found: 65.43 6.04 15.36

(37) 1-(4-amidino-2-methoxy-phenyl)-3-[4-(2-carboxy-ethyl)-phenyl]-imidazolidin-2-one
(38) 1-(4-amidino-phenyl)-3-[4-(2-carboxy-ethyl)-2-fluoro-phenyl]-imidazolidin-2-one
(39) 1-(4-amidino-phenyl)-3-[4-(2-carboxy-ethyl)-2-chloro-phenyl]-imidazolidin-2-one
(40) 1-(4-amidino-phenyl)-3-[4-(2-carboxy-ethyl)-2-methoxy-phenyl]-imidazolidin-2-one
(41) 1-(4-amidino-phenyl)-3-[4-(2-carboxy-ethyl)-2-methyl-phenyl]-imidazolidin-2-one
(42) 1-(4-amidino-phenyl)-3-[4-(2-carboxy-ethyl)-2-methylthio-phenyl]-imidazolidin-2-one
(43) 1-(4-amidino-phenyl)-3-[4-(2-carboxy-ethyl)-2-methylsulphinyl-phenyl]-imidazolidin-2-one
(44) 1-(4-amidino-phenyl)-3-[4-(2-carboxy-ethyl)-2-methylsulphonyl-phenyl]-imidazolidin-2-one
(45) 1-(4-amidino-phenyl)-3-[5-(2-carboxy-ethyl)-2-pyridyl]-imidazolidin-2-one
(46) 1-(4-amidino-phenyl)-3-[4-(2-carboxy-ethyl) cyclohexyl]-imidazolidin-2-one Melting point: above 200° C.
$R_f$ value: 0.59 (Reversed Phase Plate RPS; methanol/5% sodium chloride solution=6:4)
Calc.×0.4 H$_2$O: C 62.41 H 7.38 N 15.32
Found: 62.43 7.31 15.18

(47) 1-(4-amidino-phenyl)-3-(4-carboxymethyloxy-phenyl)-imidazolidin-2-one
(48) 1-(4-amidino-phenyl)-3-(4-carboxymethylthio-phenyl)-imidazolidin-2-one Melting point: above 275° C.
$R_f$ value: 0.56 (Reversed Phase Plate RPS; methanol/10% sodium chloride solution=6:4)
Calc.×0.5 H$_2$O: C 56.98 H 5.05 N 14.76 S 8.45
Found: 56.94 5.15 14.98 8.42

(49) 1-(4-amidino-phenyl)-3-(4-carboxymethylsulphinyl-phenyl)-imidazolidin-2-one Melting point: 252°–254° C. (decomp.)
$R_f$ value: 0.79 (Reversed Phase Plate RP8; methanol/10% sodium chloride solution=6:4)
Calc.×1.5 H$_2$O: C 52.28 H 5.12 N 13.55 S 7.74
Found: 52.34 4.97 13.62 8.26

(50) 1-(4-amidino-phenyl)-3-(4-carboxymethylsulphonyl-phenyl)-imidazolidin-2-one Melting point: above 260° C.
$R_f$ value: 0.82 (Reversed Phase Plate RP8; methanol/10% sodium chloride solution=6:4)
Calc.×0.5 H$_2$O: C 52.55 H 4.66 N 13.62 S 7.78
Found: 52.88 4.83 13.67 7.99

(51) 1-(4-amidino-phenyl)-3-[4-(3-carboxy-2-methyl-propyl)-phenyl]-imidazolidin-2-one
Lithium hydroxide was used.

Melting point: above 260° C.
$R_f$ value: 0.76 (Reversed Phase Plate RP8; methanol/10% sodium chloride solution=6:4)

(52) 1-(4-amidino-phenyl)-3-[4-(2-carboxy-2-methyl-propyl)-phenyl]-imidazolidin-2-one
(53) 1-(4-amino-cyclohexyl)-3-[4-[(2-carboxy-ethyl)-aminocarbonyl]-phenyl]-imidazolidin-2-one
(54) 4-(4'-amidino-4-biphenyl)-1-(2-carboxy-ethyl)-3-phenyl-imidazolidin-2-one
(55) 1-(4-amidino-phenyl)-3-[2-(4-carboxyphenyl)-ethyl]-imidazolidin-2-one The work was done with lithium hydroxide and a 2:1 mixture of methanol and dioxane.
Melting point: 320°–325° C. (decomp.)
$R_f$ value: 0.55 (Reversed Phase Plate RPS; methanol/5% sodium chloride solution=6:4)

(56) 1-(4-amidino-phenyl)-3-[4-(2-carboxy-ethenyl)-phenyl]-imidazolidin-2-one
(57) 1-(5-amidino-2-pyridyl)-3-[4-(2-carboxy-ethyl)-phenyl]-imidazolidin-2-one
(58) 1-(1-amidino-4-piperidinyl)-3-[4-(2-carboxy-ethyl)-phenyl]-imidazolidin-2-one
(59) 1-(4-aminomethyl-phenyl)-3-[4-(2-carboxy-ethyl)-phenyl]-imidazolidin-2-one Melting point: above 260° C.
$R_f$ value: 0.61 (Reversed Phase Plate RPS; methanol/10% sodium chloride solution=6:4)
Calc.×H$_2$O: C 63.85 H 6.49 N 11.76
Found: 64.17 6.50 11.59

(60) 1-(4-amidino-phenyl)-3-[4-(2-carboxy-ethyl)-phenyl]-imidazolidin-2-thione
(61) 1-(4-amidino-phenyl)-3-[4-(2-carboxy-ethyl)-phenyl]-2-imino-imidazolidine
(62) 1-(4-amidino-phenyl)-3-[4-(2-carboxy-ethyl)-phenyl]-imidazolidin-2,4-dione Lithium hydroxide was used
Melting point: above 260° C.
$R_f$ value: 0.83 (Reversed Phase Plate RPS; methanol/10% sodium chloride solution=6:4)
Calc.×0.5 H$_2$O: C 60.79 H 5.10 N 14.93
Found: 60.69 5.04 15.12

(63) 3-(4-amidino-phenyl)-1-[4-(2-carboxy-ethyl)-phenyl]-imidazolidin-2,4-dione
(64) 1-(4-amidino-phenyl)-3-[4-(2-carboxy-ethyl)-phenyl]-4,4-dimethyl-imidazolidin-2,5-dione
(65) 3-(4-amidino-phenyl)-1-[4-(2-carboxy-ethyl)-phenyl]-4,4-dimethyl-imidazolidin-2,5-dione
(66) 2-(4-amidino-phenyl)-5-[4-(2-carboxy-ethyl)-phenyl]-3,4-dihydro-2H,5H-1,2,5-thiadiazole-1,1-dioxide Melting point: above 275° C.
$R_f$ value: 0.53 (Reversed Phase Plate RPS; methanol/10% sodium chloride solution=6:4)
Calc.: C 55.66 H 5.19 N 14.42 S 8.25
Found: 55.84 5.24 14.23 8.01

(67) 1-(4-amidino-phenyl)-3-[4-(2-carboxy-ethyl)-phenyl]-3H-imidazol-2-one

Lithium hydroxide was used.
Melting point: above 260° C.
$R_f$ value: 0.58 (Reversed Phase Plate RPS; 10% sodium chloride solution/methanol=4:6)

(68) 1-(4-amidino-phenyl)-3-[4-(2-carboxy-ethyl)-phenyl]-2-methylimino-imidazolidine
(69) 1-(4-amidino-phenyl)-3-[4-(2-carboxy-ethyl)-phenyl]-2-phenylimino-imidazolidine

(70) 1- (4-amidino-phenyl) -3-[4-(2-carboxy-ethyl)-phenyl ]-2 - (3-pyridylimino)-imidazolidine

(71) 3- (4-amidino-phenyl)-1-[4-(2-carboxy-ethyl)-phenyl]-4-trifluoromethyl-3H-imidazol-2 -one

(72) 1- (4-amidino-phenyl)-3-[4-(2-carboxy-ethyl)-phenyl]-4-phenyl-3H-imidazol-2-one

(73) 1- (4-amidino-phenyl)-3-[4-(2-carboxy-ethyl)-phenyl]-4-phenyl-imidazolidin-2-one

(74) 1-[(4-amidino-phenyl)-carbonylmethyl]-3-(3-carboxy-propyl)-imidazolidin-2-one

(75) 1-[2-(4-amidino-phenyl)-ethyl]-3-(3-carboxy-propyl)-imidazolidin-2-one

(76) 1-[2-(4-amidino-phenyl)-2-hydroxy-ethyl]-3-(3-carboxy-propyl)-imidazolidin-2-one

(77) 1-(4-amidino-phenyl)-3-(4-carboxy-butyl)-imidazolidin-2-one $R_f$ value: 0.50 (silica gel; n-butanol/glacial acetic acid/water=4:1:1)

(78) 1-(4-amidino-phenyl)-3-(2-carboxymethylthio-ethyl)-imidazolidin-2-one

(79) 1-(4-amidino-phenyl)-3-(2-carboxymethylsulphinyl-ethyl)-imidazolidin-2-one

(80) 1-(4-amidino-phenyl)-3-(2-carboxymethylsulphonyl-ethyl)-imidazolidin-2-one

(81) 1-(4-amidino-phenyl)-3-(2-carboxymethyloxy-ethyl)-imidazolidin-2-one

(82) 1-(4-amidino-phenyl)-3-(2-carboxymethylamino-ethyl)-imidazolidin-2-one

Lithium hydroxide was used.
Melting point: 298° C. (decomp. sintering from 285° C.)
$R_f$ value: 0.14 (silica gel; methanol/2N ammonia=5:1, developing three times)

(83) 1-[2-(N-acetyl-N-carboxymethyl-amino)-ethyl]-3-(4-amidino-phenyl)-imidazolidin-2-one

(84) 1-(4-amidino-phenyl)-3-[2-(N-benzoyl-N-carboxymethylamino)-ethyl]-imidazolidin-2-one

(85) 1-(4-amidino-phenyl)-3-[1-(2-carboxy-ethyl)-2-oxo-1H-4-pyridyl]-imidazolidin-2-one

(86) 1-[4-(2-carboxy-ethyl)-phenyl]-3-(4-ethoxycarbonyl-amidino-phenyl)-imidazolidin-2-one

(87) 1-(4-amidino-phenyl)-3-[4-(3-carboxy-propyl)-phenyl]-imidazolidin-2-one

(88) 1-(4'-amidino-3-methanesulphonylamino-4-biphenylyl)-3-(2-carboxy-ethyl)-imidazolidin-2-one

(89) 1-(4-amidino-phenyl)-3-[4-(2-carboxy-ethyl)-phenyl]-4H-1,2,4-triazol-5-one

(90) 1-(4-amidino-phenyl)-3-[4-(2-carboxy-ethyl)-phenyl]-4-methyl-4H-1,2,4-triazol-5-one

(91) 3-(4-amidino-phenyl)-1-[4-(2-carboxy-ethyl)-phenyl]-4H-1,2,4-triazol-5-one

(92) 3-(4-amidino-phenyl)-1-[4-(2-carboxy-ethyl)-phenyl]-4-methyl-4H-1,2,4-triazol-5-one

(93) 4-(4-amidino-phenyl)-1-[4-(2-carboxy-ethyl)-phenyl-3H-imidazol-2-one

(94) 4-(4-amidino-phenyl)-1-[4-(2-carboxy-ethyl)-phenyl]-3-phenyl-3H-imidazol-2-one hydrochloride Lithium hydroxide was used.
Melting point: 288°–294° C. (decomp.)

(95) 4-(4-amidino-phenyl)-1-[4-(2-carboxy-ethyl)-phenyl]-3-phenyl-3H-imidazol-2-one

(96) 4-(4-amidino-phenyl)-1-[4-(2-carboxy-ethyl)-phenyl]-3H-imidazol-2-thione

(97) 4-(4-amidino-phenyl)-1-[4-(2-carboxy-ethyl)-phenyl]-3-methyl-3H-imidazol-2-thione

(98) 4-(4-amidino-phenyl)-1-[4-(2-carboxy-ethyl)-phenyl]-3-phenyl-3H-imidazol-2-thione

(99) 4-(4-amidino-phenyl)-1-[4-(2-carboxy-ethyl)-phenyl]-5-methyl-3H-imidazol-2-one (100) 4-(4-amidino-phenyl)-1-[4-(2-carboxy-ethyl)-phenyl]-3,5-dimethyl-3H-imidazol-2-one (101) 4-(4-amidino-phenyl)-1-[4-(2-carboxy-ethyl)-phenyl]-5-methyl-3-phenyl-3H-imidazol-2-one (102) 4-(4-amidino-phenyl)-1-[4-(2-carboxy-ethyl)-phenyl ]-imidazolidin-2-one (103) 4-(4-amidino-phenyl)-1-[4-(2-carboxy-ethyl)-phenyl]-3-methyl-imidazolidin-2-one (104) 4-(4-amidino-phenyl)-1-[4-(2-carboxy-ethyl)-phenyl]-3-phenyl-imidazolidin-2-one (105) 1-(4-amidino-phenyl)-4-[4-(2-carboxy-ethyl)-phenyl]-3H-imidazol-2-one (106) 1-(4-amidino-phenyl)-4-[4-(2-carboxy-ethyl)-phenyl]-3-methyl-3H-imidazol-2-one (107) 1-(4-amidino-phenyl)-4-[4-(2-carboxy-ethyl)-phenyl]-3-phenyl-3H-imidazol-2-one (108) 1-(4-amidino-phenyl)-4-[4-(2-carboxy-ethyl)-phenyl]-3H-imidazol-2-thione (109) 1-(4-amidino-phenyl)-4-[4-(2-carboxy-ethyl)-phenyl]-3-methyl-3H-imidazol-2-thione (110) 1-(4-amidino-phenyl)-4-[4-(2-carboxy-ethyl)-phenyl]-3-phenyl-3H-imidazol-2-thione (111) 1-(4-amidino-phenyl)-4-[4-(2-carboxy-ethyl)-phenyl]-5-methyl-3-phenyl-3H-imidazol-2-one (112) 1-(4-amidino-phenyl)-4-[4-(2-carboxy-ethyl)-phenyl]-3,5-dimethyl-3H-imidazol-2-one (113) 1-(4-amidino-phenyl)-4-[4-(2-carboxy-ethyl)-phenyl]-5-methyl-3H-imidazol-2-one (114) 1-(4-amidino-phenyl)-4-[4-(2-carboxy-ethyl)-phenyl]-imidazolidin-2-one (115) 1-(4-amidino-phenyl)-4-[4-(2-carboxy-ethyl)-phenyl]-3-methyl-imidazolidin-2-one (116) 1-(4-amidino-phenyl)-4-[4-(2-carboxy-ethyl)-phenyl]-3-phenyl-imidazolidin-2-one (117) 4-(4'-amidino-4-biphenylyl)-1-(2-carboxy-ethyl)-3H-imidazol-2-one hydrochloride Melting point: above 280° C.
Calc.×H$_2$O: C 56.35 H 5.48 N 13.84 Cl 8.76
Found: 56.56 5.31 13.82 8.96

(118) 4-(4'-amidino-4-biphenylyl)-1-(2-carboxy-ethyl)-3-methyl-3H-imidazol-2-one hydrochloride Melting point: above 280° C.
Calc.×H$_2$O: C 57.34 H 5.53 N 13.37 Cl 8.46
Found: 57.37 5.91 13.39 8.79

(119) 4- (4'-amidino-4-biphenylyl)-1-(2-carboxy-ethyl)-3-phenyl-3H-imidazol-2-one hydrochloride Melting point: above 280° C.
Calc.×H$_2$O: C 62.43 H 5.24 N 11.65 Cl 7.37
Found: 62.66 5.14 11.83 7.67

(120) 4-(4'-amidino-4-biphenylyl)-1-(2-carboxy-ethyl)-3H-imidazol-2-thione (121) 4-(4'-amidino-4-biphenylyl)-1-(2-carboxy-ethyl)-3-methyl-3H-imidazol-2-thione (122) 4-(4'-amidino-4-biphenylyl)-1-(2-carboxy-ethyl)-3-phenyl-3H-imidazol-2-thione (123) 4-(4'-amidino-4-biphenylyl)-1-(2-carboxy-ethyl)-5-methyl-3H-imidazol-2-one (124) 4-(4'-amidino-4-biphenylyl)-1-(2-carboxy-ethyl)-3,5-dimethyl-3H-imidazol-2-one (125) 4-(4'-amidino-4-biphenylyl)-1-(2-carboxy-ethyl)-5-methyl-3-phenyl-3H-imidazol-2-one (126) 4-(4'-amidino-4-biphenylyl)-1-(2-carboxy-ethyl)-imidazolidin-2-one (127) 4-(4'-amidino-4-biphenylyl)-1-(2-carboxy-ethyl)-3-methyl-imidazolidin-2 -one (128) 1-[4-(2-carboxy-ethyl)-phenyl]-3-(3-guanidino-phenyl)-imidazolidin-2-one (129) 1-(4-amidino-phenyl)-3-[1-(2-carboxy-ethyl)-4-piperidinyl]-imidazolidin-2-one (130) 1-[4-(2-carboxy-ethyl)-phenyl]-3-(4-methylamidino-phenyl)-imidazolidin-2-one (131) 1-(4-n-butylamidino-phenyl)-3-[4-(2-carboxy-ethyl)-phenyl]-imidazolidin-2-one (132) 2-(4-amidino-4'-biphenylyl)-4-(2-carboxy-ethyl)-4H-1,2,4-triazol-3-one (133) 2-(4-amidino-4'-biphenylyl)-4-(2-carboxy-ethyl)-5-methyl-4H-1,2,4-triazol-3-one (134) 4-(4-amidino-4'-biphenylyl)-2-(2-carboxy-ethyl)-4H-1,2,4-triazol-3-one (135) 4-(4-amidino-4'-biphenylyl)-2-(2-carboxy-ethyl)-5-methyl-4H-1,2,4-triazol-3-one (136) 3-(4-amidino-phenyl)-1-(4-carboxy-butyl)-3H-imidazo[4,5-b]pyridin-2-one hydrochloride $R_f$ value: 0.23 (silica gel; methylene chloride/methanol= 19:1)

(137) 4-(4-amidino-phenyl)-2-[4-(2-carboxy-ethyl)-phenyl]-5-methyl-4H-1,2,4-triazol-3-one $R_f$ value: 0.60 (Reversed Phase Plate RP8; methanol/5% sodium chloride solution=6:4)

(138) 1-(4-amidino-phenyl)-3-[4-(2-carboxy-ethyl)-phenyl]-4-methyl-3H-imidazol-2-one $R_f$ value: 0.54 (Reversed Phase Plate RP8; methanol/5% sodium chloride solution=6:4)

Calc.×1.8 H$_2$O: C 60.54 H 5.99 N 14.12
Found: 60.95 5.88 14.15

(139) 2-(4-amidino-phenyl)-4-[4-(2-carboxy-ethyl)-phenyl]-5-methyl-4H-1,2,4-triazol-3-one Melting point: 303°–305° C.
$R_f$ value: 0.63 (Reversed Phase Plate RP8; methanol/5% sodium chloride solution=6:4)
Calc.: C 62.45 H 5.24 N 19.17
Found: 62.28 5.28 18.70

(140) 2-(4-amidino-phenyl)-4-[4-(2-carboxy-ethyl)-phenyl]-5-ethyl-4H-1,2,4-triazol-3-one Melting point: above 250° C.
$R_f$ value: 0.53 (Reversed Phase Plate RPS; methanol/10% sodium chloride solution=6:4)
Calc.×1.5 H$_2$O: C 59.10 H 5.95 N 17.23
Found: 58.71 6.10 17.03

(141) 1-(4-aminomethyl-phenyl)-3-(4-carboxymethyloxy-phenyl)-imidazolidin-2-one

Melting point: above 250° C.
$R_f$ value: 0.58 (Reversed Phase Plate RP8; methanol/5% sodium chloride solution=6:4)
Calc.×0.5 H$_2$O: C 61.70 H 5.75 N 11.99
Found: 61.48 5.81 12.22

(142) 1-(4-aminomethyl-phenyl)-3-[4-(2-carboxy-ethyl)-phenyl]-3,4,5,6-tetrahydro-1H-pyrimidin-2-one Melting point: 229°–231° C.
$R_f$ value: 0.56 (Reversed Phase Plate RPS; methanol/10% sodium chloride solution=6:4)

(143) 3-(4'-amidino-4-biphenylyl)-1-(2-carboxy-ethyl)-3H-imidazo[4,5-b]pyridin-2-one $R_f$ value: 0.28 (silica gel; methylene chloride/methanol=8:2)

(144) 3-(4-amidino-phenyl)-1-[4-(2-carboxy-ethyl)-phenyl]-4-methyl-3H-imidazol-2-one $R_f$ value: 0.54 (Reversed Phase Plate RP8; methanol/5% sodium chloride solution=6:4)

(145) 2-(4-amidino-phenyl)-4-[4-(2-carboxy-ethyl)-phenyl]-4H-1,2,4-triazol-3-one Melting point: 310°–313° C.
$R_f$ value: 0.58 (Reversed Phase Plate RP8; methanol/5% sodium chloride solution=6:4)
Calc.: C 59.99 H 5.03 N 19.44
Found: 60.03 5.04 19.15

(146) 4-(4-amidino-phenyl)-2-[4-(2-carboxy-ethyl)-phenyl]-4H-1,2,4-triazol-3-one Melting Point: 313°–316° C.
$R_f$ value: 0.61 (Reversed Phase Plate RP8; methanol/5% sodium chloride solution=6:4)
Calc.: C 61.53 H 4.88 N 19.93
Found: 61.42 4.97 20.22

(147) 1-(4-amidino-phenyl)-3-[4-(2-carboxy-ethenyl)-phenyl]-3H-imidazol-2-one

Melting point: above 350° C.
$R_f$ value: 0.45 (Reversed Phase Plate RPS; methanol/10% sodium chloride solution=6:4)

(148) 1-(4-amidino-phenyl)-3-[4-(2-amino-2-carboxy-ethyl)-phenyl]-3H-imidazol-2-one Lithium hydroxide was used.
$R_f$ value: 0.06 (silica gel; methylene chloride/methanol/conc. ammonia=8:4:1)

(149) 1-[4-(2-amino-2-carboxy-ethyl)-phenyl]-3-(4-aminomethyl-phenyl)-imidazolidin-2-one Lithium hydroxide was used.
$R_f$ value: 0.15 (silica gel; methylene chloride/methanol/conc. ammonia=16:4:1)

(150) 1-(4-amidino-phenyl)-3-[4-(2-carboxy-2-dibenzylamino-ethyl)-phenyl]-3H-imidazol-2-one Lithium hydroxide was used.
$R_f$ value: 0.50 (silica gel; methylene chloride/methanol=4:1)

(151) 1-[4-(2-amino-ethyl)-phenyl]-3-(4-carboxymethyl-phenyl)-imidazolidin-2-one Melting point: above 250° C.
$R_f$ value: 0.41 (Reversed Phase Plate RPS; methanol/5% sodium chloride solution=6:4)

(152) 1-[4-(2-amino-2-propyl)-phenyl]-3-[4-(2-carboxyethyl)-phenyl)-imidazolidin-2-one (153) 1-[4-(1-amino-ethyl)-phenyl]-3-[4-(2-carboxy-ethyl)-phenyl]-imidazolidin-2-one Melting point: 267°–269° C. (decomp.)
$R_f$ value: 0.40 (Reversed Phase Plate RP8; methanol/5% sodium chloride solution=6:4)

(154) 1-(1-amino-5-indanyl)-3-[4-(2-carboxy-ethyl)-phenyl]-imidazolidin- 2-one

Melting point: 234°–236° C. (decomp.)

(155) 1-(1-amino-1,2,3,4-tetrahydro-6-naphthyl)-3-[4-(2-carboxy-ethyl)-phenyl]-imidazolidin-2-one (156) 1-(4-aminomethyl-2-methyl-phenyl)-3-[4-(2-carboxy-ethyl)-phenyl]-imidazolidin-2-one Melting point: 237°–239° C. (decomp.)
$R_f$ value: 0.50 (Reversed Phase Plate RP8; methanol/5% sodium chloride solution=6:4)
Calc.×0.8 H$_2$O: C 65.31 H 6.74 N 11.42
Found: 65.31 6.68 11.43

(157) 1-(4-amidino-phenyl)-3-[4-(2-carboxy-2-dimethylamino-ethyl)-phenyl]-3H-imidazol-2-one (158) 1-(4-amidino-phenyl)-3-[4-(2-carboxy-1-carboxymethyl-ethyl)-phenyl]-imidazolidin-2-one (159) 1-(4-amidino-phenyl)-3-[3,4-bis-carboxymethyloxy-phenyl]-imidazolidin-2-one (160) 3-(4-aminomethyl-phenyl)-1-[4-(2-carboxy-ethyl)-phenyl]-4-methyl-3H-imidazol-2-one (161) 1-(4-amino-cyclohexyl)-3-[4-(3-carboxy-propyl)-phenyl]-imidazolidin-2-one (162) 1-(4-amino-cyclohexyl)-3-[4-(2-carboxy-ethyl)-phenyl]-imidazolidin-2-one (163) 1-(4'-aminomethyl-4-biphenylyl)-3-(2-carboxy-ethyl)-imidazolidin-2-one (164) 1-(4-aminomethyl-3-fluoro-phenyl)-3-[4-(2-carboxy-ethyl)-phenyl]-imidazolidin-2-one (165) 1-(4-amidino-phenyl)-3-[4-(2-carboxy-ethyl)-phenyl]-4-methyl-imidazolidin-2-one (166) 1-(4-aminomethyl-phenyl)-3-[3-(2-carboxy-ethyl)-phenyl]-imidazolidin-2-one (167) 1-(4-aminomethyl-phenyl)-3-[4-(2-carboxyl-1-carboxymethyl-ethyl)-phenyl]-imidazolidin-2-one (168) 4-(4-aminomethyl-phenyl)-2-[4-(2-carboxy-ethyl)-phenyl]-4H-1,2,4-triazol-3-one (169) 1-[4-(2-amino-ethyl)-phenyl]-3-[4-(2-carboxy-ethyl)-phenyl]-imidazolidin-2-one Half concentrated hydrochloric acid was used at room temperature
Melting point: above 250° C.
$R_f$ value: 0.57 (Reversed Phase Plate RP8, glacial acetic acid/water=4:6)

(170) 1-[4-(1-amino-2-methyl-2-propyl)-phenyl]-3-[4-(2-carboxy-ethyl)-phenyl]-imidazolidin-2-one (171) 1-[4-[(2-carboxy-ethyl)-aminocarbonyl]-phenyl]-3-(4-piperidinyl)-imidazolidin-2-one (172) 1-[4-(2-carboxy-ethyl)-phenyl]-3-[4-(dimethylamino-methyl)-phenyl]-imidazolidin-2-one (173) 1-[4-(2-carboxy-ethyl)-phenyl]-3-[4-(methylamino-methyl)-phenyl]-imidazolidin-2-one (174) 1-[4-(2-carboxy-ethyl)-phenyl]-3-[4-(n-propylamino-methyl)-phenyl]-imidazolidin-2-one (175) 2-(4-aminomethyl-phenyl)-4-[4-(2-carboxy-ethyl)-phenyl]-5-methyl-4H-1,2,4-triazol-3-one (176) 1-[4-(1-amino-cyclopropyl)-phenyl]-3-[4-(2-carboxy-ethyl)-phenyl]-imidazolidin-2-one (177) 1-[4-(1-amino-cyclopentyl)-phenyl]-3-[4-(2-carboxy-ethyl)-phenyl]-imidazolidin-2-one (178) 1-(4-amidino-phenyl)-3-[4-(2-amino-2-carboxy-ethyl)-phenyl]-imidazolidin-2-one Lithium hydroxide was used.
$R_f$ value: 0.07 (silica gel; methylene chloride/methanol/conc. ammonia=8:4:1)

(179) 1-(4-amidino-phenyl)-3-[4-(2-carboxy-2-hydroxy-ethyl)-phenyl]-3H-imidazol-2-one (180) 1-(4-amidino-phenyl)-3-[4-(2-carboxy-2-methoxy-ethyl)-phenyl]-3H-imidazol-2-one (181) 1-[4-(2-amino-ethyl)-phenyl]-3-(4-carboxymethyloxy-phenyl)-imidazolidin-2-one The hydrochloride of the ethylester was refluxed in water.
Melting point: above 350° C.
$R_f$ value: 0.42 (Reversed Phase Plate RP8; methanol/5% sodium chloride solution=6:4)

(182) 1-[3-(2-amino-ethyl)-phenyl]-3-[4-(2-carboxy-ethyl)-phenyl]-imidazolidin-2-one
Melting point: above 250° C.

$R_f$ value: 0.42 (Reversed Phase Plate RP8; methanol/5% sodium chloride=6:4)
Calc.×0.3 H$_2$O: C 66.95 H 6.63 N 11.71
Found: 66.64 6.65 11.82

(183) 1-[4-[(2-carboxy-ethyl)-aminocarbonyl]-phenyl]-3-(1-methyl-4-piperidinyl)-imidazolidin-2-one (184) 1-(4-aminomethyl-cyclohexyl)-3-[4-(2-carboxy-ethyl)-phenyl]-imidazolidin-2-one (185) 2-(4-amidino-phenyl)-4-[4-(2-carboxy-2-methyl-propyl)-phenyl]-5-methyl-4H-1,2,4-triazol-3-one (186) 2-(4-amidino-phenyl)-4-[4-(2-carboxy-ethyl)-phenyl]-5-trifluoromethyl-4H-1,2,4-triazol-3-one (187) 2-(4-amidino-phenyl)-4-[4-(2-carboxy-ethyl)-phenyl]-5-phenyl-4H-1,2,4-triazol-3-one Example 2

1-(4'-Amidino-4-biphenylyl)-3-methoxycarbonylmethyl-imidazolidin-2-one hydrochloride 85 ml of an ice-cooled saturated solution of hydrogen chloride in methanol were added to 3.1 g of 1-(4'-cyano-4-biphenylyl)-3-methoxycarbonylmethyl-imidazolidin-2-one. The resulting suspension was covered with petroleum ether and stirred for 3.5 hours at ambient temperature. The mixture was evaporated to dryness and dried for a further 15 minutes at 1 mbar. The residue was suspended in 80 ml of absolute methanol, 2.7 g of ammonium carbonate were added and the resulting mixture was stirred for 16 hours at ambient temperature. The precipitate was filtered off, the mother liquor was evaporated down and the residue was purified by column chromatography on silica gel (eluant: methylene chloride/methanol/conc. ammonia=3:1:0.2).
Yield: 0.7 g (20% of theory),
Melting point: above 200° C.
$R_f$ value: 0.53 (silica gel; methylene chloride/methanol/conc. ammonia=3:1:0.2)

The following compounds were obtained analogously:

(1) 1-(4'-amidino-4-biphenylyl)-3-(2-methoxycarbonyl-ethyl)-imidazolidin-2-one hydrochloride A four-fold excess of ammonium chloride was used, refluxing for 6 hours.
Melting point: above 200° C.
$R_f$ value: 0.40 (silica gel; methylene chloride/methanol/conc. ammonia=5:1:0.2)

(2) 1-(4'-amidino-4-biphenylyl)-3-(2-ethoxycarbonyl-ethyl)-imidazolidin-2,4-dione hydrochloride Ethanolic hydrochloric acid was used in the first phase of the reaction. In the reaction with ammonium carbonate, the mixture was heated to 50° C. for 4 hours. For purification the evaporation residue was stirred with water.
Melting point: above 200° C.
$R_f$ value: 0.50 (silica gel; methylene chloride/methanol=4:1)
Calc.:×HCl×H$_2$O: C 56.18 H 5.61 N 12.48 Cl 7.90
Found: 56.41 5.70 12.29 7.78

(3) 1-(4'-amidino-4-biphenylyl)-3-(2-ethoxycarbonyl-ethyl)-3H-imidazol-2-one hydrochloride In the first phase of the reaction ethanolic hydrochloric acid was used. In the reaction with ammonium carbonate ethanol was used as solvent.
Melting point: above 200° C.
$R_f$ value: 0.27 (silica gel; methylene chloride/methanol conc. ammonia=3:1:0.2)
Calc.×1.2 HCl×H$_2$O: C 57.30 H 5.77 N 12.73 Cl 9.66
Found: 57.36 5.83 12.38 9.26

(4) 1-(4'-amidino-4-biphenylyl)-3-(2-ethoxycarbonyl-ethyl)-3,4,5,6-tetrahydro-1H-pyrimidin-2-one hydrochloride In the first phase of the reaction ethanolic hydrochloric acid was used. In the reaction with ammonium carbonate the mixture was heated to 50° C. for 4 hours. For purification the evaporation residue was stirred with water.

Melting point: 212°–215° C.

$R_f$ value: 0.47 (silica gel; methylene chloride/methanol conc. ammonia=3:1:0.2)

Calc.×HCl: C 61.32 H 6.32 N 13.00 Cl 8.23
Found: 60.71 6.40 12.85 8.04

(5) 1-(4'-amidino-4-biphenylyl)-3-methoxycarbonylmethyl-3,4,5,6-tetrahydro-1H-pyrimidin-2-one hydrochloride Melting point: above 200° C.

$R_f$ value: 0.50 (silica gel; methylene chloride/methanol conc. ammonia=3:1:0.2)

(6) 1-(4-amidino-phenyl)-3-[4-(2-methoxycarbonyl-ethyl)-phenyl]-imidazolidin-2-one hydrochloride Melting point: from 260° C. (decomp.)

The product was also obtained by reacting 1-(4-amidino-phenyl)-3-[4-(2-carboxy-ethyl)-phenyl]-imidazolidin-2-one with methanolic hydrochloric acid.

$R_f$ value: 0.49 (Reversed Phase Plate RP8; 10% sodium chloride solution/methanol=4:6)

(7) 1-(4-amidino-phenyl)-3-[4-(2-methoxycarbonyl-ethyl)-phenyl]-3,4,5,6-tetrahydro-1H-pyrimidin-2-one hydrochloride $R_f$ value: 0.08 (silica gel; methylene chloride/methanol=95:5)

(8) 1-[2-(4'-amidino-4-biphenylyl)-ethyl]-3-methoxycarbonylmethyl-3H-benzimidazol-2-one $R_f$ value: 0.18 (silica gel; methylene chloride/methanol=8:2)

(9) 1-(4'-amidino-3'-fluoro-4-biphenylyl)-3-(2-methoxycarbonyl-ethyl)-imidazolidin-2-one hydrochloride

(10) 1-(4'-amidino-3'-chloro-4-biphenylyl)-3-(2-methoxy-carbonyl-ethyl)-imidazolidin-2-one hydrochloride

(11) 1-(4'-amidino-3-methoxy-4-biphenylyl)-3-(2-methoxycarbonyl-ethyl)-imidazolidin-2-one hydrochloride

(12) 1-(4'-amidino-3-bromo-4-biphenylyl)-3-(2-methoxycarbonyl-ethyl)-imidazolidin-2-one hydrochloride

(13) 1-(4'-amidino-3-methylthio-4-biphenylyl)-3-(2-methoxycarbonyl-ethyl)-imidazolidin-2-one hydrochloride

(14) 1-(4'-amidino-3-methylsulphonyl-4-biphenylyl)-3-(2-methoxycarbonyl-ethyl)-imidazolidin-2-one hydrochloride

(15) 1-(4'-amidino-2,3-dimethyl-4-biphenylyl)-3-(2-methoxycarbonyl-ethyl)-imidazolidin-2-one hydrochloride

(16) 1-(4'-amidino-3-nitro-4-biphenylyl)-3-(2-methoxycarbonyl-ethyl)-imidazolidin-2-one hydrochloride

(17) 1-(4'-amidino-3-amino-4-biphenylyl)-3-(2-methoxycarbonyl-ethyl)-imidazolidin-2-one hydrochloride

(18) 1-(3-acetamino-4'-amidino-4-biphenylyl)-3-(2-methoxycarbonyl-ethyl)-imidazolidin-2-one hydrochloride

(19) 1-(4'-amidino-3-benzoylamino-4-biphenylyl)-3-(2-methoxycarbonyl-ethyl)-imidazolidin-2-one hydrochloride

(20) 2-(4'-amidino-4-biphenylyl)-5-(2-methoxycarbonyl-ethyl)-3,4-dihydro-2H,5H-1,2,5-thiadiazole-1,1-dioxide hydrochloride Melting point: 243°–245° C.

$R_f$ value: 0.43 (Reversed Phase Plate RPS; methanol/10% sodium chloride solution=6:4)

(21) 1-[4-(4-amidino-phenyl)-cyclohexyl]-3-(2-methoxycarbonyl-ethyl)-3H-imidazol-2-one hydrochloride

(22) 1-[4-(4-amidino-phenyl)-cyclohexyl]-3-(2-methoxycarbonyl-ethyl)-imidazolidin-2-one hydrochloride

(23) 1-[1-(4-amidino-phenyl)-4-piperidinyl]-3-(2-methoxycarbonyl-ethyl)-imidazolidin-2-one hydrochloride

(24) 1-[4-(5-amidino-2-pyridyl)-phenyl]-3-(2-methoxycarbonyl-ethyl)-imidazolidin-2-one hydrochloride

(25) 1-[4-(5-amidino-2-pyrazinyl)-phenyl]-3-(2-methoxycarbonyl-ethyl)-imidazolidin-2-one hydrochloride

(26) 1-[4-(5-amidino-2-pyrimidinyl)-phenyl]-3-(2-methoxycarbonyl-ethyl)-imidazolidin-2-one hydrochloride

(27) 1-[6-(4-amidino-phenyl)-3-pyridazinyl]-3-(2-methoxycarbonyl-ethyl)-imidazolidin- 2-one hydrochloride Melting point: 303°–305° C. (decomp., sintering from 240° C.)

$R_f$ value: 0.42 (silica gel; methylene chloride/methanol/conc. ammonia=8:2:0.1)

(28) 1-[2-(4-amidino-phenyl)-5-pyrimidinyl]-3-(2-methoxycarbonyl-ethyl)-imidazolidin-2-one hydrochloride

(29) 1-[2-(4'-amidino-biphenylyl)-ethyl]-3-methoxycarbonylmethyl-imidazolidin-2-one hydrochloride

(30) 1-(4-amidino-3-fluoro-phenyl)-3-[4-(2-methoxycarbonyl-ethyl)-phenyl]-imidazolidin-2-one hydrochloride

(31) 1-(4-amidino-3-chloro-phenyl)-3-[4-(2-methoxycarbonyl-ethyl)-phenyl]-imidazolidin-2-one hydrochloride

(32) 1-(4-amidino-2-methylthio-phenyl)-3-[4-(2-methoxycarbonyl-ethyl)-phenyl]-imidazolidin-2-one hydrochloride

(33) 1-(4-amidino-2-methylsulphonyl-phenyl)-3-[4-(2-methoxycarbonyl-ethyl)-phenyl]-imidazolidin-2-one hydrochloride

(34) 1-(4-amidino-2-methyl-phenyl)-3-[4-(2-methoxycarbonyl-ethyl)-phenyl]-imidazolidin-2-one hydrochloride Melting point: 143°–146° C.

$R_f$ value: 0.37 (Reversed Phase Plate RPS; methanol/5% sodium chloride solution=6:4)

(35) 1-(4-amidino-2-methoxy-phenyl)-3-[4-(2-methoxycarbonyl-ethyl)-phenyl]-imidazolidin-2-one hydrochloride

(36) 1-(4-amidino-phenyl)-3-[2-fluoro-4-(2-methoxycarbonyl-ethyl)-phenyl]-imidazolidin-2-one hydrochloride

(37) 1-(4-amidino-phenyl)-3-[2-chloro-4-(2-methoxycarbonyl-ethyl)-phenyl]-imidazolidin-2-one hydrochloride

(38) 1-(4-amidino-phenyl)-3-[2-methoxy-4-(2-methoxycarbonyl-ethyl)-phenyl]-imidazolidin-2-one hydrochloride

(39) 1-(4-amidino-phenyl)-3-[4-(2-methoxycarbonyl-ethyl)-2-methyl-phenyl]-imidazolidin-2-one hydrochloride

(40) 1-(4-amidino-phenyl)-3-[4-(2-methoxycarbonyl-ethyl)-2-methylthio-phenyl]-imidazolidin-2-one hydrochloride

(41) 1-(4-amidino-phenyl)-3-[4-(2-methoxycarbonyl-ethyl)-2-methylsulphonyl-phenyl]-imidazolidin-2-one hydrochloride

(42) 1-(4-amidino-phenyl)-3-[5-(2-methoxycarbonyl-ethyl)-2-pyridyl]-imidazolidin-2-one hydrochloride

(43) 1-(4-amidino-phenyl)-3-[4-(2-methoxycarbonyl-ethyl)-cyclohexyl]-imidazolidin-2-one hydrochloride Melting point: above 200° C.

$R_f$ value: 0.44 (Reversed Phase Plate RP8; methanol/5% sodium chloride solution=6:4)

(44) 1-(4-amidino-phenyl)-3-(4-methoxycarbonyl-methyloxy-phenyl)-imidazolidin-2-one hydrochloride

(45) 1-(4-amidino-phenyl)-3-(4-methoxycarbonyl-methylthio-phenyl)-imidazolidin-2-one Melting point: from 197° C. (decomp.)

$R_f$ value: 0.25 (Reversed Phase Plate RP8; methanol/10% sodium chloride solution=6:4)

(46) 1-(4-amidino-phenyl)-3-(4-methoxycarbonyl-methylsulphonyl-phenyl)-imidazolidin-2-one hydrochloride Melting point: from 249° C. (decomp.)

$R_f$ value: 0.43 (Silica gel; methylene chloride/methanol=8:2)

(47) 1-(4-amidino-phenyl)-3-[4-(3-methoxycarbonyl-2-methyl-2-propyl)-phenyl]-imidazolidin-2-one hydrochloride Melting point: 228°–236° C. (decomp.)

$R_f$ value: 0.19 (Silica gel; methylene chloride/methanol=9:1)

(48) 1-(4-amidino-phenyl)-3-[2-(4-methoxycarbonyl-phenyl)-ethyl]-imidazolidin-2-one Melting point: 226°–228° C. (decomp.)

$R_f$ value: 0.40 (Reversed Phase Plate RPS; methanol/5% sodium chloride solution=6:4)

(49) 1-(4-amidino-phenyl)-3-[4-(2-methoxycarbonyl-ethenyl)-phenyl]-imidazolidin-2-one hydrochloride

(50) 1-(5-amidino-2-pridyl)-3-[4-(2-methoxycarbonyl-ethyl)-phenyl]-imidazolidin-2-one hydrochloride

(51) 1-(4-amidino-phenyl)-3-[4-(2-methoxycarbonyl-ethyl)-phenyl]-imidazolidin-2-thione hydrochloride

(52) 1-(4-amidino-phenyl)-2-imino-3-[4-(2-methoxycarbonyl-ethyl)-phenyl]-imidazolidine hydrochloride

(53) 1-(4-amidino-phenyl)-3-[4-(2-methoxycarbonyl-ethyl)-phenyl]-imidazolidin-2,4-dione hydrochloride Melting point: above 260° C.

$R_f$ value: 0.19 (silica gel; methylene chloride/methanol=9:1)

Calc.: C 57.62 H 5.08 N 13.44 Cl 8.50

Found: 56.94 5.03 13.33 8.99

(54) 3-(4-amidino-phenyl)-1-[4-(2-methoxycarbonyl-ethyl)-phenyl]-imidazolidin-2,4-dione hydrochloride

(55) 1-(4-amidino-phenyl)-4,4-dimethyl-3-[4-(2-methoxycarbonyl-ethyl)-phenyl]-imidazolidin-2,5-dione hydrochloride

(56) 3-(4-amidino-phenyl)-4,4-dimethyl-1-[4-(2-methoxycarbonyl-ethyl)-phenyl]-imidazolidin-2,5-dione hydrochloride

(57) 2-(4-amidino-phenyl)-5-[4-(2-methoxycarbonyl-ethyl)-phenyl]-3,4-dihydro-2H,5H-1,2,5-thiadiazole-1,1-dioxide hydrochloride Melting point: 245°–248° C. (decomp.)

$R_f$ value: 0.44 (Reversed Phase Plate RP8; methanol/10% sodium chloride solution=6:4)

(58) 1-(4-amidino-phenyl)-3-[4-(2-methoxycarbonyl-ethyl)-phenyl]-3H-imidazol-2-one hydrochloride Melting point: 240° C. (decomp., sintering from 208° C.)

$R_f$ value: 0.33 (silica gel; methylene chloride/methanol=5:1)

(59) 1-(4-amidino-phenyl)-3-[4-(2-methoxycarbonyl-ethyl)-phenyl]-2-methylimino-imidazolidine hydrochloride

(60) 1-(4-amidino-phenyl)-3-[4-(2-methoxycarbonyl-ethyl)-phenyl]-2-phenylimino-imidazolidine hydrochloride

(61) 1-(4-amidino-phenyl)-3-[4-(2-methoxycarbonyl-ethyl)-phenyl]-2-(3-pyridyl-imino)-imidazolidine hydrochloride

(62) 3-(4-amidino-phenyl)-1-[4-(2-methoxycarbonyl-ethyl)-phenyl]-4-trifluoromethyl-3H-imidazol-2-one hydrochloride

(63) 1-(4-amidino-phenyl)-3-[4-(2-methoxycarbonyl-ethyl)-phenyl]-4-phenyl-3H-imidazol-2-one hydrochloride

(64) 1-(4-amidino-phenyl)-3-[4-(2-methoxycarbonyl-ethyl)-phenyl]-4-phenyl-3H-imidazolidin-2-one hydrochloride

(65) 1-[(4-amidino-phenyl)-carbonylmethyl]-3-(3-methoxycarbonyl-propyl)-imidazolidin-2-one hydrochloride

(66) 1-[2-(4-amidino-phenyl)-ethyl]-3-(3-methoxycarbonyl-propyl)-imidazolidin-2-one hydrochloride

(67) 1-(4-amidino-phenyl)-3-[4-(2-methoxycarbonyl-ethyl)-phenyl]-4H-1,2,4-triazol-5-one hydrochloride

(68) 1-(4-amidino-phenyl)-3-[4-(2-methoxycarbonyl-ethyl)-phenyl]-4-methyl-4H-1,2,4-triazol-5-one hydrochloride

(69) 3-(4-amidino-phenyl)-1-[4-(2-methoxycarbonyl-ethyl)-phenyl]-4H-1,2,4-triazol-5-one hydrochloride

(70) 3-(4-amidino-phenyl)-1-[4-(2-methoxycarbonyl-ethyl)-phenyl]-4-methyl-4H-1,2,4-triazol-5-one hydrochloride

(71) 1-(4-amidino-phenyl)-3-(4-methoxycarbonyl-butyl)-imidazolidin-2-one hydrochloride $R_f$ value: 0.72 (silica gel; methylene chloride/methanol=2:1)

(72) 1-(4-amidino-phenyl)-3-(2-methoxycarbonylthio-ethyl)-imidazolidin-2-one hydrochloride

(73) 1-(4-amidino-phenyl)-3-(2-methoxycarbonyl-methylsulphonyl-ethyl)-imidazolidin-2-one hydrochloride

(74) 1-(4-amidino-phenyl)-3-(2-methoxycarbonyloxy-ethyl)-imidazolidin-2-one hydrochloride

(75) 1-(4-amidino-phenyl)-3-(2-methoxycarbonyl-methylamino-ethyl)-imidazolidin-2-one hydrochloride-acetate Melting point: 197° C. (decomp., sintering from 172° C.)

$R_f$ value: 0.44 (silica gel; methylene chloride/methanol/conc. ammonia=8:2:0.1, developing twice)

(76) 1-[2-(N-acetyl-N-methoxycarbonylmethyl-amino)-ethyl]-3-(4-amidino-phenyl)-imidazolidin-2-one hydrochloride

(77) 1-(4-amidino-phenyl)-3-[2-(N-benzoyl-N-methoxycarbonylmethyl-amino)-ethyl]-imidazolidin-2-one hydrochloride

(78) 1-(4-amidino-phenyl)-3-[1-(2-methoxycarbonyl-ethyl)-2-oxo-1H-4-pyridyl]-imidazolidin-2-one hydrochloride

(79) 1-(4'-amidino-3-methanesulphonylamino-4-biphenylyl)-3-(2-methoxycarbonyl-ethyl)-imidazolidin-2-one hydrochloride

(80) 4-(4-amidino-phenyl)-1-[4-(2-methoxycarbonyl-ethyl)-phenyl]-3H-imidazol-2-one hydrochloride

(81) 4-(4-amidino-phenyl)-1-[4-(2-methoxycarbonyl-ethyl)-phenyl]-3-methyl-3H-imidazol-2-one hydrochloride Melting point: 242°–246° C. (decomp.)

$R_f$ value: 0.50 (silica gel; methylene chloride/methanol=4:1)

(82) 4-(4-amidino-phenyl)-1-[4-(2-methoxycarbonyl-ethyl)-phenyl]-3-phenyl-3H-imidazol-2-one hydrochloride

(83) 4-(4-amidino-phenyl)-1-[4-(2-methoxycarbonyl-ethyl)-phenyl]-3H-imidazol-2-thione hydrochloride

(84) 4-(4-amidino-phenyl)-1-[4-(2-methoxycarbonyl-ethyl)-phenyl]-3-methyl-3H-imidazol-2-thione hydrochloride

(85) 4-(4-amidino-phenyl)-1-[4-(2-methoxycarbonyl-ethyl)-phenyl]-3-phenyl-3H-imidazol-2-thione hydrochloride

(86) 4-(4-amidino-phenyl)-1-[4-(2-methoxycarbonyl-ethyl)-phenyl]-5-methyl-3H-imidazol-2-one hydrochloride

(87) 4-(4-amidino-phenyl)-3,5-dimethyl-1-[4-(2-methoxycarbonyl-ethyl)-phenyl]-3H-imidazol-2-one hydrochloride

(88) 4-(4-amidino-phenyl)-1-[4-(2-methoxycarbonyl-ethyl)-phenyl]-5-methyl-3-phenyl-3H-imidazol-2-one hydrochloride

(89) 4-(4'-amidino-4-biphenylyl)-3,5-dimethyl-1-(2-methoxycarbonyl-ethyl)-3H-imidazol-2-one hydrochloride

(90) 4-(4'-amidino-4-biphenylyl)-1-(2-methoxycarbonyl-ethyl)-5-methyl-3-phenyl-3H-imidazol-2-one hydrochloride

(91) 4-(4'-amidino-4-biphenylyl)-1-(2-methoxycarbonyl-ethyl)-5-methyl-3H-imidazol-2-one hydrochloride

(92) 1-(4-amidino-phenyl)-4-[4-(2-methoxycarbonyl-ethyl)-phenyl]-3H-imidazol-2-one hydrochloride

(93) 1-(4-amidino-phenyl)-4-[4-(2-methoxycarbonyl-ethyl)-phenyl]-3-methyl-3H-imidazol-2-one hydrochloride

(94) 1-(4-amidino-phenyl)-4-[4-(2-methoxycarbonyl-ethyl)-phenyl]-3-phenyl-3H-imidazol-2-one hydrochloride

(95) 1-(4-amidino-phenyl)-4-[4-(2-methoxycarbonyl-ethyl)-phenyl]-3H-imidazol-2-thione hydrochloride

(96) 1-(4-amidino-phenyl)-4-[4-(2-methoxycarbonyl-ethyl)-phenyl]-3-methyl-3H-imidazol-2-thione hydrochloride

(97) 1-(4-amidino-phenyl)-4-[4-(2-methoxycarbonyl-ethyl)-phenyl]-3-phenyl-3H-imidazol-2-thione hydrochloride

(98) 1-(4-amidino-phenyl)-4-[4-(2-methoxycarbonyl-ethyl)-phenyl]-5-methyl-3-phenyl-3H-imidazol-2-one hydrochloride

(99) 1-(4-amidino-phenyl)-3,5-dimethyl-4-[4-(2-methoxycarbonyl-ethyl)-phenyl]-3H-imidazol-2-one hydrochloride (100) 1-(4-amidino-phenyl)-4-[4-(2-methoxycarbonyl-ethyl)-phenyl]-5-methyl-3H-imidazol-2-one hydrochloride (101) 4-(4'-amidino-4-biphenylyl)-1-(2-methoxycarbonyl-ethyl)-3H-imidazol-2-thione hydrochloride (102) 4-(4'-amidino-4-biphenylyl)-1-(2-methoxycarbonyl-ethyl)-3-methyl-3H-imidazol-2-thione hydrochloride (103) 4-(4'-amidino-4-biphenylyl)-1-(2-methoxycarbonyl-ethyl)-3-phenyl-3H-imidazol-2-thione hydrochloride (104) 4-(4'-amidino-4-biphenylyl)-1-(2-methoxycarbonyl-ethyl)-3H-imidazol-2-one hydrochloride Melting point: 278°–282° C. (decomp.)

$R_f$ value: 0.30 (silica gel; methylene chloride/methanol=4:1)

(105) 4-(4'-amidino-4-biphenylyl)-1-(2-methoxycarbonyl-ethyl)-3-methyl-3H-imidazol-2-one hydrochloride Melting point: 258°–260° C. (decomp.)

$R_f$ value: 0.56 (silica gel; methylene chloride/ethanol=4:1)

(106) 4-(4'-amidino-4-biphenylyl)-1-(2-methoxycarbonyl-ethyl)-3-phenyl-3H-imidazol-2-one hydrochloride Melting point: 250°–253° C.

$R_f$ value: 0.55 (silica. gel; methylene chloride/ethanol=4:1)

(107) 1-(4-amidino-phenyl)-3-[4-(3-methoxycarbonyl-propyl)-phenyl]-imidazolidin-2-one hydrochloride (108) 1-(4-amidino-phenyl)-3-[1-(2-methoxycarbonyl-ethyl)-4-piperidinyl]-imidazolidin-2-one hydrochloride (109) 2-(4-amidino-4'-biphenylyl)-4-(2-methoxycarbonyl-ethyl)-4H-1,2,4-triazol-3-one hydrochloride (110) 2-(4-amidino-4'-biphenylyl)-4-(2-methoxycarbonyl-ethyl)-5-methyl-4H-1,2,4-triazol-3-one hydrochloride (111) 4-(4-amidino-4'-biphenylyl)-2-(2-methoxycarbonyl-ethyl)-4H-1,2,4-triazol-3-one hydrochloride (112) 4-(4-amidino-4'-biphenylyl)-2-(2-methoxycarbonyl-ethyl)-5-methyl-4H-1,2,4-triazol-3-one hydrochloride (113) 1-[4-(2-methoxycarbonyl-ethyl)-phenyl]-3-(4-methyl-amidino-phenyl)-imidazolidin-2-one The iminoester was taken up in absolute methanol and reacted with a 20-fold excess of a methanolic methylamine solution (114) 1-(4-n-butylamidino-phenyl)-3-[4-(2-methoxycarbonyl-ethyl)-phenyl]-imidazolidin-2-one Prepared analogously to (113) with n-butylamine (115) 1-(4-amidino-phenyl)-3-[4-(2-methoxycarbonyl-ethyl)-phenyl]-4-methyl-3H-imidazol-2-one hydrochloride Melting point: 248° C. (decomp.)

$R_f$ value: 0.40 (Reversed Phase Plate RP8; methanol/5% sodium chloride solution=6:4)

(116) 3-(4-amidino-phenyl)-1-(4-methoxycarbonyl-butyl)-3H-imidazo[4,5-b]pyridin-2-one dihydrochloride $R_f$ value: 0.34 (silica gel; methylene chloride/methanol (117) 4-(4-amidino-phenyl)-2-[4-(2-methoxycarbonyl-ethyl)-phenyl]-5-methyl-4H-1,2,4-triazol-3-one hydrochloride Melting point: 273°–275° C.

R_f value: 0.55 (silica gel; methylene chloride/methanol=4:1)

(118) 2-(4-amidino-phenyl)-4-[4-(2-methoxycarbonyl-ethyl)-phenyl]-5-methyl-4H-1,2,4-triazol-3-one hydrochloride Melting point: 272°–274° C.

R_f value: 0.37 (Reversed Phase Plate RP8; methanol/5% sodium chloride solution=6:4)

(119) 2-(4-amidino-phenyl)-5-ethyl-4-[4-(2-methoxycarbonyl-ethyl)-phenyl]-4H-1,2,4-triazol-3-one hydrochloride Melting Point: above 250° C.

R_f value: 0.36 (Reversed Phase Plate RP8; methanol/10% sodium chloride solution=6:4)

Calc.×HCl: C 58.67 H 5.63 N 16.29 Cl 8.25
Found: 58.01 5.65 16.26 9.14

(120) 3-(4'-amidino-4-biphenylyl)-1-(2-methoxycarbonyl-ethyl)-3H-imidazo[4,5-b]pyridin-2-one-hydrochloride R_f value: 0.61 (silica gel; methylene chloride/methanol=8:2)

(121) 1-(4-amidino-phenyl)-3-[4-(2-ethoxycarbonyl-ethyl)-phenyl]-3H-imidazol-2-one hydrochloride Prepared from 1-(4-cyano-phenyl)-3-[4-(2-methoxycarbonyl-ethyl)-phenyl]-3H-imidazol-2-one, whilst the iminoester formed as an intermediate product was obtained by reacting with ethanolic hydrochloric acid.

R_f value: 0.54 (Reversed Phase Plate RP8; methanol/5% sodium chloride solution=6:4)

(122) 3-(4-amidino-phenyl)-1-[4-(2-methoxycarbonyl-ethyl)-phenyl]-4-methyl-3H-imidazol-2-one hydrochloride-hydrate Melting point: 95°–100° C.

R_f value: 0.57 (silica gel; methylene chloride/methanol=4:1)

(123) 2-(4-amidino-phenyl)-4-[4-(2-methoxycarbonyl-ethyl)-phenyl]-4H-1,2,4-triazol-3-one hydrochloride Melting point: 275°–277° C.

R_f value: 0.55 (Reversed Phase Plate RP8; methanol/5% sodium chloride solution=6:4)

(124) 4-(amidino-phenyl)-2-[4-(2-methoxycarbonyl-ethyl)-phenyl]-4H-1,2,4-triazol-3-one hydrochloride Melting point: 289°–291° C. (decomp.)

R_f value: 0.49 (Reversed Phase Plate RP8; methanol/5% sodium chloride solution=6:4)

(125) 1-[1-(4-amidino-phenyl)-4-piperidinyl]-3-(2-methoxycarbonyl-ethyl)-3H-imidazol-2-one hydrochloride Melting point: above 275° C.

R_f value: 0.53 (Reversed Phase Plate RP8; methanol/10% sodium chloride solution=6:4)

(126) 1-(4-amidino-phenyl)-3-[4-(2-methoxycarbonyl-ethenyl)-phenyl]-3H-imidazol-2-one hydrochloride Melting point: 253°–264° C.

R_f value: 0.28 (Reversed Phase Plate RP8; methanol/10% sodium chloride solution=6:4)

(127) 1-(4-amidino-phenyl)-3-[4-(2-dibenzylamino-2-methoxycarbonyl-ethyl)-phenyl]-3H-imidazol-2-one hydrochloride R_f value: 0.37 (silica gel; methylene chloride/methanol/conc. ammonia=4:1:0.25)

(128) 1-(4-amidino-phenyl)-3-[4-(2-amino-2-methoxycarbonyl-ethyl)-phenyl]-3H-imidazol-2-one dihydrochloride R_f value: 0.18 (silica gel; methylene chloride/methanol/conc. ammonia=16:4:1)

(129) 1-(4-amidino-phenyl)-3-[4-(2-dimethylamino-2-methoxycarbonyl-ethyl)-phenyl]-3H-imidazol-2-one (130) 1-(4-amidino-phenyl)-3-[4-(2-methoxycarbonyl-1-methoxycarbonylmethyl-ethyl)-phenyl]-imidazolidin-2-one (131) 1-(4-amidino-phenyl)-3-(3,4-bis-methoxycarbonylmethyloxy-phenyl)-imidazolidin-2-one (132) 1-(4-amidino-phenyl)-3-[4-(2-methoxycarbonyl-ethyl-phenyl]-4-methyl-imidazolidin-2-one (133) 1-(4-amidino-phenyl)-3-[4-(2-methoxycarbonyl-2-methyl-propyl)-phenyl]-imidazolidin-2-one (134) 1-(4-amidino-phenyl)-3-[4-(2-phosphono-ethyl)-phenyl]-imidazolidin-2-one (135) 1-(4-amidino-phenyl)-3-[4-[2-(O-methyl-phosphono)-ethyl]-phenyl]-imidazolidin-2-one (136) 1-(4-amidino-phenyl)-3-[4-[2-(5-tetrazolyl)-ethyl]-phenyl]-imidazolidin-2-one (137) 1-(4-amidino-phenyl)-3-[4-(2-hydroxy-2-methoxycarbonyl-ethyl)-phenyl]-3H-imidazol-2-one (138) 1-(4-amidino-phenyl)-3-[4-(2-methoxy-2-methoxycarbonyl-ethyl)-phenyl]-3H-imidazol-2-one (139) 2-(4-amidino-phenyl)-4-[4-(2-methoxycarbonyl-2-methyl-propyl)-phenyl]-5-methyl-4H-1,2,4-triazol-3-one (140) 2-(4-amidino-phenyl)-4-[4-(2-phosphono-ethyl)-phenyl]-5-methyl-4H-1,2,4-triazol-3-one (141) 2-(4-amidino-phenyl)-4-[4-[2-(O-methyl-phosphono)-ethyl]-phenyl]-5-methyl-4H-1,2,4-triazol-3-one (142) 2-(4-amidino-phenyl)-4-[4-(2-methyloxycarbonyl-ethyl)-phenyl]-5-trifluoromethyl-4H-1,2,4-triazol-3-one (143) 2-(4-amidino-phenyl)-4-[4-(2-methyloxycarbonyl-ethyl)-phenyl]-5-phenyl-4H-1,2,4-triazol-3-one (144) 2-(4-amidino-phenyl)-4-[4-[2-(5-tetrazolyl)-ethyl]-phenyl]-5-methyl-4H-1,2,4-triazol-3-one

Example 3

1-(4'-Amidino-3-methylsulphinyl-4-biphenylyl)-3-(2-methoxycarbonyl-ethyl)-imidazolidin-2-one Prepared from 1-(4'-amidino-3-methylthio-4-biphenylyl)-3-(2-methoxycarbonyl-ethyl)-imidazolidin-2-one by oxidation with bromine in glacial acetic acid in the presence of sodium acetate at ambient temperature.

The following compounds were obtained analogously:

(1) 1-(4-amidino-2-methylsulphinyl-phenyl)-3-[4-(2-methoxycarbonyl-ethyl)-phenyl]-imidazolidin-2-one (2) 1-(4-amidino-phenyl)-3-[4-(2-methoxycarbonyl-ethyl)-2-methylsulphinyl-phenyl]-imidazolidin-2-one (3) 1-(4-amidino-phenyl)-3-(2-methoxycarbonylmethyl-sulphinyl-ethyl)-imidazolidin-2-one

Example 4

1-(4-Cyano-phenyl)-3-[2-(4-methoxycarbonyl-phenyl)-ethyl]-imidazolidin-2-one 8.1 g of 1-(4-cyano-phenyl)-3-[2-(4-methoxycarbonyl-phenyl)-ethyl]-3H-imidazol-2-one were dissolved in 750 ml of ethyl acetate and treated with hydrogen under 5 bar in the presence of 2 g of 10% palladium/charcoal for 2.5 hours at 50° C. The catalyst was filtered off, the filtrate was evaporated down to about 100 ml, 100 ml of tert.butylmethylether were added, the resulting mixture was cooled in an ice/acetone bath and the precipitate formed was filtered off then washed with tert.-butylmethylether.

Yield: 6.4 g (79% of theory),
Melting point: 194°–197° C.
$R_f$ value: 0.63 (silica gel; methylene chloride/ethyl acetate/cyclohexane=3:1:1)

The following compounds were obtained analogously:

(1) 4-(4-amidino-phenyl)-1-[4-(2-methoxycarbonyl-ethyl)-phenyl]-imidazolidin-2-one (2) 4-(4-amidino-phenyl)-1-[4-(2-methoxycarbonyl-ethyl)-phenyl]-3-methyl-imidazolidin-2-one (3) 4-(4-amidino-phenyl)-1-[4-(2-methoxycarbonyl-ethyl)-phenyl]-3-phenyl-imidazolidin-2-one (4) 1-(4-amidino-phenyl)-4-[4-(2-methoxycarbonyl-ethyl)-phenyl]imidazolidin-2-one (5) 1-(4-amidino-phenyl)-4-[4-(2-methoxycarbonyl-ethyl)-phenyl]-3-methyl-imidazolidin-2-one (6) 1-(4-amidino-phenyl)-4-[4-(2-methoxycarbonyl-ethyl)-phenyl]-3-phenyl-imidazolidin-2-one (7) 4-(4,-amidino-4-biphenylyl)-1-(2-methoxycarbonyl-ethyl)-imidazolidin-2-one (8) 4-(4,-amidino-4-biphenylyl)-1-(2-methoxycarbonyl-ethyl)-3-methyl-imidazolidin-2-one (9) 4-(4'-amidino-4-biphenylyl)-1-(2-methoxycarbonyl-ethyl)-3-phenyl-imidazolidin-2-one hydrochloride The hydrochloride of the free acid was used as starting material and was reduced in methanol at ambient temperature.
Melting point: 225°–235° C. (decomp.)

(10) 1-[4-(4-amidino-phenyl)-cyclohexyl]-3-(2-methoxycarbonyl-ethyl)-imidazolidin-2-one

(11) 1-[1-(4-amidino-phenyl)-4-piperidinyl]-3-(2-methoxycarbonyl-ethyl)-imidazolidin-2-one hydrochloride Dilute methanolic hydrochloric acid was used and the work was done at ambient temperature.
$R_f$ value: 0.47 (Reversed Phase Plate; methanol/10% sodium chloride solution=6:4)

(12) 1-(4-cyano-phenyl)-3-[4-(2-methoxycarbonyl-ethyl)-phenyl]-imidazolidin-2-one hydrochloride Melting point: 160°–162° C.
$R_f$ value: 0.59 (silica gel; cyclohexane/ethyl acetate=3:7)

(13) 4-(4'-amidino-4-biphenylyl)-1-(2-carboxy-ethyl)-3-phenyl-imidazolidin-2-one hydrochloride The work was done in ethanol at ambient temperature.
Melting point: 236°–240° C.

(14) 4-(4'-amidino-4-biphenylyl)-1-(2-carboxy-ethyl)-3-methyl-imidazolidin-2-one hydrochloride The work was done in ethanol at ambient temperature.
$R_f$ value: 0.55 (Reversed Phase Plate RP18; methanol/5% sodium chloride solution=6:4)

(15) 4-(4'-amidino-4-biphenylyl)-1-(2-carboxy-ethyl)-imidazolidin-2-one hydrochloride The work was done in ethanol at ambient temperature.
$R_f$ value: 0.61 (Reversed Phase Plate RP18; methanol/5% sodium chloride solution=6:4)

(16) 4-(4-amidino-phenyl)-1-[4-(2-carboxy-ethyl)-phenyl]-3-methyl-imidazolidin-2-one hydrochloride The work was done in dioxane/water (=1:1).
Melting point: 208°–210° C.

(17) 1-(4-amidino-phenyl)-3-[4-(2-amino-2-methoxycarbonyl-ethyl)-phenyl]-imidazolidin-2-one dihydrochloride The work was done in methanol at ambient temperature.
$R_f$ value: 0.37 (silica gel; methylene chloride/methanol/conc. ammonia=8:4:1)

(18) 1-(4-amidino-phenyl)-3-[4-(2-amino-2-carboxy-ethyl)-phenyl]-imidazolidin-2-one Melting point: 295° C. (decomp.)
$R_f$ value: 0.07 (silica gel; methylene chloride/methanol/conc. ammonia=8:4:1)

Example 5

1-(4-Ethoxycarbonylamidino-phenyl)-3-[4-(2-ethoxycarbonyl-ethyl)-phenyl]-3H-imidazol-2-one At ambient temperature, 10 ml of 0.2N sodium hydroxide solution were added dropwise, with vigorous stirring, to a mixture of 0.3 g of 1-(4-amidino-phenyl)-3-[4-(2-ethoxycarbonyl-ethyl)-phenyl]-3H-imidazol-2-one hydrochloride, 0.07 ml of ethyl chloroformate and 40 ml of methylene chloride. After stirring for 0.5 hours at ambient temperature the methylene chloride phase was separated off and evaporated to dryness.
Yield: 0.29 g (90% of theory),
$R_f$ value: 0.48 (silica gel; methylene chloride/methanol= 15:1)
Calc.: C 63.99 H 5.82 N 12.44
Found: 64.11 5.98 12.35

The following compounds were obtained analogously:

(1) 1-(4-methoxycarbonylamidino-phenyl)-3-[4-(2-methoxycarbonyl-ethyl)-phenyl]-imidazolidin-2-one Melting point: above 260° C.
$R_f$ value: 0.73 (silica gel; methylene chloride/methanol=95:5)

(2) 1-(4-benzyloxycarbonylamidino-phenyl)-3-[4-(2-methoxycarbonyl-ethyl)-phenyl]-imidazolidin-2-one (3) 1-(4-isopropylcarbonylamidino-phenyl)-3-[4-(2-methoxycarbonyl-ethyl)-phenyl]-imidazolidin-2-one (4) 1-(4-isobutyloxycarbonylamidino-phenyl)-3-[4-(2-methoxycarbonyl-ethyl)-phenyl]-imidazolidin-2-one (5) 1-(4-ethoxycarbonylamidino-phenyl)-3-[4-(2-methoxycarbonyl-ethyl)-phenyl]-imidazolidin-2-one (6) 4-(4-methoxycarbonylamidino-phenyl)-2-[4-(2-methoxycarbonyl-ethyl)-phenyl]-4H-1,2,4-triazol-3-one Melting point: 296°–298° C.
$R_f$ value: 0.46 (silica gel; methylene chloride/methanol=15:1)

(7) 4-[4-(2-isopropyloxycarbonyl-ethyl)-phenyl]-2-(4-methoxycarbonylamidino-phenyl)-5-methyl-4H-1,2,4-triazol-3-one Melting point: 175°–188° C. (decomp.)
$R_f$ value: 0.28 (silica gel; methylene chloride/methanol=95:5)

(8) 1-(4-methoxycarbonylamidino-phenyl)-3-[4-(2-methoxycarbonyl-ethyl)-phenyl]-3H-imidazol-2-one Melting point: above 260° C.
$R_f$ value: 0.27 (silica gel; methylene chloride/methanol=95:5)
Calc.: C 62.55 H 5.25 N 13.26
Found: 62.24 5.33 13.45

(9) 1-(4-ethoxycarbonylamidino-phenyl)-3-[4-(2-ethoxycarbonyl-ethyl)-phenyl]-imidazolidin-2-one Melting point: above 335° C.
$R_f$ value: 0.49 (silica gel; methylene chloride/methanol=15:1)

(10) 2-(4-methoxycarbonylamidino-phenyl)-3-[4-(2-methoxycarbonyl-ethyl)-phenyl]-5-methyl-4H-1,2,4-triazol-3-one Melting point: 211°–213° C. (decomp.)
$R_f$ value: 0.54 (silica gel; methylene chloride/methanol=15:1)

(11) 2-(4-methoxycarbonylamidino-phenyl)-3-[4-(2-methoxycarbonyl-ethyl)-phenyl]-4H-1,2,4-triazol-3-one Melting point: above 340° C.
$R_f$ value: 0.45 (silica gel; methylene chloride/methanol=15:1)

(12) 1-(4-methoxycarbonylamidino-phenyl)-3-[4-(2-methoxycarbonyl-ethyl)-cyclohexyl]-imidazolidin-2-one $R_f$ value: 0.29 (Reversed Phase Plate RP8; methanol/5% sodium chloride solution=6:4)

(13) 1-(4-methoxycarbonylamidino-phenyl)-3-[4-(2-methoxycarbonyl-ethyl)-phenyl]-imidazolidin-2,4-dione Melting point: 250° C. (decomp., sintering from 198° C.)
$R_f$ value: 0.45 (silica gel; ethyl acetate)
Calc.: C 60.27 H 5.06 N 12.78
Found: 60.18 5.12 12.82

(14) 1-(4-methoxycarbonylamidino-phenyl)-3-[4-(2-methoxycarbonyl-ethyl)-phenyl]-4-methyl-3H-imidazol-2-one Melting point: 212°–213° C.
$R_f$ value: 0.58 (silica gel; methylene chloride/methanol=9:1)

(15) 1-(4-ethoxycarbonylamidino-phenyl)-3-[4-(2-methoxycarbonyl-ethyl)-phenyl]-4-methyl-3H-imidazol-2-one Melting point: 198°–199° C.
$R_f$ value: 0.58 (silica gel; methylene chloride/methanol=9:1)

(16) 2-(4-methoxycarbonylamidino-phenyl)-5-[4-(2-methoxycarbonyl-ethyl)-phenyl]-3,4-dihydro-2H,5H-1,2,5-thiadiazole-1,1-dioxide Melting point: above 275° C.
$R_f$ value: 0.23 (silica gel; methylene chloride/methanol=100:3)

(17) 2-(4-ethoxycarbonylamidino-phenyl)-5-[4-(2-methoxycarbonyl-ethyl)-phenyl]-3,4-dihydro-2H,5H-1,2,5-thiadiazole-1,1-dioxide Melting point: above 275° C.
$R_f$ value: 0.22 (silica gel; methylene chloride/methanol=100:3)

(18) 4-[4-(2-isobutyloxycarbonyl-ethyl)-phenyl]-2-(4-methoxycarbonylamidino-phenyl)-5-methyl-4H-1,2,4-triazol-3-one Melting point: 200°–201° C.
$R_f$ value: 0.43 (silica gel; methylene chloride/methanol=95:5)
Calc.: C 62.62 H 6.09 N 14.60
Found: 62.77 6.20 14.88

Example 6

1-(4-Amidino-phenyl)-3-[4-(2-butyloxycarbonyl-ethyl)-phenyl]-imidazolidin-2-one hydrochloride Prepared from 1-(4-amidino-phenyl)-3-[4-(2-methoxycarbonyl-ethyl)-phenyl]-imidazolidin-2-one hydrochloride by stirring with saturated butanolic hydrochloric acid for three days at ambient temperature.

The following compound was obtained analogously:

(1) 1-(4-amidino-phenyl)-3-[4-[2-(2-phenyl-ethyloxycarbonyl)-ethyl]-phenyl]-imidazolidin-2-one hydrochloride Example 7

1-(1-Amidino-4-piperidinyl)-3-[4-(2-methoxycarbonyl-ethyl)-phenyl]-imidazolidin-2-one Prepared from 1-[4-(2-methoxycarbonyl-ethyl)-phenyl]-3-(4-piperidinyl)-imidazolidin-2-one and S-ethylisothiourea-hydrobromide by heating to 100° C. for four hours in dimethylformamide in the presence of sodium carbonate.

Example 8

1-(4-Aminomethyl-phenyl)-3-(4-methoxycarbonylmethyloxy-phenyl)-imidazolidin-2-one hydrochloride 2 g of 1-(4-cyano-phenyl)-3-(4-methoxycarbonylmethyloxy-phenyl)-imidazolidin-2-one were treated with 5 bars of hydrogen for 2.5 hours at ambient temperature in a mixture of 40 ml of methanol and 4 ml of methanolic hydrochloric acid in the presence of 0.5 g of 10% palladium/charcoal. 200 ml of methanol and 50 ml of water were added and the mixture was filtered while hot. The product crystallised out upon cooling.
Yield: 1.38 g (62% of theory).
Melting point: above 250° C.
$R_f$ value: 0.40 (Reversed Phase Plate RP8; methanol/5% sodium chloride solution=6:4)
Calc.×HCl: C 58.24 H 5.66 N 10.72 Cl 9.05
Found: 58.04 5.65 10.92 9.57

The following compounds were obtained analogously:

(1) 1-(4-aminomethyl-phenyl)-3-[4-(2-methoxycarbonyl-ethyl)-phenyl]-3,4,5,6-tetrahydro-1H-pyrimidin-2-one hydrochloride Melting point: 272°–274° C. (decomp.)
$R_f$ value: 0.30 (silica gel; toluene/dioxane/methanol/conc. ammonia=2:5:2:1)

(2) 1-(4-aminomethyl-phenyl)-3-[4-(2-methoxycarbonyl-ethyl)-phenyl]-imidazolidin-2-one hydrochloride Melting point: above 250° C.
$R_f$ value: 0.47 (silica gel; toluene/dioxane/methanol/conc. ammonia=4:10:4:1)
Calc.×HCl: C 61.61 H 6.20 N 10.78 Cl 9.09
Found: 61.30 6.29 10.88 9.12

(3) 1-[4-(2-amino-2-methoxycarbonyl-ethyl)-phenyl]-3-(4-aminomethyl-phenyl)-imidazolidin-2-one dihydrochloride $R_f$ value: 0.66 (silica gel; methylene chloride/methanol/conc. ammonia=16:4:1)

(4) 1-[4-(2-amino-ethyl)-phenyl]-3-(4-methoxycarbonylmethyl-phenyl)-imidazolidin-2-one The work was done at 40° C.
Melting point: above 250° C.
$R_f$ value: 0.31 (silica gel; toluene/dioxane/methanol/conc. ammonia=4:10:4:1)

(5) 1-(4-aminomethyl-2-methyl-phenyl)-3-[4-(2-methoxycarbonyl-ethyl)-phenyl]-imidazolidin-2-one Melting point: above 275° C.
$R_f$ value: 0.38 (Reversed Phase Plate RP8; methanol/5% sodium chloride solution=6:4)

(6) 3-(4-aminomethyl-phenyl)-1-[4-(2-methoxycarbonyl-ethyl)-phenyl]-4-methyl-3H-imidazol-2-one (7) 1-(4'-aminomethyl-4-biphenylyl)-3-(2-methoxycarbonyl-ethyl)-imidazolidin-2-one (8) 1-(4-aminomethyl-3-fluoro-phenyl)-3-[4-(2-methoxycarbonyl-ethyl)-phenyl]-imidazolidin-2-one (9) 1-(4-aminomethyl-phenyl)-3-[3-(2-methoxycarbonyl-ethyl)-phenyl]-imidazolidin-2-one

(10) 1-(4-aminomethyl-phenyl)-3-[4-(2-methoxycarbonyl-1-methoxycarbonylmethyl-ethyl)-phenyl]-imidazolidin-2-one

(11) 4-(4-aminomethyl-phenyl)-2-[4-(2-methoxycarbonyl-ethyl)-phenyl]-4H-1,2,4-triazol-3-one

(12) 1-[4-(2-amino-ethyl)-phenyl]-3-[4-(2-methoxycarbonyl-ethyl)-phenyl]-imidazolidin-2-one Melting point: above 200° C.

$R_f$ value: 0.63 (Reversed Phase Plate RP8; glacial acetic acid/water=1:1)

(13) 1-[4-(1-amino-2-methyl-2-propyl)-phenyl]-3-[4-(2-methoxycarbonyl-ethyl)-phenyl]-imidazolidin-2-one

(14) 2-(4-aminomethyl-phenyl)-4-[4-(2-methoxycarbonyl-ethyl)-phenyl]-5-methyl-4H-1,2,4-triazol-3-one

(15) 1-[4-(2-amino-ethyl)-phenyl]-3-(4-methoxycarbonyl-methyloxy-phenyl)-imidazolidin-2-one

(16) 1-[3-(2-amino-ethyl)-phenyl]-3-[4-(2-methoxycarbonyl-ethyl)-phenyl]-imidazolidin-2-one-hydrochloride The starting 1-(3-cyanomethyl-phenyl)-3-[4-(2-methoxycarbonyl-ethyl)-phenyl]-3H-imidazol-2-one was reduced in a mixture of 50 ml of dioxane, 10 ml of methanol and 1 ml of methanolic hydrochloric acid.

Melting point: above 260° C.

$R_f$ value: 0.29 (Reversed Phase Plate RPS; methanol/5% sodium chloride solution=6:4)

(17) 1-(4-aminomethyl-cyclohexyl)-3-[4-(2-methyoxycarbonyl-ethyl)-phenyl]-imidazolidin-2-one

Example 9

1-[2-(4-Amidino-phenyl)-2-hydroxy-ethyl]-3-(3-methoxycarbonyl-propyl)-imidazolidin-2-one Prepared by reduction of 1-[(4-amidino-phenyl)-carbonylmethyl]-3-(3-methoxycarbonyl-propyl)-imidazolidin-2-one hydrochloride with sodium borohydride in methanol at 0°–5° C.

Example 10

1-(3-Guanidino-phenyl)-3-[4-(2-methoxycarbonyl-ethyl)-phenyl]-imidazolidin-2-one hydrochloride Prepared from 1-(3-amino-phenyl)-3-[4-(2-methoxycarbonyl-ethyl)-phenyl]-imidazolidin-2-one hydrochloride by refluxing for three hours with cyanamide in dioxane.

Example 11

1-(4'-Cyano-4-biphenylyl)-3-(2-methoxycarbonyl-ethyl)-imidazolidin-2-one 2 g of 1-(2-carboxy-ethyl)-3-(4'-cyano-4-biphenylyl)-imidazolidin-2-one were suspended in 150 ml of methanol, 6 ml of concentrated methanolic hydrochloric acid were added and the mixture was stirred for 16 hours at ambient temperature. The precipitate was filtered off and purified by column chromatography on silica gel (eluant: methylene chloride/ethyl acetate=9:1).

Yield: 0.5 g (23% of theory),

Melting point: 150°–155° C.

$R_f$ value: 0.50 (silica gel; methylene chloride/ethyl acetate=9:1)

The following compounds were obtained analogously:

(1) 1-(4'-cyano-3'-fluoro-4-biphenylyl)-3-(2-methoxycarbonyl-ethyl)-imidazolidin-2-one (2) 1-(3'-chloro-4'-cyano-4-biphenylyl)-3-(2-methoxycarbonyl-ethyl)-imidazolidin-2-one (3) 1-(4'-cyano-3-methoxy-4-biphenylyl)-3-(2-methoxycarbonyl-ethyl)-imidazolidin-2-one (4) 1-(4'-cyano-3-methylthio-4-biphenylyl)-3-(2-methoxycarbonyl-ethyl)-imidazolidin-2-one (5) 1-(4'-cyano-2,3-dimethyl-4-biphenylyl)-3-(2-methoxycarbonyl-ethyl)-imidazolidin-2-one (6) 1-[4-(5-cyano-2-pyridyl)-phenyl]-3-(2-methoxycarbonyl-ethyl)-imidazolidin-2-one (7) 1-[4-(5-cyano-2-pyrazinyl)-phenyl]-3-(2-methoxycarbonyl-ethyl)-imidazolidin-2-one (8) 1-[4-(5-cyano-2-pyrimidinyl)-phenyl]-3-(2-methoxycarbonyl-ethyl)-imidazolidin- 2-one (9) 1-[6-(4-cyano-phenyl)-3-pyridazinyl]-3-(2-methoxycarbonyl-ethyl)-imidazolidin-2-one

(10) 1-[2-(4-cyano-phenyl)-5-pyrimidinyl]-3-(2-methoxycarbonyl-ethyl)-imidazolidin-2-one

(11) 2-(4-amidino-phenyl)-4-[4-(2-isopropyloxycarbonyl-ethyl)-phenyl]-5-methyl-4H-1,2,4-triazol-3-one hydrochloride Isopropanolic hydrochloric acid was used.

Melting point: 255°–257° C.

$R_f$ value: 0.33 (Reversed Phase Plate RPS; methanol/5% sodium chloride solution=6:4)

(12) 2-(4-amidino-phenyl)-4-[4-(2-isobutyloxycarbonyl-ethyl)-phenyl]-5-methyl-4H-1,2,4-triazol-3-one hydrochloride Melting point: above 250° C.

$R_f$ value: 0.22 (Reversed Phase Plate RP8; methanol/5% sodium chloride solution=6:4)

Calc.×HCl: C 60.32 H 6.16 N 15.29 Cl 7.74
Found: 60.19 H 6.28 N 15.37 Cl 7.78

(13) 2-(4-amidino-phenyl)-5-ethyl-4-[4-(2-isopropyloxycarbonyl-ethyl)-phenyl]-4H-1,2,4-triazol-3-one Melting point: above 250° C.

$R_f$ value: 0.27 (Reversed Phase Plate, RP8; methanol/5% sodium chloride solution=6:4)

(14) 1-(4-amidino-phenyl)-3-[4-(2-isopropyloxycarbonyl-ethyl)-phenyl]-4-methyl-3H-imidazol-2-one Melting point: 246°–249° C.

$R_f$ value: 0.34 (Reversed Phase Plate, RP8; methanol/5% sodium chloride solution=6:4)

(15) 4-(4-amidino-phenyl)-2-[4-(2-isopropyloxycarbonyl-ethyl)-phenyl]-4H-1,2,4-triazol-3-one

(16) 1-(4-amidino-phenyl)-3-[4[(2-isopropyloxycarbonyl-ethyl)-phenyl]-imidazolidin-2-one

(17) 1-(4-amidino-phenyl)-3-[4-(2-isopropyloxycarbonyl-ethyl)-phenyl]-3H-imidazol-2-one Melting point: above 250° C.

$R_f$ value: 0.28 (Reversed Phase Plate, RPS; methanol/5% sodium chloride solution=6:4)

(18) 1-(4-amidino-phenyl)-3-[4[(2-isopropyloxycarbonyl-ethyl)-phenyl]-imidazolidin-2,4-dione Melting point: above 250° C.

$R_f$ value: 0.37 (Reversed Phase Plate, RPS; methanol/5% sodium chloride solution=6:4)

Example 12

1-(2-Carboxy-ethyl)-3-(4'-cyano-4-biphenylyl)-imidazolidin-2-one 3.4 g of 1-(3-buten-1-yl)-3-(4'-cyano-4-biphenylyl)-imidazolidin-2-one were dissolved in a mixture of 20 ml of methylene chloride and 20 ml of acetonitrile and 25 mg of ruthenium trichloride trihydrate were added. A mixture of 16 g of sodium metaperiodate and 65 ml of water was added and stirred for 2.5 hours. Then 100 ml of methylene chloride and 20 ml of water were added, the phases were separated and the aqueous phase was washed several times with methylene chloride. The combined organic phases were evaporated down and the powdery residue was used as it was without any further purification.

Yield: 2 g (56% of theory).

$R_f$ value: 0.12 (silica gel; cyclohexane/ethyl acetate=1:1)

The following compounds were obtained analogously:

(1) 1-(2-carboxy-ethyl)-3-(4'-cyano-3,-fluoro-4-biphenylyl)-imidazolidin-2-one (2) 1-(2-carboxy-ethyl)-3-(3'-chloro-4,-cyano-4-biphenylyl)-imidazolidin-2-one (3) 1-(2-carboxy-ethyl)-3-(4'-cyano-3-methoxy-4-biphenylyl)-imidazolidin-2-one (4) 1-(2-carboxy-ethyl)-3-(4'-cyano-3-methylthio-4-biphenylyl)-imidazolidin-2-one (5) 1-(2-carboxy-ethyl)-3-(4'-cyano-2,3-dimethyl-4-biphenylyl)-imidazolidin- 2-one (6) 1-(2-carboxy-ethyl)-3-[4-(5-cyano-2-pyridyl)-phenyl]-imidazolidin-2-one (7) 1-(2-carboxy-ethyl)-3-[4-(5-cyano-2-pyrazinyl)-phenyl]-imidazolidin-2-one (8) 1-(2-carboxy-ethyl)-3-[4-(5-cyano-2-pyrimidinyl)-phenyl]-imidazolidin-2-one (9) 1-(2-carboxy-ethyl)-3-[6-(4-cyano-phenyl)-3-pyridazinyl]-imidazolidin-2-one

(10) 1-(2-carboxy-ethyl)-3-[2-(4-cyano-phenyl)-5-pyrimidinyl]-imidazolidin-2-one

Example 13

1-(4'-Cyano-4-biphenylyl)-3-methoxycarbonylmethyl-imidazolidin-2-one 4 g of 1-(4'-cyano-4-biphenylyl)-imidazolidin-2-one were dissolved at 50° C. in 150 ml of dimethylformamide and 0.73 g of a 95% suspension of sodium hydride in oil was added in batches thereto. The mixture was allowed to cool to ambient temperature, then a solution of 1.7 ml of methyl bromoacetate in 15 ml of dimethylformamide was added dropwise thereto and the mixture was stirred for 64 hours at ambient temperature. The reaction mixture was poured onto 300 ml of water. The precipitate formed was purified by column chromatography (silica gel; methylene chloride/ethyl acetate=9:1).

Yield: 3.2 g (63% of theory).

$R_f$ value: 0.54 (silica gel; cyclohexane/ethyl acetate=1:2)

The following compounds were obtained analogously:

(1) 1-(4'-cyano-4-biphenylyl)-3-methoxycarbonylmethyl-3,4,5,6-tetrahydro-1H-pyrimidin-2-one Melting point: 145°–150° C.

$R_f$ value: 0.28 (silica gel; cyclohexane/ethyl acetate=1:2)

(2) 1-[2-(4'-cyano-4-biphenylyl)-ethyl]-3-methoxycarbonylmethyl- 3H-benzimidazol-2-one Potassium tert.butoxide was used as base. The 4-cyano-4,-(2-iodoethyl)-biphenyl used was obtained from 4-(2-bromoethyl)-4'-cyano-biphenyl by reacting with sodium iodide in acetone at ambient temperature.

$R_f$ value: 0.89 (silica gel; methylene chloride/methanol=95:5)

(3) 1-[2-(4'-cyano-4-biphenylyl)-ethyl]-3-methoxycarbonylmethyl-imidazolidin-2-one (4) 2-(4,-cyano-4-biphenylyl)-5-(2-ethoxycarbonyl-ethyl)-3,4-dihydro-2H,5H-1,2,5-thiadiazole-1,1-dioxide The work was done in dimethylformamide with potassium tert.butoxide and 1-bromo-2-chloro-ethane as alkylating agents.

Melting point: 183°–185° C.

(5) 1-(4-cyano-phenyl)-3-(4-ethoxycarbonyl-butyl)-imidazolidin-2-one $R_f$ value: 0.62 (silica gel; cyclohexane/ethyl acetate=1:3)

(6) 3-(4-cyano-phenyl)-1-(4-ethoxycarbonyl-butyl)-3H-imidazo[4,5-b]pyridin-2-one $R_f$ value: 0.78 (silica gel; methylene chloride/methanol=9:1)

Example 14

1-(4,-Cyano-4-biphenylyl)-3-(2-ethoxycarbonyl-ethyl)-3,4,5,6-tetrahydro-1H-pyrimidin-2-one 1.9 g of N-(4'-cyano-4-biphenylyl)-N-(3-methanesulphonyloxy-propyl)-N'-(2-ethoxycarbonyl-ethyl)-urea were dissolved in 2 ml of dimethylformamide, 0.18 g of a 55% suspension of sodium hydride in oil was added thereto at ambient temperature and the mixture was stirred at ambient temperature for 2 hours. 20 ml of water were added and the precipitate formed was purified by column chromatography (silica gel; ethyl acetate).

Yield: 1.0 g (64% of theory).

Melting point: 137°–138° C.

$R_f$ value: 0.57 (silica gel; cyclohexane/ethyl acetate=1:5)

The following compounds were obtained analogously:

(1) 1-(4-cyano-phenyl)-3-[4-(2-methoxycarbonyl-ethyl)-phenyl]-imidazolidin-2-one Melting point: 160°–162.5° C.

$R_f$ value: 0.59 (silica gel; cyclohexane/ethyl acetate=3:7)

(2) 1-(4-cyano-phenyl)-3-[4-(2-methoxycarbonyl-ethyl)-phenyl]-3,4,5,6-tetrahydro-1H-pyrimidin-2-one Melting point: 149°–152° C.

$R_f$ value: 0.25 (silica gel; cyclohexane/ethyl acetate=1:1)

(3) 1-(4-cyano-3-fluoro-phenyl)-3-[4-(2-methoxycarbonyl-ethyl)-phenyl]-imidazolidin-2-one (4) 1-(3-chloro-4-cyano-phenyl)-3-[4-(2-methoxycarbonyl-ethyl)-phenyl]-imidazolidin-2-one (5) 1-(4-cyano-2-methylthio-phenyl)-3-[4-(2-methoxycarbonyl-ethyl)-phenyl]-imidazolidin-2-one (6) 1-(4-cyano-2-methyl-phenyl)-3-[4-(2-methoxycarbonyl-ethyl)-phenyl]-imidazolidin-2-one (7) 1-(4-cyano-2-methoxy-phenyl)-3-[4-(2-methoxycarbonyl-ethyl)-phenyl]-imidazolidin-2-one (8) 1-(4-cyano-phenyl)-3-[2-fluoro-4-(2-methoxycarbonyl-ethyl)-phenyl]-imidazolidin-2-one (9) 1-[2-chloro-4-(2-methoxycarbonyl-ethyl)-phenyl]-3-(4-cyano-phenyl)-imidazolidin-2-one

(10) 1-(4-cyano-phenyl)-3-[2-methoxy-4-(2-methoxycarbonyl-ethyl)-phenyl]-imidazolidin-2-one

(11) 1-(4-cyano-phenyl)-3-[4-(2-methoxycarbonyl-ethyl)-2-methyl-phenyl]-imidazolidin-2-one

(12) 1-(4-cyano-phenyl)-3-[4-(2-methoxycarbonyl-ethyl)-2-methylthio-phenyl]-imidazolidin-2-one

(13) 1-(4-cyano-phenyl)-3-[5-(2-methoxycarbonyl-ethyl)-2-pyridyl]-imidazolidin-2-one

(14) 1-(4-cyano-phenyl)-3-[4-(2-methoxycarbonyl-ethyl)-cyclohexyl]-imidazolidin-2-one

(15) 1-(4-cyano-phenyl)-3-(4-methoxycarbonylmethyloxy-phenyl)-imidazolidin-2-one

(16) 1-(4-tert.butyloxycarbonylmethylthio-phenyl)-3-(4-cyano-phenyl)-imidazolidin-2-one
Melting point: 169°–171° C.

(17) 1-(4-cyano-phenyl)-3-[4-(3-methoxycarbonyl-2-methyl-2-propyl)-phenyl]-imidazolidin-2-one
Sodium iodide was added and potassium tert.butoxide was used as base.
Melting point: 177°–179° C.

(18) 1-(4-cyano-phenyl)-3-[2-(4-ethoxycarbonyl-phenyl)-ethyl]-imidazolidin-2-one

(19) 1-(4-cyano-phenyl)-3-[4-(2-methoxycarbonyl-ethenyl)-phenyl]-imidazolidin-2-one

(20) 1-(5-cyano-2-pyridyl)-3-[4-(2-methoxycarbonyl-ethyl)-phenyl]-imidazolidin-2-one

(21) 1-(4-cyano-phenyl)-3-[4-(3-methoxycarbonyl-propyl)-phenyl]-imidazolidin-2-one

(22) 1-(4-cyanomethyl-phenyl)-3-(4-methoxycarbonyl-methyl)-phenyl]-imidazolidin-2-one The iodide [$R_f$ value: 0.66 (silica gel; cyclohexane/ethyl acetate=3:7)] obtained from the corresponding mesylate was used.
Melting point: 157°–160° C.
$R_f$ value: 0.30 (silica gel; cyclohexane/ethyl acetate=4:6)

Example 15

1-(4'-Cyano-4-biphenylyl)-3-(2-ethoxycarbonyl-ethyl)-3H-imidazol-2-one

A mixture of 2.8 g of N-(4'-cyano-4-biphenylyl)-N-(2,2-diethoxy-ethyl)-N'-(2-ethoxycarbonyl-ethyl)-urea, 2.8 ml of 2N hydrochloric acid and 28 ml of ethanol was refluxed for 45 minutes. The reaction mixture was cooled to 0° C., the product precipitated was suction filtered and washed with ethanol at 0° C.
Yield: 1.4 g (63% of theory).
Melting point: 140°–142° C.
$R_f$ value: 0.40 (silica gel; cyclohexane/ethyl acetate=1:1)
The following compounds were obtained analogously:

(1) 1-[4-(4-cyano-phenyl)-cyclohexyl]-3-(2-ethoxycarbonyl-ethyl)-3H-imidazol-2-one (2) 1-(4-cyano-phenyl)-3-[4-(2-methoxycarbonyl-ethyl)-phenyl]-3H-imidazol-2-one
The work was done with methanolic hydrochloric acid.
Melting point: 153°–155° C.

(3) 1-(4-cyano-phenyl)-3-[2-(4-methoxycarbonyl-phenyl)-ethyl]-3H-imidazol-2-one
Melting point: 181°–183° C.

(4) 1-[1-(4-cyano-phenyl)-4-piperidinyl]-3-(2-ethoxycarbonyl-ethyl)-3H-imidazol-2-one
Melting point: 153°–155° C.

(5) 1-(4-cyano-phenyl)-3-[4-(2-methoxycarbonyl-ethenyl)-phenyl]-3H-imidazol-2-one
Melting point: 210°–212° C.
$R_f$ value: 0.76 (silica gel; methylene chloride/ethyl acetate= 9:1)

(6) 1-(4-cyano-phenyl)-3-[4-(2-dibenzylamino-2-methoxy-carbonyl-ethyl)-phenyl]-3H-imidazol-2-one
$R_f$ value: 0.40 (silica gel; cyclohexane/ethyl acetate=2:1)

(7) 1-[4-(2-amino-2-methoxycarbonyl-ethyl)-phenyl]-3-(4-cyano-phenyl)-3H-imidazol-2-one hydrochloride
$R_f$ value: 0.82 (silica gel; methylene chloride/methanol/conc. ammonia=16:4:1)

Example 16

1-(4'-Cyano-4-biphenylyl)-3-(2-ethoxycarbonyl-ethyl)-imidazolidin-2,4-dione 5 g of N-(tert.butyloxycarbonyl-methyl)-N-(4'-cyano-4-biphenylyl)-N'-(2-ethoxycarbonyl-ethyl)-urea were dissolved in 30 ml of methylene chloride, 30 ml of trifluoroacetic acid were added and the resulting mixture was stirred at ambient temperature for 16 hours. It was evaporated to dryness, digested with water and the precipitate was recrystallised from tert.butyl-methylether/ethyl acetate=1:1.3.
Yield: 2.9 g (55% of theory).
Melting point: 177°–178° C.
$R_f$ value: 0.57 (silica gel; methylene chloride/ethyl acetate= 7:1)
The following compound was obtained analogously:

(1) 1-(4-aminomethyl-phenyl)-3-[4-[2-(5-tetrazolyl)-ethyl]-phenyl]-imidazolidin-2-one

Example 17

1-(3-Bromo-4'-cyano-4-biphenylyl)-3-(2-methoxycarbonyl-ethyl)-imidazolidin-2-one Prepared by reacting 1-(4'-cyano-4-biphenylyl)-3-(2-methoxycarbonyl-ethyl)-imidazolidin-2-one with bromine in glacial acetic acid at ambient temperature.

Example 18

1-(4-Amidino-phenyl)-3-(methoxycarbonylmethylsulphonyl-phenyl)-imidazolidin-2-one 2.1 g of 1-(4-amidino-phenyl)-3-(methoxycarbonylmethyl-thio-phenyl)-imidazolidin-2-one were suspended in 10 ml of formic acid, 1.3 ml of 30% hydrogen peroxide were added and the mixture was stirred at ambient temperature for 16 hours. The precipitate formed was filtered off (see Example (2)), excess peroxide was destroyed by the addition of sodium bisulphite solution and the remainder was evaporated down in vacuo. The residue was extracted by boiling with a mixture of 100 ml of methylene chloride and 60 ml of methanol. The solution obtained was evaporated down and the residue was purified by column chromatography (silica gel; methylene chloride/methanol=9:1). In addition to 1 mol of water the product contains 0.5 mol of hydrochloric acid and 1 mol of formic acid.
Yield: 0.25 g (10% of theory)
$R_f$ value: 0.43 (silica gel; methylene chloride/methanol=8:2)
The following compounds were obtained analogously:

(1) 1-(4-cyano-phenyl)-3-[4-(2-methoxycarbonyl-ethyl)-2-methylsulphonyl-phenyl]-imidazolidin-2-one (2) 1-(4-cyano-phenyl)-3-(4-methoxycarbonylmethyl-sulphonyl-phenyl)-imidazolidin-2-one
(Obtained as a by-product of Example 18)
Melting point: 246°–249° C.

(3) 1-(4-cyano-2-methylsulphonyl-phenyl)-3-[4-(2-methoxycarbonyl-ethyl)-phenyl]-imidazolidin-2-one (4) 1-(4'-cyano-3-methylsulphonyl-4-biphenylyl)-3-(2-methoxycarbonyl-ethyl)-imidazolidin-2-one (5) 1-(4-amidino-phenyl)-3-(4-methoxycarbonylmethyl-sulphinyl-phenyl)-imidazolidin-2-one
The work was done in glacial acetic acid at 10° C. with equimolar amounts of hydrogen peroxide.
Melting point: from 215° C. (decomp.)
$R_f$ value: 0.48 (Reversed Phase Plate RP8, methanol/10% sodium chloride solution=6:4)

Example 19

1-(4'-Cyano-3-nitro-4-biphenylyl)-3-(2-methoxycarbonyl-ethyl)-imidazolidin-2-one Prepared by reacting 1-(4'-cyano-4-biphenylyl)-3-(2-methoxycarbonyl-ethyl)-imidazolidin-2-one with fuming nitric acid at 0° C.

Example 20

1-(3-Amino-4'-cyano-4-biphenylyl)-3-(2-methoxycarbonyl-ethyl)-imidazolidin-2-one Prepared by reduction of 1-(4'-cyano-3-nitro-4-biphenylyl)- 3-(2-methoxycarbonyl-ethyl)-imidazolidin-2-one with hydrogen at 5 bars in the presence of 5% palladium/charcoal in ethyl acetate at ambient temperature.

Example 21

1-(3-Acetamino-4'-cyano-4-biphenylyl)-3-(2-methoxycarbonyl-ethyl)-imidazolidin-2-one Prepared from 1-(3-amino-4'-cyano-4-biphenylyl)-3-(2-methoxycarbonyl-ethyl)-imidazolidin-2-one and acetylchloride in methylene chloride at ambient temperature using ethyl-diisopropylamine.

The following compounds were obtained analogously:

(1) 1-(3-benzoylamino-4'-cyano-4-biphenylyl)-3-(2-methoxycarbonyl-ethyl)-imidazolidin-2-one (2) 1-(4'-cyano-3-methanesulphonylamino-4-biphenylyl)-3-(2-methoxycarbonyl-ethyl)-imidazolidin-2-one

Example 22

1-(4-Cyano-phenyl)-3-[4-(2-phosphono-ethyl)-phenyl]-imidazolidin-2-one

Prepared from a mixture of 1-(4-cyano-phenyl)-3-[4-[2-(dimethoxy-phosphoryl)-ethyl]-phenyl]-imidazolidin-2-one, sodium iodide and trimethylchlorosilane in acetonitrile by stirring at 40° C.

The following compound was obtained analogously:

(1) 1-(4-cyano-phenyl)-3-[4-[2-(O-methyl-phosphono)-ethyl]-phenyl]-imidazolidin-2-one Sodium iodide was used on its own and the work was done by refluxing in methylethylketone.

Example 23

1-(4-Cyano-phenyl)-3-[4-(2-methoxycarbonyl-ethyl)-phenyl]-imidazolidin-2-thione

Prepared by heating 1-(4-cyano-phenyl)-3-[4-(2-methoxycarbonyl-ethyl)-phenyl]-imidazolidin-2-one with 2,4-bis-(4-methoxyphenyl)-1,3-dithia-2,4-diphosphetan-2,4-disulphide in xylene.

The following compounds were obtained analogously:

(1) 4-(4-cyano-phenyl)-1-[4-(2-methoxycarbonyl-ethyl)-phenyl]-3H-imidazol-2-thione (2) 1-(4-cyano-phenyl)-4-[4-(2-methoxycarbonyl-ethyl)-phenyl]-3H-imidazol-2-thione

Example 24

4-(4'-Cyano-4-biphenylyl)-1-(2-methoxycarbonyl-ethyl)-3-methyl-3H-imidazol-2-one A mixture of 8.4 g of 4-cyano-4'-[(2-methoxycarbonyl-ethyl)-aminomethyl-carbonyl]-biphenyl hydrochloride, 2.8 ml of methylisocyanate and 50 ml of pyridine was refluxed for 3 hours and then stirred into a mixture of ice and hydrochloric acid. It was extracted with ethyl acetate, the organic phase was concentrated by evaporation and the residue was triturated, until it crystallised, with a 1:1 mixture of ethyl acetate and ether.

Yield: 2.1 g (35% of theory),

Melting point: 128°–130° C.

The following compounds were obtained analogously:

(1) 4-(4-cyano-phenyl)-1-[4-(2-methoxycarbonyl-ethyl)-phenyl]-3H-imidazol-2-one

Trimethylsilylisocyanate was used.

(2) 4-(4-cyano-phenyl)-1-[4-(2-methoxycarbonyl-ethyl)-phenyl]-3-phenyl-3H-imidazol-2-one (3) 4-(4-cyano-phenyl)-1-[4-(2-methoxycarbonyl-ethyl)-phenyl]-3-methyl-3H-imidazol-2-thione Methylisothiocyanate was used.

(4) 4-(4-cyano-phenyl)-1-[4-(2-methoxycarbonyl-ethyl)-phenyl]- 3-phenyl-3H-imidazol-2-thione Phenylisothiocyanate was used.

(5) 4-(4-cyano-phenyl)-1-[4-(2-methoxycarbonyl-ethyl)-phenyl]-5-methyl-3H-imidazol-2-one (6) 4-(4-cyano-phenyl)-3,5-dimethyl-1-[4-(2-methoxycarbonyl-ethyl)-phenyl]-3H-imidazol-2-one (7) 4-(4-cyano-phenyl)-1-[4-(2-methoxycarbonyl-ethyl)-phenyl]-5-methyl-3-phenyl-3H-imidazol-2-one (8) 1-(4-cyano-phenyl)-4-[4-(2-methoxycarbonyl-ethyl)-phenyl]-3H-imidazol-2-one (9) 1-(4-cyano-phenyl)-4-[4-(2-methoxycarbonyl-ethyl)-phenyl]-3-methyl-3H-imidazol-2-one

(10) 1-(4-cyano-phenyl)-4-[4-(2-methoxycarbonyl-ethyl)-phenyl]-3-phenyl-3H-imidazol-2-one

(11) 1-(4-cyano-phenyl)-4-[4-(2-methoxycarbonyl-ethyl)-phenyl]-3-methyl-3H-imidazol-2-thione

(12) 1-(4-cyano-phenyl)-4-[4-(2-methoxycarbonyl-ethyl)-phenyl]-3-phenyl-3H-imidazol-2-thione

(13) 1-(4-cyano-phenyl)-4-[4-(2-methoxycarbonyl-ethyl)-phenyl]-5-methyl-3-phenyl-3H-imidazol-2-one

(14) 1-(4-cyano-phenyl)-3,5-dimethyl-4-[4-(2-methoxycarbonyl-ethyl)-phenyl]-3H-imidazol-2-one

(15) 1-(4-cyano-phenyl)-4-[4-(2-methoxycarbonyl-ethyl)-phenyl]-5-methyl-3H-imidazol-2-one

(16) 4-(4,-cyano-4-biphenylyl)-1-(2-methoxycarbonyl-ethyl)-3H-imidazol-2-one

Potassium isocyanate and water were used as solvents.

Melting point: 235°–240° C.

(17) 4-(4-cyano-phenyl)-1-[4-(2-methoxycarbonyl-ethyl)-phenyl]-3-methyl-3H-imidazol-2-one Prepared from the methyl 4-[(4-cyano-phenacyl)-amino]-cinnamate prepared in situ according to Example IV without the addition of auxiliary base.

Melting point: 140°–144° C.

(18) 4-(4'-cyano-4-biphenylyl)-1-(2-methoxycarbonyl-ethyl)-3-phenyl-3H-imidazol-2-one Melting point: 103°–107° C.

(19) 4-(4'-cyano-4-biphenylyl)-1-(2-methoxycarbonyl-ethyl)-3H-imidazol-2-thione

(20) 4-(4'-cyano-4-biphenylyl)-1-(2-methoxycarbonyl-ethyl)-3 -methyl-3H-imidazol-2-thione

(21) 4-(4'-cyano-4-biphenylyl)-1-(2-methoxycarbonyl-ethyl) -3-phenyl-3H-imidazol-2-thione

(22) 4-(4'-cyano-4-biphenylyl)-1-(2-methoxycarbonyl-ethyl)-5-methyl-3H-imidazol-2-one

(23) 4-(4'-cyano-4-biphenylyl)-3,5-dimethyl-1-(2-methoxycarbonyl-ethyl)-3H-imidazol-2-one

(24) 4-(4'-cyano-4-biphenylyl)-1-(2-methoxycarbonyl-ethyl)-5-methyl-3-phenyl-3H-imidazol-2-one

Example 25

1-(4-Cyano-phenyl)-3-[4-(2-methoxycarbonyl-ethyl)-cyclohexyl]-imidazolidin-2-one A mixture of 2.25 g of 1-[4-(2-methoxycarbonyl-ethyl)-cyclohexyl]-imidazolidin-2-one, 2.25 g of 4-iodo-benzonitrile, 0.29 g of tris-[2-(2-methoxy-ethoxy)-ethyl]-amine, 2.46 g of potassium carbonate, 0.2 g of copper(I) chloride, 0.2 g of copper(I)iodide and 60 ml of xylene was heated under nitrogen for 4 hours using a water separator. The mixture was allowed to cool to 50° C., 150 ml of ethyl acetate were added, the precipitate was filtered off while hot and washed with hot ethyl acetate. The ethyl acetate phases were evaporated to dryness and the residue was purified by column chromatography over silica gel (eluant: cyclohexane/ethyl acetate=1:1).

Yield: 1.7 g (54% of theory), $R_f$ value: 0.56 (silica gel; cyclohexane/ethyl acetate=1:1)

The following compound was obtained analogously:

(1) 2-64=cyano-phenyl)-5-[4-(2-methoxycarbonyl-ethyl)-phenyl]-3,4-dihydro-2H,5H-1,2,5-thiadiazole-1,1-dioxide 4-Fluoro-benzonitrile and sodium hydride in N-methyl-pyrrolidone were used without copper salts.

Melting point: 160°–162° C.

Example 26

3-(4-Cyano-phenyl)-1-[4-(2-methoxycarbonyl-ethyl)-phenyl]-4-methyl-3H-imidazol-2-one 3 g of N-(4-cyano-phenyl)-N'-(2-hydroxy-propyl)-N'-[4-(2-methoxycarbonyl-ethyl)-phenyl]-urea were dissolved in a mixture of 40 ml of methylene chloride and 20 ml of dimethylsulphoxide and 0.64 ml of pyridine, 0.61 ml of trifluoroacetic acid and 4.9 g of N,N'-dicyclohexyl-carbodiimide were added successively. The mixture was stirred for 4.5 hours at ambient temperature, a further 5 ml of trifluoroacetic acid were added and the mixture was heated for one hour to 50° C. It was left to stand for 16 hours at ambient temperature, diluted with 150 ml of methylene chloride and washed several times with water. The methylene chloride phase was evaporated down and the residue was purified by column chromatography over silica gel (eluant: methylene chloride/cyclohexane/ethyl acetate=2:1:1).

Yield: 0.8 g (28% of theory), $R_f$ value: 0.55 (silica gel; methylene chloride/cyclohexane/ethyl acetate=3:1:1)

The following compound was obtained analogously:

(1) 1-(4-cyano-phenyl)-3-[4-(2-methoxycarbonyl-ethyl)-phenyl]-4-methyl-3H-imidazol-2-one Melting point: 168°–170° C.

$R_f$ value: 0.55 (silica gel; methylene chloride/cyclohexane/ethyl acetate=2:1:1)

Example 27

4-(4-Cyano-phenyl)-2-[4-(2-ethoxycarbonyl-ethyl)-phenyl]-5-methyl-4H-1,2,4-triazol-3-one 1.75 g of N-acetylamino-N-[4-(2-ethoxycarbonyl-ethyl)-phenyl]-N'-(4-cyano-phenyl)-urea were heated to 180° C. for 1.5 hours. The compound was triturated with 8 ml of ethanol and the resulting product was filtered off.

Yield: 0.66 g (40% of theory),

Melting point: 170°–172° C.

$R_f$ value: 0.91 (silica gel; ethyl acetate/cyclohexane=2:1)

The following compounds were obtained analogously:

(1) 4-(4-cyano-phenyl)-2-[4-(2-methoxycarbonyl-ethyl)-phenyl]-4H-1,2,4-triazol-3-one Melting point: 213°–215° C.

$R_f$ value: 0.69 (silica gel; methylene chloride/ethyl acetate=9:1)

(2) 2-(4-cyano-phenyl)-4-[4-(2-methoxycarbonyl-ethyl)-phenyl]-4H-1,2,4-triazol-3-one $R_f$ value: 0.62 (silica gel; methylene chloride/ethyl acetate=9:1)

(3) 2-(4-cyano-phenyl)-4-[4-(2-methoxycarbonyl-ethyl)-phenyl]-5-methyl-4H-1,2,4-triazol-3-one Melting point: 163°–164° C.

$R_f$ value: 0.65 (silica gel; methylene chloride/ethyl acetate=9:1)

(4) 1-(4-cyano-phenyl)-3-[4-(2-methoxycarbonyl-ethyl)-phenyl]-imidazolidin-2,4-dione Melting point: 188°–190° C.

$R_f$ value: 0.57 (silica gel; cyclohexane/ethyl acetate=4:6)

(5) 2-(4-cyano-phenyl)-4-[4-(2-ethoxycarbonyl-ethyl)-phenyl]-5-ethyl-4H-1,2,4-triazol-4-one The starting compound was refluxed in xylene in the presence of toluenesulphonic acid.

Melting point: 159°–161° C.

$R_f$ value: 0.68 (silica gel; methylene chloride/ethyl acetate=9:1)

Example 28

1-[6-(4-Cyano-phenyl)-3-pyridazinyl]-3-(2-methoxycarbonyl-ethyl)-imidazolidin-2-one 2.2 g of 1-[6-(4-cyano-phenyl)-3-pyridazinyl]-imidazolidin-2-one were stirred into 160 ml of dimethylformamide with 0.33 g of a 60% suspension of sodium hydride in oil for 3 hours at ambient temperature. 2 ml of methyl acrylate were added and the mixture was stirred for a further 16 hours at ambient temperature. The reaction mixture was poured onto a mixture of 300 ml of water and 8 ml of 1N hydrochloric acid, the product precipitated was filtered off, brought to the boil with methanol and, after cooling, filtered again.

Yield: 1.8 g (60% of theory), $R_f$ value: 0.46 (silica gel; methylene chloride/methanol=15:1, developing twice)

The following compound was obtained analogously:

(1) 3-(4'-cyano-4-biphenylyl)-1-(2-methoxycarbonyl-ethyl)-3H-imidazo[4,5-b]pyridin-2-one $R_f$ value: 0.81 (silica gel; methylene chloride/methanol=19:1)

Example 29

1-(2-tert.Butoxycarbonylmethylamino-ethyl)-3-(4-cyano-phenyl)-imidazolidin-2-one A solution of 4.6 g of 1-(4-cyano-phenyl)-3-(2-methanesulphonyloxy-ethyl)-imidazolidin-2-one in 75 ml of dimethylformamide was mixed with 2.1 g of potassium carbonate at ambient temperature, with stirring, and then 2.1 ml of glycine-tert.butylester were added dropwise. The resulting mixture was stirred for 16 hours at ambient temperature and 30 hours at 60° C. The solvent was distilled off in vacuo and the residue was taken up in a mixture of 150 ml of ice water and 100 ml of methylene chloride. The methylene chloride phase was separated off and washed with water. The aqueous phases were then extracted once more with methylene chloride and finally the combined organic phases were evaporated down. The residue was purified over silica gel (eluant: ethyl acetate/methanol/conc. ammonia=9.5:0.5:0.1).

Yield: 1.4 g (27% of theory),

Melting point: 104°–106° C.

R$_f$ value: 0.32 (silica gel; ethyl acetate/methanol/conc. ammonia=9:1:0.1)

Example 30

1-[2-(N-Acetyl-N-carboxymethyl-amino)-ethyl]-3-(4-amidino-phenyl)-imidazolidin-2-one A mixture of 0.3 g of 1-(4-amidino-phenyl)-3-(2-carboxymethylamino-ethyl)-imidazolidin-2-one prepared under ice cooling, 20 ml of water and 2.35 ml of acetanhydride was allowed to return to ambient temperature with stirring and stirred for a further 30 minutes. It was then evaporated to dryness in vacuo and the residue was purified by chromatography on silica gel (eluant: methanol/glacial acetic acid/water=6:1:1)

Yield: 0.2 g (57% of theory).

Melting point: 302°–304° C. (decomp.)

R$_f$ value: 0.54 (silica gel; methanol/2N aqueous ammonia= 4:1)

Example 31

1-[4-(1-Amino-ethyl)-phenyl]-3-[4-(2-methoxycarbonyl-ethyl)-phenyl]-imidazolidin-2-one hydrochloride 0.5 g of 1-[4-(1-hydroxyimino-ethyl)-phenyl]-3-[4-(2-methoxycarbonyl-ethyl)-phenyl]-imidazolidin-2-one were treated with hydrogen at 5 bars for 3.5 hours at ambient temperature in a mixture of 50 ml of methanol and 1 ml of methanolic hydrochloric acid in the presence of 100 mg of 10% palladium/charcoal. The mixture was evaporated down and the residue was taken up in a mixture of 20 ml of methylene chloride, 15 ml of methanol, 20 ml of water and 0.1 ml of 6N hydrochloric acid. The aqueous phase was separated off and evaporated down to about one third of its volume, whereupon the product crystallised out.

Yield: 0.28 g (53% of theory).

Melting point: 264°–266° C.

R$_f$ value: 0.51 (Reversed Phase Plate RP8, methanol/5% sodium chloride solution=6:4)

The following compounds were obtained analogously:

(1) 1-(1-amino-5-indanyl)-3-[4-(2-methoxycarbonyl-ethyl)-phenyl]-imidazolidin-2-one hydrochloride Melting point: 223°–226° C. (sintering from 208° C.)

(2) 1-(1-amino-1,2,3,4-tetrahydro-6-naphthyl)-3-[4-(2-methoxycarbonyl-ethyl)-phenyl]-imidazolidin-2-one hydrochloride

Example 32

1-(4-Amino-cyclohexyl)-3-[4-(3-methoxycarbonyl-propyl)-phenyl]-imidazolidin-2-one Prepared from 1-(4-aminocarbonyl-cyclohexyl)-3-[4-(3-methoxycarbonyl-propyl)-phenyl]-imidazolidin-2-one by treating with [bis-(trifluoroacetoxy) iodo]benzene in acetonitrile/water at ambient temperature.

The following compounds were obtained analogously:

(1) 1-(4-amino-cyclohexyl)-3-[4-(2-methoxycarbonyl-ethyl)-phenyl]-imidazolidin-2-one (2) 1-[4-(2-amino-2-propyl)-phenyl]-3-[4-(2-methoxycarbonyl-ethyl)-phenyl]-imidazolidin-2-one

Example 33

1-[4-[(2-Methoxycarbonyl-ethyl)-aminocarbonyl]-phenyl]-3-(4-piperidinyl)-imidazolidin-2-one Prepared by treating 1-(1-benzyloxycarbonyl-4-piperidinyl)-3-[4-[(2-methoxycarbonyl-ethyl)-aminocarbonyl]-phenyl]-imidazolidin-2-one with hydrogen at 3 bars in the presence of 5% palladium/charcoal in methanol.

The following compounds were obtained analogously:

(1) 1-(4-amino-cyclohexyl)-3-[4-[(2-methoxycarbonyl-ethyl)-aminocarbonyl]-phenyl]-imidazolidin-2-one (2) 1-[4-(2-methoxycarbonyl-ethyl)-phenyl]-3-[4-(methylaminomethyl)-phenyl]-imidazolidin-2-one (3) 1-[4-(2-methoxycarbonyl-ethyl)-phenyl]-3-[4-(n-propylamino-methyl)-phenyl]-imidazolidin-2-one

Example 34

1-[4-(1-Amino-cyclopropyl)-phenyl]-3-[4-(2-methoxycarbonyl-ethyl)-phenyl]-imidazolidin-2-one Prepared from 1-[4-(1-tert.butyloxycarbonylamino-cyclopropyl)-phenyl]-3-[4-(2-methoxycarbonyl-ethyl)-phenyl]-imidazolidin-2-one by stirring for two hours in a 1:1 mixture of methylene chloride and trifluoroacetic acid.

The following compound was obtained analogously:

(1) 1-[4-(1-amino-cyclopentyl)-phenyl]-3-[4-[(2-methoxycarbonyl-ethyl)-phenyl]-imidazolidin-2-one

Example 35

1-[4-(2-Methoxycarbonyl-ethyl)-phenyl]-3-[4-(methylamino-methyl)-phenyl]-imidazolidin-2-one Prepared from 1-(4-aminomethyl-phenyl)-3-[4-(2-methoxycarbonyl-ethyl)-phenyl]-imidazolidin-2-one by alkylation with methyliodide in dimethylsulphoxide.

The following compounds were obtained analogously:

(1) 1-[4-(2-methoxycarbonyl-ethyl)-phenyl]-3-[4-(n-propylamino-methyl)-phenyl]-imidazolidin-2-one (2) 1-[4-(2-methoxycarbonyl-ethyl)-aminocarbonyl]-phenyl]-3-(1-methyl-4-piperidinyl)-imidazolidin-2-one

Example 36

1-(4-Cyano-2-methyl-phenyl)-3-[4-(2-methoxycarbonyl-ethyl)-phenyl]-imidazolidin-2-one 3.0 g of 1-(4-bromo-2-methyl-phenyl)-3-[4-(2-methoxycarbonyl-ethyl)-phenyl]-imidazolidin-2-one and 1.3 g of copper(I)cyanide were heated in 10 ml of dimethylformamide for 10 hours at a bath temperature of 175° C. The dimethylformamide was evaporated off in vacuo, the residue was digested with chloroform and filtered off. The chloroform solution was washed with water and saturated saline solution and concentrated by evaporation. The residue was purified by column chromatography (silica gel; methylene chloride/ethyl acetate=100:2)

Yield: 1.4 g (54% of theory).

Melting point: 151°–153° C.

Example 37

1-[4-(Dimethylamino-methyl)-phenyl]-3-[4-(2-methoxycarbonyl-ethyl)-phenyl]-imidazolidin-2-one Prepared from 1-(4-aminomethyl-phenyl)-3-[4-(2-methoxycarbonyl-ethyl)-phenyl]-imidazolidin-2-one by treating with formaldehyde and sodium cyanoborohydride.

Example 38

Dry ampoule containing 2.5 mg of active substance per 1 ml

| Composition: | |
|---|---|
| Active substance | 2.5 mg |
| Mannitol | 50.0 mg |
| Water for injections ad | 1.0 ml |

Preparation:

The active substance and mannitol were dissolved in water. After packaging, the ampoules were freeze-dried.

The solution ready for use was made up with water for injections.

Example 39

Dry ampoule containing 35 mg of active substance per 2 ml

| Composition: | |
|---|---|
| Active substance | 35.0 mg |
| Mannitol | 100.0 mg |
| Water for injections ad | 2.0 ml |

Preparation:

The active substance and mannitol were dissolved in water. After packaging, the ampoules were freeze-dried.

The solution ready for use was made up with water for injections.

Example 40

Tablet containing 50 mg of active substance

| Composition: | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) were mixed together and granulated with an aqueous solution of (4). (5) was added to the dried granules. From this mixture, compressed tablets were made, which were biplanar, facetted on both sides and notched on one side. Diameter of tablets: 9 mm.

Example 41

Tablet containing 350 mg of active substance

| Composition: | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) were mixed together and granulated with an aqueous solution of (4). (5) was added to the dried granules. From this mixture, compressed tablets were made, which were biplanar, facetted on both sides and notched on one side. Diameter of tablets: 12 mm.

Example 42

Capsules containing 50 mg of active substance

| Composition: | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) was triturated with (3). This trituration was added to the mixture of (2) and (4) with thorough mixing.

The powdered mixture was packed into hard gelatin oblong capsules, size 3, in a capsule filling machine.

Example 43

Capsule containing 350 mg of active substance

| Composition: | |
|---|---|
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) was triturated with (3). This trituration was added to the mixture of (2) and (4) with thorough mixing.

The powdered mixture was packed into hard gelatin oblong capsules, size 0, in a capsule filling machine.

What is claimed is:

1. An imidazolidindione of formula

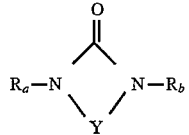

wherein

Y represents a —$CR_cR_dCO$— group, wherein
  $R_c$ represents a hydrogen atom, an $C_{1-3}$-alkyl, trifluoromethyl or phenyl group, and
  $R_d$ represents a hydrogen atom or an $C_{1-3}$-alkyl group;
one of the groups $R_a$ or $R_b$ represents a group of formula

-A-B-C- wherein

A represents a straight-chained or branched $C_{1-4}$-aminoalkyl group, an amino, amidino or guanidino group, wherein in each of the above-mentioned groups, at one of the nitrogen atoms, one hydrogen atom may be replaced by a $C_{1-4}$-alkyl group or an alkoxycarbonyl group having a total of 2 to 5 carbon atoms or by a benzyloxycarbonyl group, B represents a bond, a phenylene group which may be substituted by one or two $C_{1-4}$-alkyl groups, by a fluorine, chlorine, bromine or iodine atom, by a trifluoromethyl, $C_{1-4}$-alkoxy, $C_{1-4}$-alkylsulphenyl, $C_{1-4}$-alkylsulphinyl, $C_{1-4}$-alkylsulphonyl, nitro, amino, acetylamino, benzoylamino or methanesulphonylamino group, or a $C_{3-6}$-cycloalkylene group, C represents an ethylene group optionally substituted by a hydroxy group, a methylenecarbonyl group linked to the group B via the carbonyl group, or a phenylene group which may be substituted by one or two $C_{1-4}$-alkyl groups, by a fluorine, chlorine, bromine or iodine atom, by a trifluoromethyl, $C_{1-4}$-alkoxy, $C_{1-4}$-alkylsulphenyl, $C_{1-4}$-alkylsulphinyl, $C_{1-4}$-alkylsulphonyl, nitro, amino, acetylamino, benzoylamino or methanesulphonylamino group, the other of the groups $R_a$ or $R_b$ represents a group of formula

F-E-D- wherein

D represents a $C_{1-4}$-alkylene group, a phenylene group which may be substituted by one or two $C_{1-4}$-alkyl groups, by a fluorine, chlorine, bromine or iodine atom, by a trifluoromethyl, $C_{1-4}$-alkoxy, $C_{1-4}$-alkylsulphenyl, $C_{1-4}$-alkylsulphinyl, $C_{1-4}$-alkylsulphonyl, carboxymethoxy, methoxycarbonylmethoxy, nitro, amino, acetylamino, benzoylamino or methanesulphonylamino group, a cyclohexylene group optionally substituted by one or two methyl groups, or a 1,4-piperidinylene group, which is linked via the 1-position to the optionally substituted $C_{1-4}$-alkylene group of E with the proviso that the nitrogen atom of the 1,4-piperidinylene group is separated by at least 2 carbon atoms from a heteroatom of the optionally substituted $C_{1-4}$-alkylene group of E;

E represents a bond, a $C_{1-4}$-alkylene group optionally substituted by one or two methyl groups or by a hydroxy, methoxy, amino, methylamino, dimethylamino, dibenzylamino, carboxymethyl or methoxycarbonylmethyl group, a $C_{2-3}$-alkenylene group, a phenylene group which may be substituted by one or two $C_{1-4}$-alkyl groups, by a fluorine, chlorine, bromine or iodine atom, by a trifluoromethyl or $C_{1-4}$-alkoxy group, or a $C_{1-2}$-alkylene group linked to group D by the group W', wherein W' represents an oxygen or sulphur atom, a sulphinyl, sulphonyl, —NH—, —N($C_{1-4}$-alkyl)-, —N(COC$_{1-4}$-alkyl)-, —N(SO$_2$C$_{1-4}$-alkyl)-, aminocarbonyl or carbonylamino group; and F represents a carbonyl group substituted by a hydroxy group, by a $C_{1-6}$-alkoxy group or by a phenylalkoxy group having 1 or 2 carbon atoms in the alkoxy part, wherein if A represents an amino or aminoalkyl group optionally benzyloxycarbonylated at the nitrogen atom, the shortest distance between the nitrogen atom of this group and group F is at least 10 bonds;

the tautomers, the stereoisomers, including the mixtures thereof, or the addition salts thereof.

2. The imidazolidindione as recited in claim 1, wherein

Y represents a —CR$_c$R$_d$CO— group, wherein

R$_c$ represents a hydrogen atom, an $C_{1-3}$-alkyl, trifluoromethyl or phenyl group, and Rd represents a hydrogen atom or an $C_{1-3}$-alkyl group;

one of the groups $R_a$ or $R_b$ represents a group of the formula

A-B-C- wherein

A represents a straight-chained or branched $C_{1-4}$-aminoalkyl group, an amino or amidino group, wherein in each of the above-mentioned groups, at one of the nitrogen atoms, a hydrogen atom may be replaced by an alkoxycarbonyl group having a total of 2 to 5 carbon atoms or by a benzyloxycarbonyl group;

B represents a bond, a phenylene group which may be substituted by a fluorine, chlorine or bromine atom, by a methyl, trifluoromethyl or methoxy group, and C represents a phenylene group which may be substituted by one or two methyl groups, by a fluorine, chlorine or bromine atom, by a methyl, trifluoromethyl or methoxy group.

the other of the groups $R_a$ or $R_b$ represents a group of formula

F-E-D- wherein

D represents a $C_{1-4}$-alkylene group, a phenylene group which may be substituted by a fluorine, chlorine or bromine atom, by a methyl, trifluoromethyl or methoxy group, a cyclohexylene group, or a 1,4-piperidinylene group, which is linked via the 1-position to the optionally substituted methylene or ethylene group of E with the proviso that the nitrogen atom of the 1,4-piperidinylene group is separated by at least 2 carbon atoms from a heteroatom of the optinally substituted methylene or ethylene group of E;

E represents a bond, a methylene or ethylene group optionally substituted by one or two methyl groups or by an amino or dibenzylamino group, an ethenylene or phenylene group or a methylene group linked to group D by the group W', wherein W' represents an oxygen or sulphur atom, a sulphinyl, sulphonyl, —NH—, —N($C_{1-2}$-Alkyl)-, —N(COC$_{1-2}$-Alkyl)- or —N(SO$_2$C$_{1-2}$-Alkyl)- group; and F represents a carbonyl group substituted by a hydroxy group or by a $C_{1-6}$-alkoxy group, wherein if A represents an amino or aminoalkyl group optionally benzyloxycarbonylated at the nitrogen atom, the shortest distance between the nitrogen atom of this group and group F is at least 10 bonds;

the tautomers, the stereoisomers, including the mixtures thereof, or the addition salts thereof.

3. The imidazolidindione as recited in claim 1, wherein

Y represents a —$CR_cR_dCO$— group, wherein
$R_c$ represents a hydrogen, a methyl, ethyl, trifluoromethyl or phenyl group, and
$R_d$ represents a hydrogen atom; one of the groups $R_a$ or $R_b$ represents a group of formula

A-B-C- wherein

A represents an aminomethyl or amidino group optionally substituted by an alkoxycarbonyl group with a total of 2 to 5 carbon atoms;

B represents a bond or a 1,4-phenylene group; and

C represents a 1,4-phenylene group, the other of the groups $R_a$ or $R_b$ represents a group of the formula

F-E-D- wherein

D represents a $C_{1-4}$-alkylene, 1,4-phenylene or 1,4-cyclohexylene group, or a 1,4-piperidinylene group, which is linked via the 1-position to the ethylene group optionally substituted by one or two methyl groups of E;

E represents a bond, an ethylene group optionally substituted by one or two methyl groups, or an ethenylene group, or a methylene group linked by the group W' to a carbon atom of the group D, wherein W' represents an oxygen or sulphur atom, a sulphinyl, sulphonyl, —NH— or —N(CH$_3$)— group;

F represents a carbonyl group substituted by a hydroxy group or by a $C_{1-6}$-alkoxy group, wherein if A represents an aminomethyl group, the shortest distance between the nitrogen atom of this group and group F is at least 10 bonds; the tautomers, the stereoisomers, including the mixtures thereof, or the addition salts thereof.

4. The imidazolidindione as recited in claim 1, wherein

Y represents a —$CR_cR_dCO$— group, wherein
$R_c$ represents a hydrogen, a methyl or ethyl group, and
$R_d$ represents a hydrogen atom;

one of the groups $R_a$ or $R_b$ represents a group of formula

A-B-C- wherein

A represents an amidino group optionally substituted by an alkoxycarbonyl group with a total of 2 to 5 carbon atoms;

B represents a bond; and

C represents a 1,4-phenylene group, the other of the groups $R_a$ or $R_b$ represents a group of the formula

F-E-D- wherein

D represents a 1,4-phenylene group;

E represents an ethylene group, and

F represents a carbonyl group substituted by a hydroxy group or by a $C_{1-4}$-alkoxy group;

the tautomers, the stereoisomers, including the mixtures thereof, or the addition salts thereof.

5. 1-(4-amidino-phenyl)-3-[4-(2-carboxy-ethyl)-phenyl]-imidazolidin-2,4-dione, or the addition salts thereof.

* * * * *